US012758377B2

(12) United States Patent
Martin et al.

(10) Patent No.: US 12,758,377 B2
(45) Date of Patent: Oct. 13, 2026

(54) FENESTRATION DEVICES, SYSTEMS, AND METHODS FOR AORTIC ARCH REPAIR

(71) Applicant: Medtronic, Inc., Minneapolis, MN (US)

(72) Inventors: G Ray Martin, Redwood City, CA (US); Steven Kim, Los Altos, CA (US); Hanson Gifford, Woodside, CA (US); Katie Miyashiro, San Francisco, CA (US); Doug Sutton, Pacifica, CA (US)

(73) Assignee: Medtronic, Inc., Minneapolis, MN (US)

( * ) Notice: Subject to any disclaimer, the term of this patent is extended or adjusted under 35 U.S.C. 154(b) by 593 days.

(21) Appl. No.: 18/202,853

(22) Filed: May 26, 2023

(65) Prior Publication Data

US 2023/0380953 A1 Nov. 30, 2023

Related U.S. Application Data

(60) Provisional application No. 63/346,705, filed on May 27, 2022.

(51) Int. Cl.
*A61F 2/07* (2013.01)
*A61F 2/06* (2013.01)

(52) U.S. Cl.
CPC .......... *A61F 2/07* (2013.01); *A61F 2002/061* (2013.01); *A61F 2002/075* (2013.01); *A61F 2250/0039* (2013.01)

(58) Field of Classification Search
CPC .................. A61F 2/07; A61F 2002/061; A61F 2002/075; A61F 2250/0039; A61F 2002/065; A61F 2002/072
See application file for complete search history.

(56) References Cited

U.S. PATENT DOCUMENTS 7,335,224 B2 2/2008 Cook
8,052,741 B2 11/2011 Bruszewski
(Continued)

FOREIGN PATENT DOCUMENTS

EP 3003230 A1 4/2016
EP 3714838 A1 9/2020
(Continued)

OTHER PUBLICATIONS

International Search Report and Written Opinion mailed Aug. 21, 2023 in International Application No. PCT/US23/23767, 14 pages.
(Continued)

*Primary Examiner* — Suzette J Gherbi
(74) *Attorney, Agent, or Firm* — Medler Ferro Woodhouse & Mills PLLC

(57) ABSTRACT

Aortic repair devices and associated systems and methods are disclosed herein. An aortic repair device configured in accordance with embodiments of the present technology can include a base member configured to be implanted in an aorta proximate to a diseased portion of the aorta, such as an aneurysm or dissection. The base member can direct blood flow past the diseased portion of the aorta to perfuse a portion of the aorta distal of the diseased portion. In some embodiments, one or more branch members can be coupled to the base member during the same or a separate intravascular procedure to perfuse one or more branching vessels of the patient's aorta. The branch members can be coupled to the base member via an ex situ or in situ fenestration formed through the base member.

40 Claims, 36 Drawing Sheets

(56) References Cited

U.S. PATENT DOCUMENTS

| | | | | |
|---|---|---|---|---|
| 8,337,546 | B2 | 12/2012 | Bruszewski | |
| 8,506,622 | B2 | 8/2013 | Bruszewski | |
| 8,540,764 | B2 * | 9/2013 | Bruszewski | A61F 2/07 623/1.13 |
| 8,702,791 | B2 | 4/2014 | Kelly | |
| 8,734,504 | B2 | 5/2014 | Kelly | |
| 8,945,203 | B2 * | 2/2015 | Shalev | A61F 2/90 623/1.13 |
| 8,998,971 | B1 | 4/2015 | Kelly | |
| 9,005,268 | B2 | 4/2015 | Ernest | |
| 9,095,421 | B2 | 8/2015 | Peterson | |
| 9,101,456 | B2 | 8/2015 | Hartley | |
| 9,259,336 | B2 | 2/2016 | Schaeffer | |
| 9,283,068 | B2 | 3/2016 | Kelly | |
| 9,314,328 | B2 | 4/2016 | Dake | |
| 9,370,413 | B2 | 6/2016 | Kelly | |
| 9,393,101 | B2 | 7/2016 | Kelly | |
| 9,393,102 | B2 | 7/2016 | Kelly | |
| 9,402,751 | B2 | 8/2016 | Zukowski | |
| 9,427,308 | B2 | 8/2016 | Kelly | |
| 9,463,102 | B2 | 10/2016 | Kelly | |
| 9,592,112 | B2 | 3/2017 | Arbefeuille | |
| 9,649,188 | B2 | 5/2017 | Hartley | |
| 9,655,711 | B2 | 5/2017 | Hartley | |
| 9,668,892 | B2 * | 6/2017 | Shalev | A61F 2/07 |
| 9,788,933 | B2 | 10/2017 | Sun | |
| 9,839,542 | B2 | 12/2017 | Bruszewski | |
| 9,949,818 | B2 | 4/2018 | Kelly | |
| 9,980,832 | B2 | 5/2018 | Kelly | |
| 9,993,360 | B2 | 6/2018 | Shalev | |
| 10,034,741 | B2 | 7/2018 | Kelly | |
| 10,201,413 | B2 | 2/2019 | Shalev | |
| 10,231,822 | B2 | 3/2019 | Hartley | |
| 10,285,799 | B2 | 5/2019 | Hartley | |
| 10,350,052 | B2 | 7/2019 | Kelly | |
| 10,357,353 | B2 | 7/2019 | Kelly | |
| 10,390,930 | B2 | 8/2019 | Arbefeuille | |
| 10,405,965 | B2 | 9/2019 | Kelly | |
| 10,485,651 | B2 | 11/2019 | Hartley | |
| 10,492,900 | B2 | 12/2019 | Kelly | |
| 10,588,735 | B2 | 3/2020 | Dake | |
| 10,646,323 | B2 | 5/2020 | Majolagbe | |
| 10,702,369 | B2 | 7/2020 | Perkins | |
| 10,779,931 | B2 | 9/2020 | Hartley | |
| 10,888,413 | B2 | 1/2021 | Shalev | |
| 10,925,712 | B2 | 2/2021 | Kelly | |
| 10,952,884 | B2 | 3/2021 | Shalev | |
| 11,083,605 | B2 | 8/2021 | Perkins | |
| 2004/0138734 | A1 | 7/2004 | Chobotov | |
| 2005/0010277 | A1 * | 1/2005 | Chuter | A61F 2/064 623/1.13 |
| 2007/0208410 | A1 * | 9/2007 | Berra | A61F 2/954 623/1.13 |
| 2011/0130819 | A1 | 6/2011 | Cragg et al. | |
| 2011/0276062 | A1 | 11/2011 | Bolduc | |
| 2013/0274850 | A1 | 10/2013 | Patrick | |
| 2019/0274813 | A1 | 9/2019 | Kelly | |
| 2019/0314138 | A1 | 10/2019 | O'Brien | |
| 2019/0350694 | A1 | 11/2019 | Arbefeuille | |
| 2019/0380825 | A1 | 12/2019 | Perkins | |
| 2020/0163751 | A1 | 5/2020 | Dake | |
| 2020/0289255 | A1 | 9/2020 | Perkins | |
| 2020/0306028 | A1 | 10/2020 | Hartley | |
| 2020/0306064 | A1 | 10/2020 | Perkins | |
| 2020/0306066 | A1 | 10/2020 | Perkins | |
| 2020/0315825 | A1 | 10/2020 | Marmur | |
| 2020/0352699 | A1 * | 11/2020 | Guo | A61F 2/07 |
| 2020/0390574 | A1 * | 12/2020 | Zhang | A61F 2/0077 |
| 2021/0000586 | A1 | 1/2021 | Perkins | |
| 2021/0030526 | A1 | 2/2021 | Perkins | |
| 2021/0059806 | A1 | 3/2021 | Perkins | |
| 2021/0077247 | A1 | 3/2021 | Shalev | |
| 2021/0093437 | A1 | 4/2021 | Perkins | |
| 2021/0093438 | A1 | 4/2021 | Perkins | |
| 2021/0236313 | A1 | 8/2021 | Stephens et al. | |
| 2021/0322188 | A1 | 10/2021 | Perkins | |
| 2022/0395365 | A1 * | 12/2022 | Lostetter | A61F 2/07 |
| 2023/0149149 | A1 * | 5/2023 | Cindrich | A61F 2/89 623/1.13 |
| 2023/0277297 | A1 | 9/2023 | Martin et al. | |
| 2025/0032284 | A1 * | 1/2025 | Newhauser | A61M 25/0026 |
| 2025/0049557 | A1 * | 2/2025 | Mendelsohn | A61F 2/07 |
| 2025/0107882 | A1 | 4/2025 | Martin et al. | |

FOREIGN PATENT DOCUMENTS

| | | | |
|---|---|---|---|
| EP | 3727312 | A1 | 10/2020 |
| EP | 3785665 | A1 | 3/2021 |
| WO | 2016075615 | A2 | 5/2016 |
| WO | 2019129153 | A1 | 7/2019 |
| WO | 2021195305 | A1 | 9/2021 |

OTHER PUBLICATIONS

International Search Report and Written Opinion mailed Jan. 10, 2025 in International Application No. PCT/US24/40871, 21 pages.

International Search Report and Written Opinion mailed Jan. 7, 2025 in International Application No. PCT/US24/39658, 24 pages.

International Search Report and Written Opinion mailed Jun. 16, 2023 in International Application No. PCT/US23/14649, 15 pages.

Invitation to Pay Additional Fees and, Where Applicable, Protest Fee mailed Nov. 15, 2024 in International Patent Application No. PCT/US24/40871, 19 pages.

Invitation to Pay Additional Fees and, Where Applicable, Protest Fee mailed Nov. 5, 2024 in International Patent Application No. PCT/US24/39658, 19 pages.

* cited by examiner

FENESTRATION DEVICES, SYSTEMS, AND METHODS FOR AORTIC ARCH REPAIR

CROSS-REFERENCE TO RELATED APPLICATION

The present application claims priority to U.S. Provisional App. No. 63/346,705, titled "FENESTRATION DEVICES, SYSTEMS, AND METHOD FOR AORTIC ARCH REPAIR," and filed May 27, 2022, the entirety of which is hereby incorporated by reference.

TECHNICAL FIELD

The present technology is directed to fenestration devices, systems, and methods for aortic arch repair, and more particularly to devices configured to be implanted at least partially within the proximal aorta to treat aneurysms and dissections in the ascending aorta and/or the aortic arch.

BACKGROUND

Aneurysms, dissections, penetrating ulcers, intramural hematomas, and/or transections may occur in blood vessels, and most typically occur in the aorta and peripheral arteries. A diseased region of the aorta may extend into areas having vessel bifurcations or segments of the aorta from which smaller "branch" arteries extend.

The diseased region of the aorta and other vessels can be bypassed with a stent graft placed inside the vessel to span the diseased region. The stent graft can effectively seal off the diseased region from further exposure to blood flow, preventing the aneurysm, dissection, or other type of diseased region from worsening.

However, the use of stent grafts to internally bypass a diseased region of a vessel is not without challenges. In particular, care must be taken so that the stent graft does not cover or occlude critical branch vessels, yet the stent graft must adequately seal against the healthy regions of the vessel wall and remain open to provide a flow conduit for blood to flow past the diseased region.

BRIEF DESCRIPTION OF THE DRAWINGS

Many aspects of the present disclosure can be better understood with reference to the following drawings. The components in the drawings are not necessarily to scale. Instead, emphasis is placed on clearly illustrating the principles of the present disclosure.

DETAILED DESCRIPTION

Figure 1A:
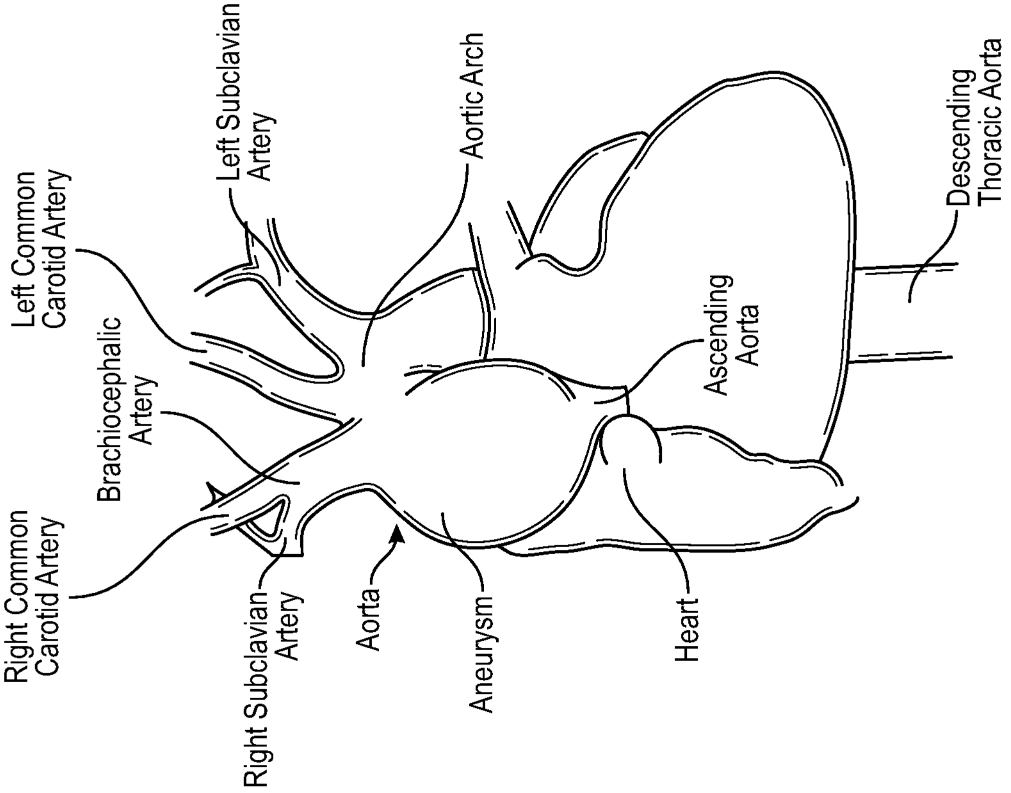
FIGS. 1A and 1B are side views of a diseased aorta and surrounding anatomy in which a fenestrated aortic repair device can be implanted in accordance with embodiments of the present technology.

The present technology is directed to fenestrated devices for treating a diseased aorta of a patient, such as a human patient, and associated systems and methods. In some embodiments, an aortic repair device includes a base member (also referred to as a "base component") configured to be implanted at least partially in a proximal region of an aorta proximate to a diseased portion of the aorta, such as an aneurysm or dissection at or surrounding the aortic arch, the ascending aorta, and/or the descending thoracic aorta. The base member can therefore provide a conduit for directing blood flow past the diseased portion of the aorta to perfuse a portion of the aorta distal of the diseased portion and/or various branch vessels. The base member can include one or more fenestrations that align with vessels branching from the aortic arch so as to provide openings through which blood can perfuse these branching vessels. In some embodiments, the base member receives one or more branch members (also referred to as "branch components" or "branch perfusion members") or other implants at the fenestrations and the base and branch members can be coupled together and/or to additional flow conduits extending into or toward the branching vessels. In some embodiments, at least one of the fenestrations in the base member is formed ex situ (e.g., before the base member is implanted). In these and other embodiments, at least one of the fenestrations in the base member can be formed in situ (e.g., after the base member has been implanted), or any other suitable time during an intravascular procedure.

Specific details of several embodiments of the present technology are described herein with reference to FIGS. 1A-34C. The present technology, however, can be practiced without some of these specific details. In some instances, well-known structures and techniques often associated with catheter-based delivery systems, implantable repair devices, and the like, have not been shown in detail so as not to obscure the present technology. The terminology used in the description presented below is intended to be interpreted in its broadest reasonable manner, even though it is being used in conjunction with a detailed description of certain specific embodiments of the disclosure. Certain terms can even be emphasized below; however, any terminology intended to be interpreted in any restricted manner will be overtly and specifically defined as such in this Detailed Description section.

The accompanying Figures depict embodiments of the present technology and are not intended to be limiting of its scope. The sizes of various depicted elements are not necessarily drawn to scale, and these various elements can be arbitrarily enlarged to improve legibility. Component details can be abstracted in the Figures to exclude details such as position of components and certain precise connections between such components when such details are unnecessary for a complete understanding of how to make and use the present technology. Many of the details, dimensions, angles, and other features shown in the Figures are merely illustrative of particular embodiments of the disclosure. Accordingly, other embodiments can have other details, dimensions, angles, and features without departing from the spirit or scope of the present technology.

When used with reference to an aortic repair device, the term "distal" can reference a portion of the aortic repair device positioned and/or configured to be positioned farther from the heart and downstream in the path of blood flow, while the term "proximal" can reference a portion of the aortic repair device positioned and/or configured to be positioned closer to the heart and upstream in the path of blood flow. In contrast, when used with reference to a catheter subsystem or delivery procedure for delivering an aortic repair device, the term "proximal" can reference a portion of the catheter system closer to an operator and/or handle (e.g., a trailing end) and/or movement in a direction closer to the operator and/or handle. The term "distal" can reference a portion of the catheter system farther from the operator and/or handle (e.g., a leading end) and/or movement in a direction farther away from the operator and/or handle. Accordingly, as set forth below, often a distal portion of a delivery tool is farther from the operator and/or handle of a catheter system than a proximal portion of the delivery tool. Likewise, often a proximal portion of the delivery tool is closer to the operator and/or handle of the catheter system than the distal portion.

Also, as used herein, the designations "rearward," "forward," "upward," "downward," etc., are not meant to limit the referenced component to use in a specific orientation. It will be appreciated that such designations refer to the orientation of the referenced component as illustrated in the Figures; the systems of the present technology can be used in any orientation suitable to the user.

The headings provided herein are for convenience only and should not be construed as limiting the subject matter disclosed.

I. OVERVIEW

Figure 1B:
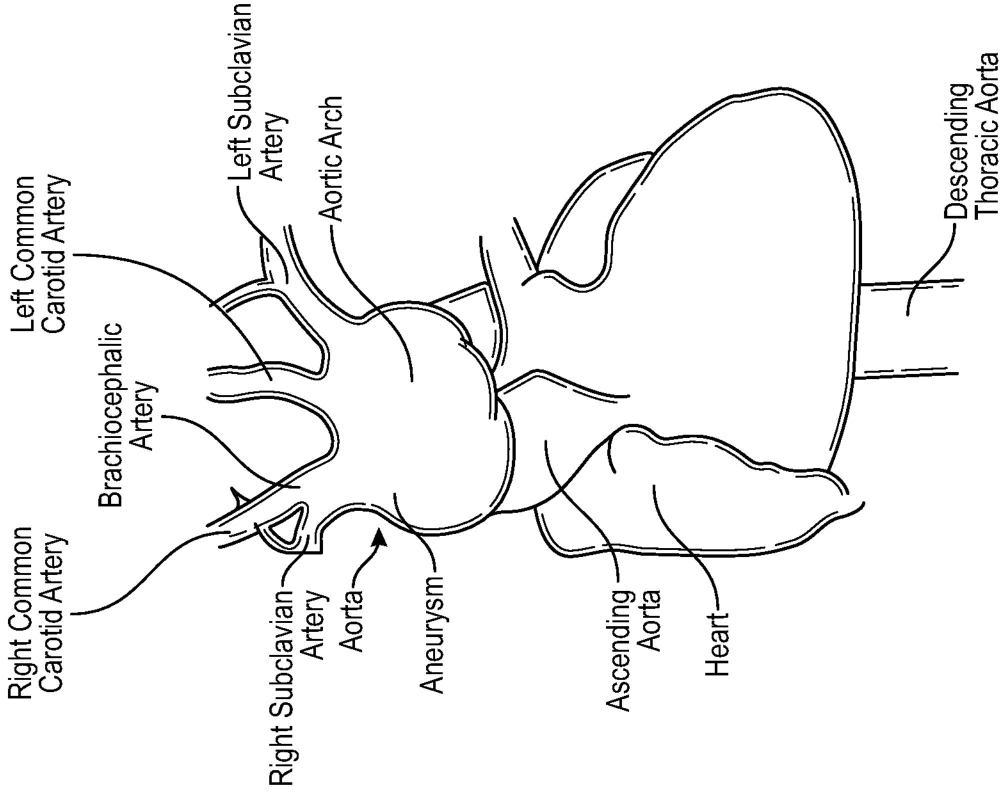

FIGS. 1A and 1B are side views of a diseased aorta and surrounding anatomy in which an aortic repair device can be implanted in accordance with embodiments of the present technology. Referring to FIGS. 1A and 1B together, the aorta is the largest vessel in the human body and carries oxygenated blood away from the left ventricle and the aortic valve of the heart for circulation to all parts of the body. The aorta is divided into different segments including the ascending aorta (which extends from the left ventricle), the aortic arch, and the descending aorta. The ascending aorta and the aortic arch can together be referred to as the "proximal aorta." The aorta includes branches into several supra-aortic arteries included the brachiocephalic artery, the left common carotid artery, and the left subclavian artery—each of which extends from the aortic arch. The brachiocephalic artery is the first branch of the aortic arch and feeds blood to the right common carotid artery and the right subclavian artery for supply to the right arm, head, and neck. It is also known as the innominate artery or the brachiocephalic trunk. The left common carotid artery is the second branch of the aortic arch and feeds blood to the left head and neck. The left subclavian artery is the third branch of the aortic arch and feeds blood to the left arm.

The diseased aorta includes an aneurysm in the ascending aorta in FIG. 1A and an aneurysm in the aortic arch in FIG. 1B. Aortic aneurysms are enlargements (e.g., dilations) of the aorta that weaken the aorta and increase the likelihood of rupture. Most people with aortic aneurysms do not have symptoms until the aorta ruptures, and the mortality rate after an aortic aneurysm rupture can exceed 90%. Often, aortic aneurysms are detected during routine medical testing such as chest X-rays, computed tomography (CT) imaging, ultrasound imaging of the heart, magnetic resonance imaging (MRI), and the like.

Figure 2A:
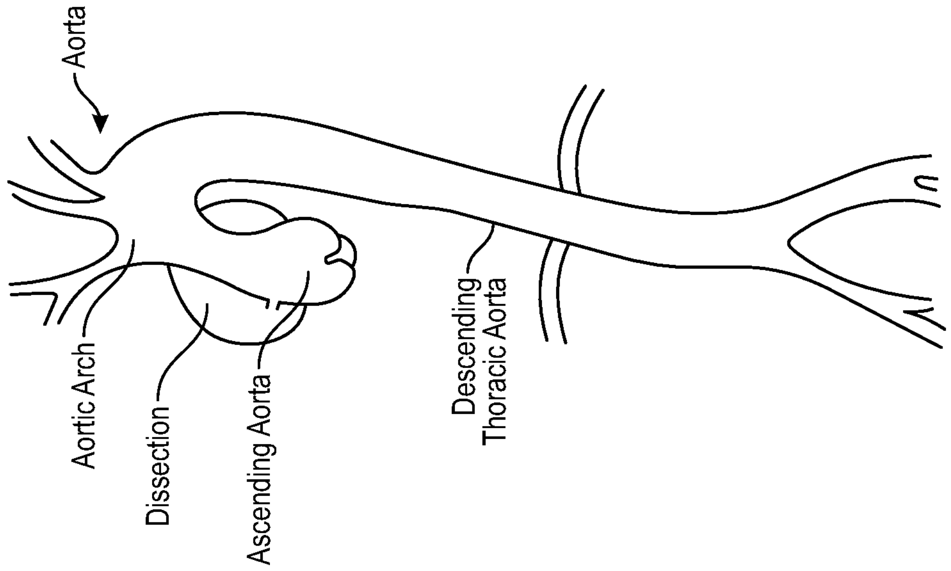
FIGS. 2A-2D are side cross-sectional views of a diseased aorta in which an aortic repair device can be implanted in accordance with embodiments of the present technology.
Figure 2B:
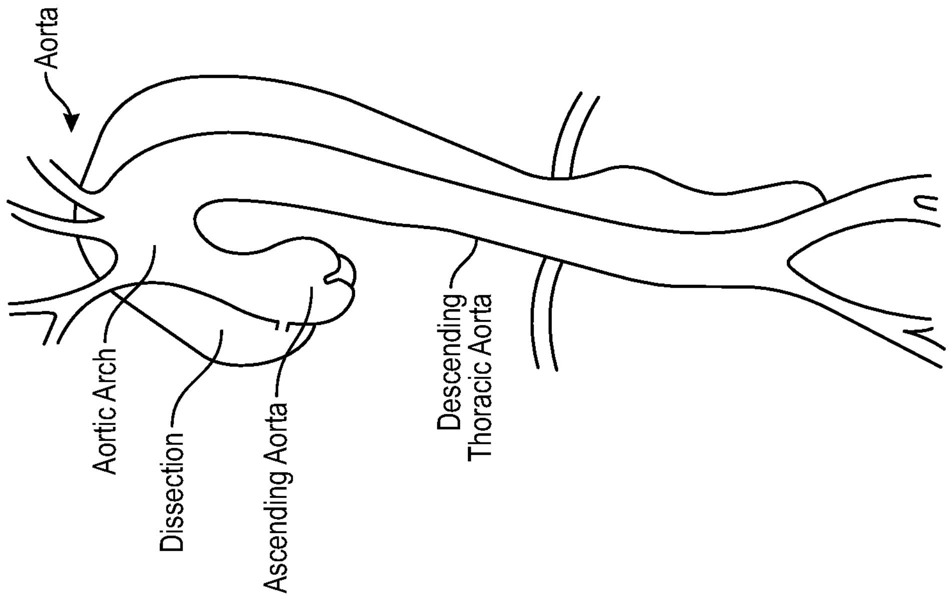
Figure 2C:
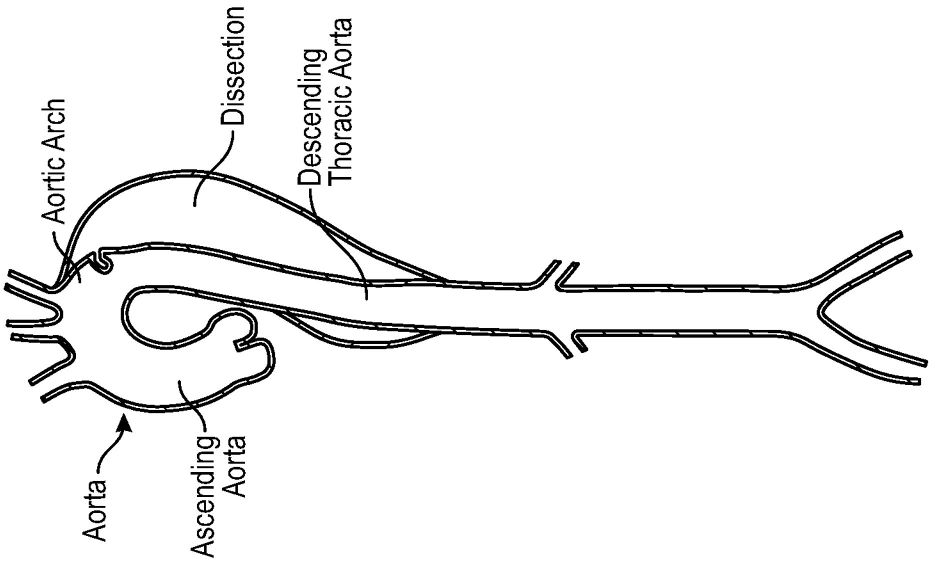
Figure 2D:
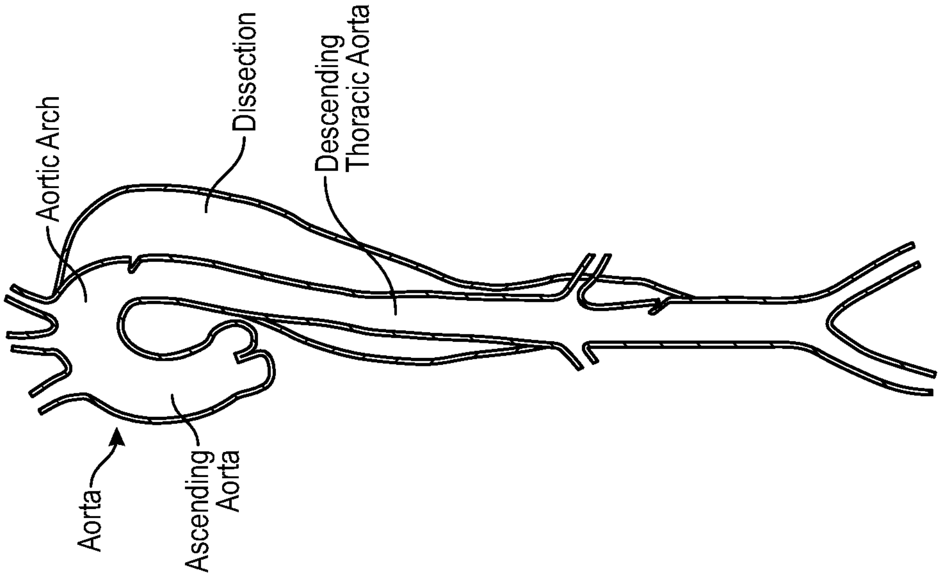

FIGS. 2A-2D are side cross-sectional views of a diseased aorta in which an aortic repair device can be implanted in accordance with embodiments of the present technology. The diseased aorta includes a smaller Type A aortic dissection in FIG. 2A, and a larger Type A aortic dissection in FIG. 2B. Aortic dissections are tears of the intimal layer of the aorta that cause blood to dissect one or more of the layers of the vessel wall and potentially leading to blocked flow or vessel rupture. Type A aortic dissections originate in the proximal aorta (e.g., the ascending aorta) and can progressively extend from the ascending aorta, along the aortic arch, and/or down along the descending aorta as shown in FIG. 2A. Aortic dissections can be acute or chronic, with acute aortic dissections frequently causing a sudden onset of severe pain in the chest, back, and/or abdomen. Most acute aortic dissections require emergency surgery, and present about a 1% risk of death every hour for the first two days after dissection—meaning that urgent diagnosis and surgery are critical for patient treatment.

Referring to FIGS. 1A-2D together, aspects of the present technology are directed to aortic repair devices that can be implanted within the aorta to treat an aortic aneurysm, a Type A aortic dissection, a Type B aortic dissection, and/or other types of diseased states. In some embodiments, an aortic repair device can span across the origin of an aneurysm or dissection and provide one or more flow conduits for diverting blood flow away from and/or past the diseased portion. In some embodiments, an aortic repair device can span between and provide one or more flow conduits for directing blood flow between the aorta and one or more branching arteries.

II. SELECTED EMBODIMENTS OF AORTIC REPAIR DEVICES

Figure 3B:
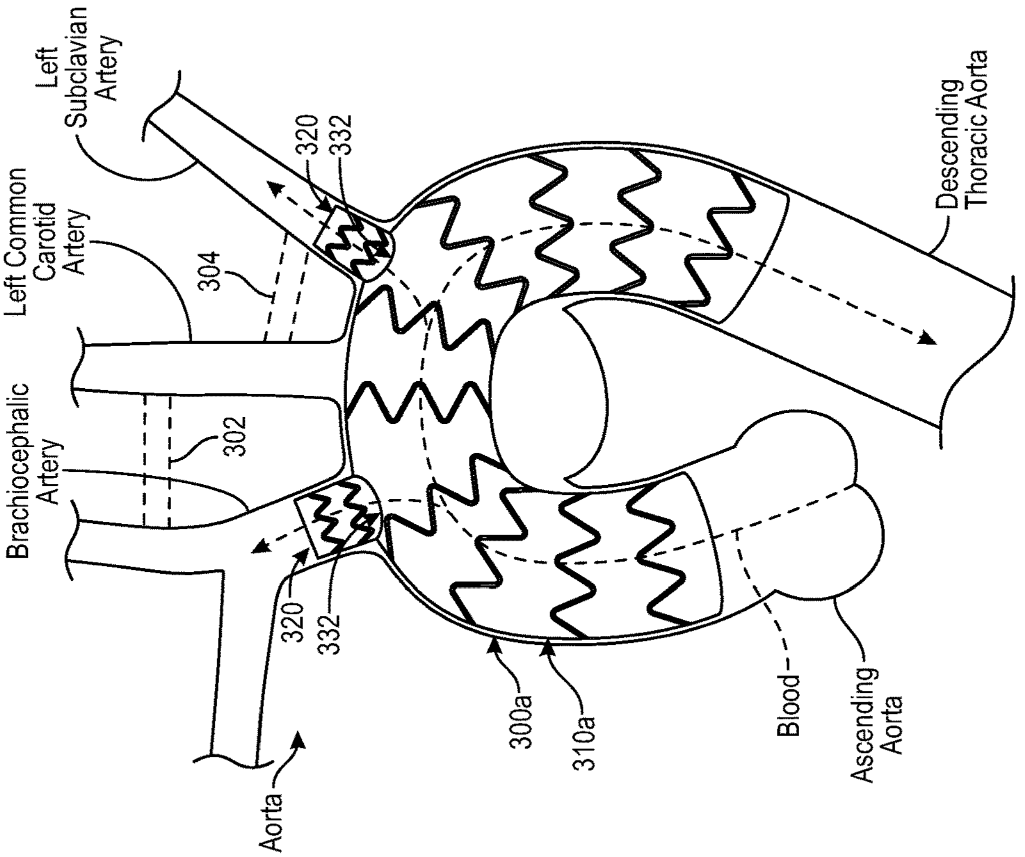
FIGS. 3A and 3B are side views of an aortic repair device before and after fenestration of a base member, respectively, positioned in an aortic arch in accordance with embodiments of the present technology.
Figure 3A:
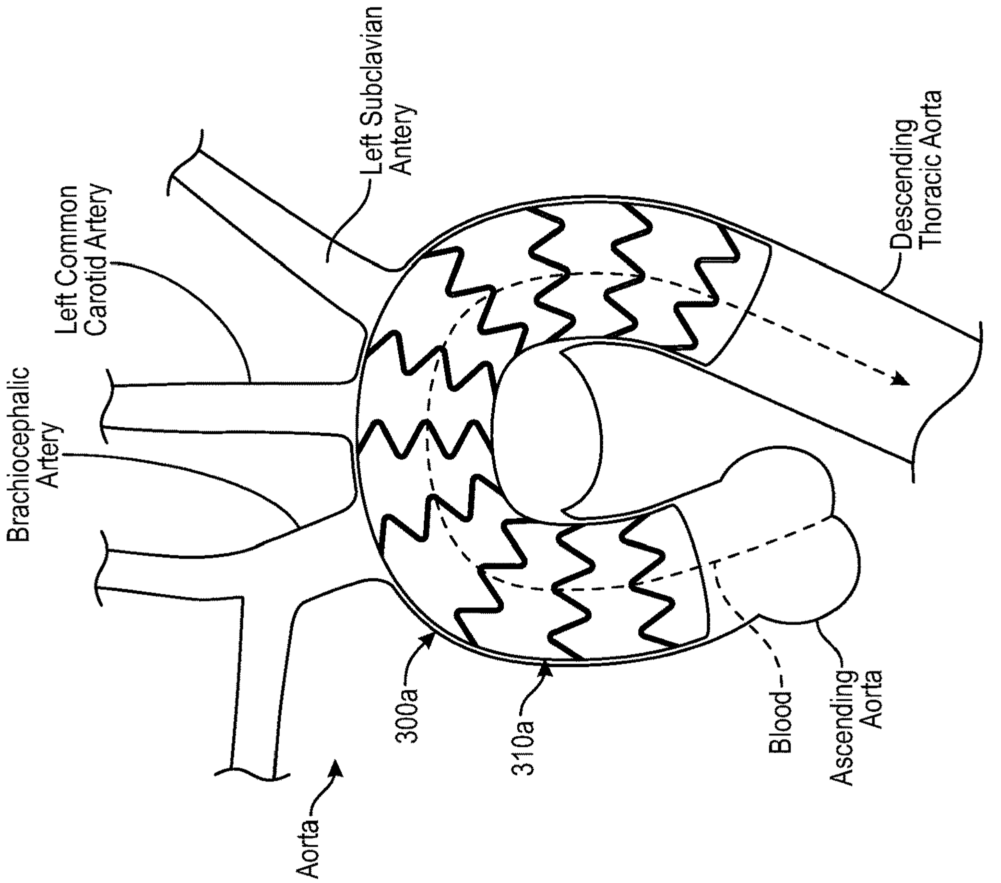

FIGS. 3A and 3B are side views of an aortic repair device 300*a* (which can also be referred to as a device, an aortic prosthesis, an aortic treatment device, an aortic implant, and/or the like) before and after fenestration of a base member 310*a*, respectively, positioned in a diseased aorta in accordance with embodiments of the present technology. The device 300*a* can be used to treat an aortic aneurysm and/or dissection that extends along at least a portion of the aortic arch. The device 300*a* can include the base member 310*a* made from a stent structure (also referred to as a "stent" or "stent frame") and a graft material. The base member 310*a* can be positioned across a diseased portion of the aorta, extending proximal and distal to an aortic dissection and/or aneurysm, to block blood flow into the diseased portion by diverting the blood flow through the base member 310*a*. When the diseased portion of the aorta is along the aortic arch, the base member 310*a* may extend across one or more aortic branch vessels. As shown in FIG. 3A, for example, the base member 310*a* diverts blood flow (shown using the dashed-line arrow) from the ascending aorta to the descending thoracic aorta, and thereby extends across the inlets of the brachiocephalic artery, the left common carotid artery, and the left subclavian artery. Accordingly, as shown in FIG. 3B, the base member 310*a* can be coupled to one or more branch members 320 (e.g., stent grafts) positioned in one or more corresponding branch vessels so as to allow the device 300*a* to perfuse one or more of the aortic branch vessels. Each of the branch members 320 can be aligned with and received at least partially within a corresponding fenestration 332 (e.g., an opening, an aperture) along a sidewall of the base member 310*a*. In the illustrated embodiment, for example, the device 300*a* includes two branch members 320 extending through two corresponding fenestrations 332 such that the device perfuses the brachiocephalic artery and the left subclavian artery, respectively. In some embodiments, one or more bypass devices, such as stents and/or harvested autologous vessels, (identified in FIGS. 3A and 3B as a first bypass device 302 and a second bypass device 304) can be implanted to extend from perfused branch vessel (e.g., the brachiocephalic artery, the right common carotid artery, the left subclavian artery, and/or the left common carotid artery) to a non-perfused branch vessel (e.g., the brachiocephalic artery, the right common carotid artery, the left subclavian artery, and/or the left common carotid artery) to provide for perfusion of all branch vessels extending from the base member 310*a*. In some embodiments, the aortic repair device 300*a* can include one, two, or more branch members 320 coupled to the base member 310*a* and configured (e.g., sized, shaped, positioned) to perfuse various branch vessels extending from the region of the aorta bypassed by the base member 310*a*.

Figure 3D:
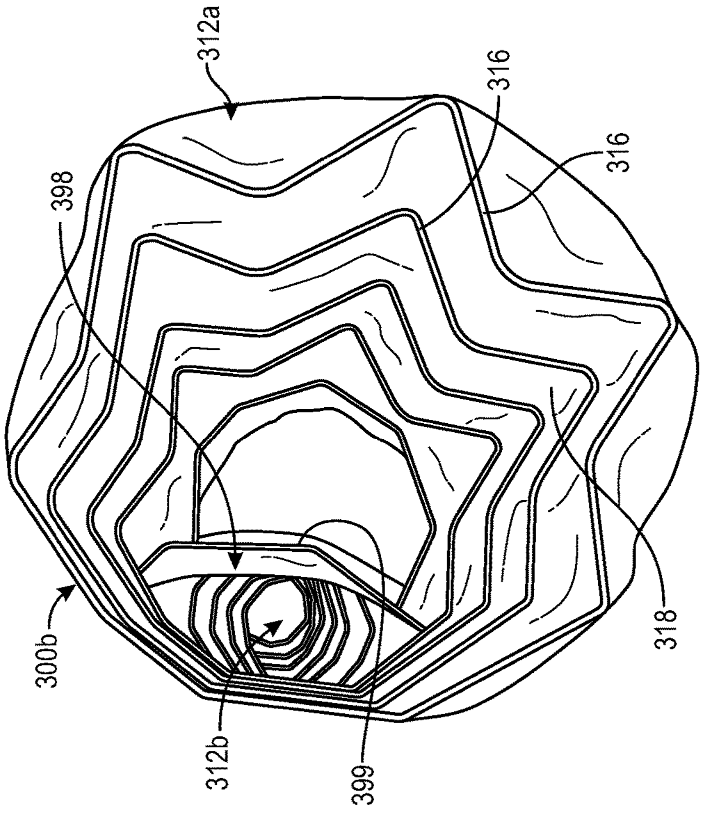
FIG. 3D is an end view of the aortic arch repair device of FIG. 3C.
Figure 3C:
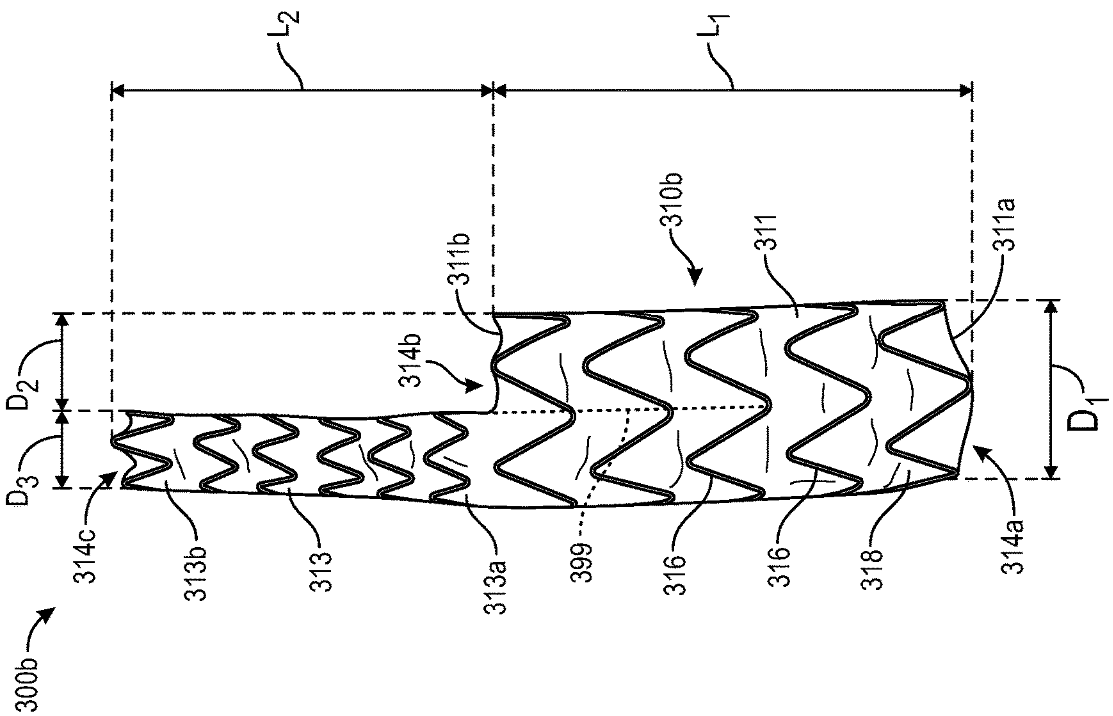
FIG. 3C is a side view of an aortic arch repair device configured in accordance with additional embodiments of the present technology.

FIGS. 3C and 3D are side and end views, respectively, of an aortic repair device 300*b* (which can also be referred to as an aortic prosthesis, an aortic treatment device, an aortic implant, and/or the like) configured in accordance with embodiments of the present technology. The aortic repair device 300*b* comprises a base member 310*b* sized and shaped for implantation at or near a diseased portion of an aorta (e.g., near or across an aneurysm or aortic dissection). The base member 310*b* includes a tubular body 311 (also referred to as a main body) and a tubular leg 313 extending distally from the body 311. More specifically, the body 311 includes a proximal (e.g., first, leading) end portion 311*a* defining a proximal (e.g., first, leading) terminus of the base member 310*b* and a distal (e.g., second, trailing) end portion 311*b*. The leg 313 includes a proximal (e.g., first, leading) end portion 313*a* coupled to and/or integrally extending from the distal end portion 311*b* of the body 311 and a distal (e.g., second, trailing) end portion 313*b* defining a distal (e.g., second, trailing) terminus of the base member 310. In the illustrated embodiment, the body 311 has a first length $L_1$ (FIG. 3C) and the leg 313 as a second length $L_2$ (FIG. 3C) less than the first length $L_1$. In some embodiments, the second length $L_2$ is the same as or greater than the first length $L_1$. In some embodiments, the first length $L_1$ can be between about 20-120 millimeters and the second length $L_2$ can be between about 20-120 millimeters.

Referring to FIGS. 3C and 3D together, the base member 310*b* can be generally hollow and define one or more lumens (e.g., flow conduits) therethrough. In the illustrated embodiment, the base member 310*b* includes: (i) a proximal opening 314*a* (e.g., a fluid opening, a first opening, a first body fluid opening, an inlet, and/or the like) at the proximal end portion 311*a* of the body 311 and having a first dimension (e.g., width, diameter, etc.) $D_1$ (FIG. 3C); (ii) a distal body opening 314*b* (e.g., a fluid opening, a second opening, a second body fluid opening, a distal body outlet, and/or the like) at the distal end portion 311*b* of the body 311 and having a second dimension (e.g., width, diameter, etc.) $D_2$ (FIG. 3C); and (iii) a distal leg opening 314*c* (e.g., a fluid opening, a third opening, a leg fluid opening, a distal leg outlet, and/or the like) at the distal end portion 313*b* of the leg 313 and having a third dimension (e.g., width, diameter, etc.) $D_3$ (FIG. 3C). The first dimension $D_1$, which generally corresponds to the outer dimension (e.g., diameter) of the body 311, is larger than the second and third dimensions $D_2$, $D_3$ and can be sized to generally match or be larger than (e.g., oversized relative to) the diameter of a patient's aorta (e.g., between about 20-60 millimeters, between about 26-54 millimeters, about 40 millimeters). The third dimension $D_3$, which generally corresponds to the outer diameter of the leg 313, can be sized to generally match or be larger than a branch vessel of the patient's aorta, such as the brachiocephalic artery (e.g., between about 10-22 millimeters, about 16 millimeters). In some embodiments, the second dimension $D_2$ can be larger than the third dimension $D_3$.

As shown in FIG. 3D, the base member 310 further includes a septum 399 (e.g., a flow divider) positioned within and dividing the body 311 into a primary lumen 312*a* (e.g., a first lumen) and a branch or secondary lumen 312*b* (e.g., a second lumen). In the illustrated embodiment, the septum 399 extends from the distal end portion 311*b* of the body 311, along a portion of the body 311, and terminates at an intermediate position between the proximal and distal end portions 311*a* (e.g., set back from the proximal terminus of the body 311). In some embodiments, the septum 399 extends along the entire length of the body 311 between the proximal and distal end portions 311*a*, 311*b*. In some embodiments, the septum 399 is centered within the body 311 such that the septum 399 extends along the first diameter $D_1$ and the primary and secondary lumens 312*a*, 312*b* have the same size (e.g., cross-sectional area, volume) within the body 311. In other embodiments, the septum 399 can be offset within the body 311 such that the primary and secondary lumens 312*a*, 312*b* have different sizes (e.g., different cross-sectional areas, volumes, diameters). For example, the secondary lumen 312*b* can be smaller than the primary lumen 312*a*. In yet other embodiments described below, the body 311 can include multiple septa that divide the body into more than two lumens.

The primary lumen 312*a* can extend from and define a flow path (e.g., conduit) between the proximal opening 314*a* and the body opening 314*b*, whereas the secondary lumen 312*b* can extend from and define a flow path between an opening 398 at the terminus of the septum 399 and the leg opening 314*c*. As shown in FIG. 3D, the primary lumen 312*a* have a D-like cross-sectional shape within the body 311 as the septum 399 bifurcates the overall lumen defined by the body 311. The secondary lumen 312*b* can have a generally circular cross-sectional shape within the leg 313 and a circular, elliptical, or D-like cross-sectional shape along the length of the body 311.

In some embodiments, the base member 310 is an expandable stent graft comprising one or more stents 316 coupled to a graft material 318. The stents 316 can comprise one or multiple interconnected struts and can also be referred to as a stent structure. The body 311 and the leg 313 can be integrally formed as part of the same stent graft, or can be separate components that are releasably or permanently coupled together. The graft material 318 can comprise fabric, woven polyester, polytetrafluoroethylene, polyurethane, silicone, and/or other suitable materials known in the art of stent grafts, and is configured to inhibit or even prevent blood flow therethrough. In some embodiments, the septum 399 comprises the same material as the graft material 318 or another type of graft material. Accordingly, the graft material 318 and the septum 399 can define and enclose the primary lumen 312*a* and the secondary lumen 312*b* and are configured to maintain blood flowing along the flow paths defined thereby. In some embodiments the septum 399 can comprise a non-graft material, such as a metal mesh that is permeable to blood. In some such embodiments, the aortic repair device 300*b* can include one or more sealing features positioned proximate the distal end portion 311*b* of the body 311.

The stents 316 can extend circumferentially to define the tubular shape of the body 311 and the leg 313 and can be interconnected or separate. In some embodiments, the stents 316 have the illustrated V-pattern shape (e.g., including alternating proximal and distal apices). In some embodiments, the stents 316 are Z-stents, laser-cut stents, and/or other types of self-expanding and/or balloon-expandable stents. The stents 316 can be coupled to an outer surface of the graft material 318 as shown in FIGS. 3C and 3D via stitching and/or suitable techniques, and/or can be coupled to an inner surface of the graft material 318. The stents 316 can be configured to self-expand and, accordingly, can be formed from a shape memory material, such as nickel-titanium alloy (nitinol). In other embodiments, the shape of the stents 316, the number of the stents 316, and/or the arrangement of the stents 316 can be varied.

Figure 3E:
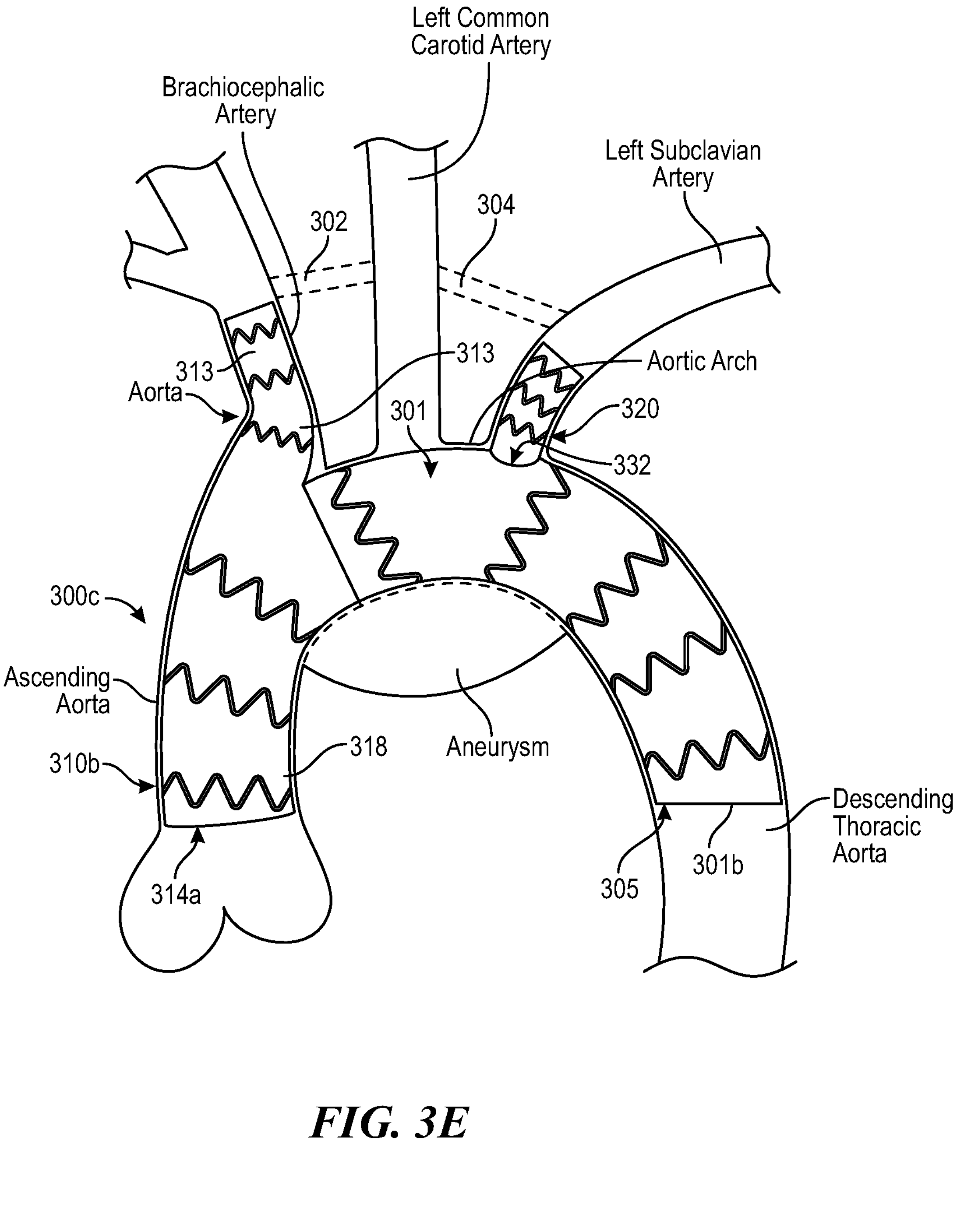
FIGS. 3E and 3F are sides views of the aortic arch repair device of FIG. 3C implanted in an aortic arch and coupled to a spanning member in accordance with embodiments of the present technology.

FIG. 3E is a side view of an aortic repair system 300*c* implanted within an aorta in accordance with embodiments of the present technology. The aortic repair system 300*c* includes the base member 310*b* of FIGS. 3C and 3D, a spanning member 301, and the branch member 320. In some embodiments, the aorta can include an aneurysm, dissection, and/or other diseased portion as described in detail above with reference to FIGS. 1A-2D. In the illustrated embodiment, the body 311 of the base member 310*b* is implanted within the proximal aorta (e.g., the ascending aorta and/or the aortic arch) with the proximal end portion 311*a* positioned proximate to the aortic valve, and the leg 313 extends from the body 311 to the brachiocephalic artery where the distal end portion 313*b* is positioned. Referring to FIGS. 3C-3E together, the stents 316 can expand the graft material 318 into contact with the inner wall of the aorta and/or the brachiocephalic artery to provide a seal between the vessel and the base member 310. More particularly, the body 311 can sealingly contact the inner wall of the proximal aorta such that all or substantially all blood flow through the aorta enters the proximal opening 314*a* and flows through either the primary lumen 312*a* or the secondary lumen 312*b*. As shown in FIG. 3E, the base member 310*b* can direct the blood flow (i) through the primary lumen 312*a* and out of the body opening 314*b* into the aorta to perfuse the aorta and (ii) through the secondary lumen 312*b* and out of the leg opening 314*c* into the brachiocephalic artery to perfuse the brachiocephalic artery.

In some aspects of the present technology, the base member 310*b* can be positioned against/adjacent to a diseased portion of the aorta, such as the origin of a dissection and/or aneurysm, to block blood flow into the diseased portion by diverting the blood flow through the base member 310*b* and past the diseased portion. In additional aspects of the present technology, the entire outer surface of the body 311 has a tubular shape configured to engage and seal with the inner wall of the aorta. That is, the body 311 can provide a relatively long sealing region along all or substantially all of the first length $L_1$.

The base member 310*b* can be delivered to the aorta in a collapsed configuration within a catheter system (not shown). The catheter system can access the aorta via any suitable intravascular path—such as an aortic approach, a transfemoral approach, a transcarotid approach, a transsubclavian approach, transapical approach, and so on.

In some embodiments, other implantable devices can be modularly coupled to the base member 310*b* during the same or a different surgical/interventional procedure. For example, the length $L_2$ of the leg 313 can be relatively short such that the distal end portion 313*b* of the leg 313 is positioned in the aorta, and a separate tubular stent graft or other implant can be coupled to the leg 313 and extend into the brachiocephalic artery or another branch vessel. Likewise, a separate tubular stent graft or other implant can be coupled to the body 311 and extend farther through the aorta and/or to a branch vessel.

As described in detail below, in some embodiments the base member 310*b* can be implanted within the descending aorta in a reversed or flipped orientation. Accordingly, in a flipped orientation, the "distal" portions of the base member 310*b* are instead "proximal" portions of the base member 310*b* and vice versa. Therefore, one of ordinary skill in the art will understand that the use of the terms "proximal" and "distal" can be based on the orientation of the base member 310*b* or can refer to the corresponding structure of the base member 310*b* (i.e., the "distal" and "proximal" portions can refer to the corresponding structure of the base member 310*b* described in detail herein regardless of the actual orientation of the base member 310*b* within the aorta). Likewise, the terms "distal" and "proximal" can be substituted with the terms "first" and "second," "leading" and "trailing," and/or the like.

The spanning member 301 can be coupled to (e.g., attached to, docked to) the base member 310*b*, have a tubular shape defining one or more lumens (e.g., flow conduits) therethrough, and can include features generally similar to those of the base member 310*b*. For example, in some embodiments the spanning member 301 is an expandable stent graft comprising one or more struts or stent 306 and a graft material 308 coupled to the stent 306. In the illustrated embodiment, the spanning member 301 includes a proximal end portion 301*a* (e.g., a first end portion, a leading end portion, and/or the like; partially obscured by the base member 310*b*) defining a proximal terminus of the spanning member 301 and a distal end portion 301*b* (e.g., .g., a second end portion, a trailing end portion, and/or the like) defining a distal terminus of the spanning member 301. The proximal end portion 301*a* can further define a proximal opening (e.g., a fluid opening, a first spanning fluid opening, a leading spanning fluid opening, and/or the like) obscured by the base member 310*b* and the distal end portion 301*b* can further define a distal opening 305 (e.g., a fluid opening, a second spanning fluid opening, a trailing spanning fluid opening, and/or the like).

Referring to FIGS. 3C-3E together, the proximal end portion 301*a* of the spanning member 301 is at least partially positioned within the body 311 within the primary lumen 312*a* and can sealingly engage the body 311 within the primary lumen 312*a* to define a continuous blood flow path from the proximal opening 314*a* of the base member 310*b*, through the primary lumen 312*a*, and through the lumen of the spanning member 301 to the distal opening 305. That is, the graft material 308 of the spanning member 301 can sealingly engage the septum 399 and the graft material 318 of the base member 310*b* within the primary lumen 312*a* such that blood flow is routed through the primary lumen 312*a* to the lumen of the spanning member 301. In some aspects of the present technology, because the septum 399 extends the entire length of the body 311, the septum 399 provides a docking or sealing region for engaging the spanning member 301 along the entire length of the primary lumen 312*a*. In some embodiments, at least a portion of the spanning member 301 (e.g., the distal end portion 301*b*) sealingly engages the aorta within the aortic arch and/or the descending thoracic aorta. Accordingly, the aortic repair system 300*b* can direct blood flow through the secondary lumen 312*b* to the brachiocephalic artery and through the primary lumen 312*a* and the spanning member 301 to the descending thoracic aorta.

When implanted, the aortic repair system 300*b* can divert blood flow past a diseased portion of the aorta, such an aneurysm in the aortic arch shown in FIG. 3E. In some embodiments, the spanning member 301 can be delivered to the aorta in a collapsed configuration within a catheter system (not shown) in the same or a separate procedure as the base member 310*b*. For example, often a patient may initially only need treatment within the ascending aorta and/or the aortic arch to treat an initial dissection or aneurysm but, at a later time (e.g., months or years later), may require additional treatment of the aortic arch and/or the descending thoracic aorta as the diseased state progresses. Accordingly, the base member 310*b* can be implanted during an initial procedure and the spanning member 301 can be implanted during a later procedure and modularly coupled to the base member 310*b* to provide further treatment of the aortic arch and/or the descending thoracic aorta (e.g., by bypassing blood flow past the aneurysm shown in FIGS. 3A and 3B).

Referring to FIG. 3E, the spanning member 301 bypasses the left common carotid artery and the left subclavian artery and thus may partially or fully occlude those vessels. In some embodiments, the bypass 302 between the perfused right common carotid artery and/or the bypass 304 between the left common carotid artery and the left subclavian artery (and/or between the right common carotid artery and the left subclavian artery) can be surgically created to perfuse those vessels. In other embodiments described in detail below, the aortic repair system 300*c* can include additional implantable devices (e.g., stent grafts) coupled to the spanning member 301 and/or the base member 310*b* that are configured (e.g., sized, shaped, positioned) to perfuse different branch vessels.

In some embodiments, the spanning member 301 can be fenestrated to perfuse one or both of the left subclavian artery and the left common carotid artery. For example, as shown in FIG. 3E, the branch member 320 is positioned to perfuse the left subclavian artery and coupled (e.g., mechanically and/or fluidly coupled) to the spanning member 301 via the fenestration 332. The fenestration 332 can be pre-formed, formed ex vivo (e.g., before implanting the spanning member 301), or formed in vivo (e.g., during and/or after implanting the spanning member). In other embodiments, the branch member 320 or an additional branch member can be positioned to perfuse the left common carotid artery and coupled to the spanning member 301 via another fenestration. In these and/or other embodiments, the fenestration 332 can be formed in the leg 313 of the base member 310*b*, or in another suitable portion of the base member.

Figure 3F:
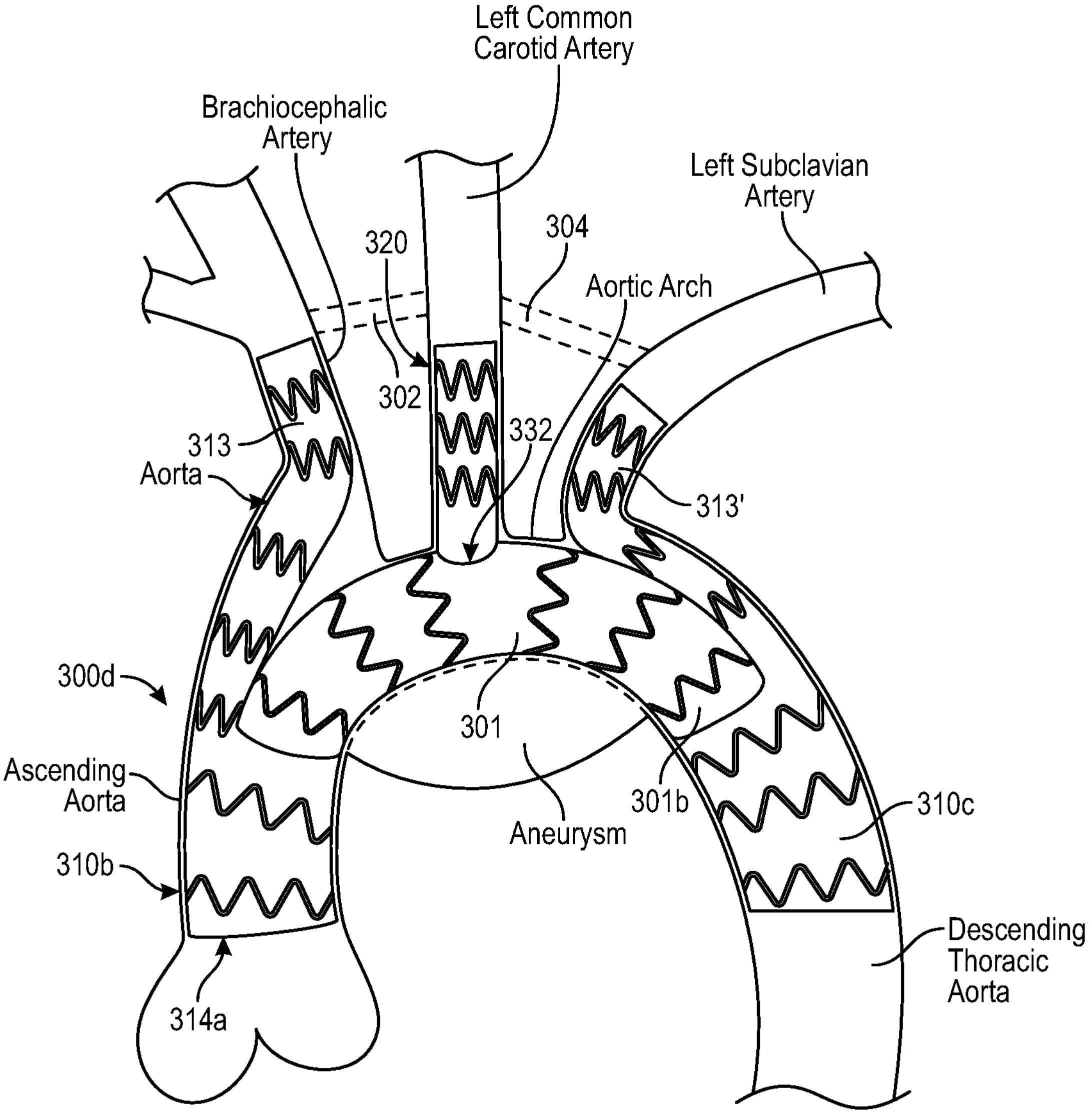

FIG. 3F is a side view of an aortic repair system 300*d* implanted within an aorta in accordance with embodiments of the present technology. In the illustrated embodiment, the aortic repair system 300*d* includes the base member 310*b* described in detail above with reference to FIGS. 3C-3E (identified as first base member 310*b*) and the spanning member 301 coupled to (e.g., attached to, docked to) the first base member 310*b*. In the illustrated embodiment, the aortic repair device 300*d* further includes a second base member 310*c* (which can be identical or substantially identical to the first base member 310*b*) implanted at least partially within the descending thoracic aorta. The spanning member 301 spans from the first base member 310*b* and is coupled to the second base member 310*c*. Specifically, with reference to FIGS. 3C-3F together, the distal end portion 301*b* of the spanning member 301 can be positioned within the body 311 within the primary lumen 312*a* of the second base member 310*c* and can sealingly engage the body 311 within the primary lumen 312*a* to define a continuous blood flow path from the spanning member 301 through the primary lumen 312*a*, and out of the proximal opening 314*a* of the second base member 310*c*. The leg 313' of the second base member 310*c* can extend into a second branch artery (e.g., the left subclavian artery) for perfusing the second branch artery. For example, the second base member 310*c* can receive retrograde blood flow through the trailing opening 314*a* for perfusing the second branch artery. Alternatively or additionally, the secondary lumen 312*b* of the second base member 310*c* can be perfused via the primary lumen 312*a* where the septum 399 extends only partially from the leading end portion 311*b* toward the trailing end portion 311*a*. That is, blood flow from the spanning member 301 can flow into the primary lumen 312*a* within the body 311 and around the septum 399 into the secondary lumen 312*b* where the septum 399 terminates within the body 311. In some aspects of the present technology, the aortic repair system 300*d* can provide for a full arch treatment in which (i) the leg 313 of the first base member 310*b* directs blood flow to a first branch artery (e.g., the brachiocephalic artery), (ii) the leg 313' of the second base member 310*c* directs blood flow to a second branch artery (e.g., the left subclavian artery), (iii) a third branch artery (e.g., the left common carotid artery) is perfused via bypass 302 and/or 304, and (iv) the primary lumens of the first and second base members 310*b-c* and the spanning member 301 collectively direct blood flow to the descending thoracic aorta.

In some embodiments, the spanning member 301 can be fenestrated to perfuse one of the left subclavian artery and the left common carotid artery. For example, as shown in FIG. 3F, the branch member 320 is positioned to perfuse the left common carotid artery and coupled (e.g., mechanically and/or fluidly coupled) to the spanning member 301 via the fenestration 332. The fenestration 332 can be pre-formed, formed ex vivo (e.g., before implanting the spanning member 301), or formed in vivo (e.g., during and/or after implanting the spanning member). In these and/or other embodiments, the fenestration 332 can be formed in the leg 313 of the first base member 310*b*, the leg 313' of the third base member 310*c*, or in another suitable portion of either of the base members 31*b-c*.

Additional details regarding aortic repair devices, base members, branch members, and fenestration forming techniques are described in detail below with reference to FIGS. 4A-34C.

III. SELECTED EMBODIMENTS OF BASE MEMBERS

FIGS. 4A-7 illustrate base members of aortic repair devices configured in accordance with embodiments of the present technology. The various base members can include some features that are at least generally similar or identical in structure and/or function to one another and/or to the corresponding features of one or more of the base members 310*a-c* described above with reference to FIGS. 3A-3F. Additionally, or alternatively, at least some of the various base members can operate in a generally similar or identical manner to one another and/or to one or more of the base members 310*a-c*. In these and other embodiments, one or more of the different features of the base members of the present technology can be combined and/or omitted.

FIGS. 4A-4E are side perspective views of respective base members 410*a-e* (referred to collectively as "base members 410") configured in accordance with embodiments of the present technology. Each of the base members 410 include a first (e.g., proximal) end portion 410$a_1$-$e_1$ with a first (e.g., proximal) end terminus, and a second (e.g., distal) end portion 410$a_2$-$e_2$ opposite the first end portion 410$a_1$-$e_1$ and including a second (e.g., distal) end terminus of the base member 410*a-e*. Each of the base members 410 can be generally hollow and define one or more lumens 412*a-e* (e.g., fluid conduits, flow paths, or the like) therethrough (referred to collectively as "lumen(s) 412" or "lumen 412"). Accordingly, each of the base members 410 can include (i) a first opening 414$a_1$-$e_1$ (e.g., a proximal opening, an aperture, an inlet, or the like) at the first end portion 410$a_1$-$e_1$, and (ii) a second opening 414$a_2$-$e_2$ (e.g., a distal opening, an aperture, an inlet, or the like) at the second end portion 410$a_2$-$e_2$.

In some embodiments, one or more of the base members 410 are expandable stent grafts comprising a stent structure 415*a-e* (referred to collectively as "stent structure 415" and/or as a "stent frame 415") and a graft material 418*a-e* (referred to collectively as "graft material 418") coupled to and extending at least partially around the stent structure 415. The stent structure 415 can include multiple interconnected struts or stents 416*a-e* (referred to collectively as "struts 416") that extend around a perimeter of the base member 410 to form an expandable frame. The graft material 418 can be fabric and/or other biocompatible material (e.g., woven polyester, polytetrafluoroethylene, polyurethane, silicone) that provides an impermeable barrier. The graft material 418, when supported at least in part by the stent structure 415, can define the lumen(s) 412 (i.e., an enclosed conduit) through the base member 410 and allow for blood flow therethrough.

The stent structure 415 can, in its expanded state, extend circumferentially to define the tubular shape of the base member 410. In some embodiments, the struts 416 of the stent structure 415 form a V-shaped pattern (e.g., including alternating proximal and distal apices) and/or a diamond-shaped pattern that can be interconnected with and/or spaced apart from radially adjacent rings of the stent structure 415. In some embodiments, the stent structure 415 can have a different shape, can be made from a laser cut material, can be made from a braided structure, and/or have other suitable configurations for defining a tubular structure. In these and other embodiments, the stent structure 415 can be configured to self-expand and, accordingly, can be formed from a shape memory material, such as nickel-titanium alloy (nitinol). The stent structure 415 can be coupled to an outer surface or an inner surface of the graft material 418 via stitching (e.g., sutures), adhesives, and/or suitable stent connection techniques.

The base member 410 can include one or more fenestration regions 430*a-e* (referred to collectively as the "fenestration region 430" or "fenestration regions 430") between the first end portion 410$a_1$-$e_1$ and the second end portion 410$a_2$-$e_2$. Each fenestration region 430 can include one or more pre-formed fenestrations 432*a-e* (referred to collectively as the "fenestration 432" or "fenestrations 432") and/or features that facilitate the formation of one or more openings or fenestrations through the sidewall of the base members 410. In the embodiments illustrated in FIGS. 4A-4E, for example, the base member 410 includes a first fenestration region 430$a_1$-$e_1$ with a first fenestration 432$a_1$-

$e_1$ that is pre-formed ex vivo along the sidewall of the base member 410. This fenestration 432 can be part of the original device construction or formed at another time before the device is delivered to a target site within a patient's vessel. The fenestration 432 can have a first dimension $D_1$ (e.g., a width, a diameter, a circumference, a cross-sectional area, or the like) sized and shaped to allow blood to follow from the lumen 412 into a vessel branching from a patient's aortic arch, such as the brachiocephalic artery. For example, the first dimension $D_1$ can be equal to, larger than, or slightly smaller than the base of the brachiocephalic artery (e.g., between about 10-30 millimeters, about 18 millimeters). Additionally, or alternatively, the fenestration 432 can be sized to receive a corresponding branch member that extends into an artery extending from the aortic arch and/or other portions of the aorta, such as the branch member 320 described above with respect to FIG. 3B, any of other the branch members described herein, and/or other suitable branch members. In some embodiments, one or more of the fenestration 432 can be pre-formed in the base member 410 and/or formed ex vivo, such as before delivery of the base member 410. Additionally, or alternatively one or more of the fenestrations 432 can be formed in vivo at the fenestration region 430, e.g., during and/or after delivery of the base member 410. Regardless of when the fenestrations 432 are formed, each of the fenestrations 432 can be sized to accommodate a branch member that extends into a branching vessel, and/or sized to allow blood to flow directly into a branching vessel.

The base member 410 can expand or otherwise transition from a first, low-profile state to facilitate delivery to a target site (e.g., the aortic arch) to a second, deployed state (shown in FIGS. 4A-4E). In the second state, the base member 410 is sized to engage at least a portion of the inner wall of the aorta, such a portion of the wall along the aortic arch, and affix thereto. Upon deployment of the base member 410, the fenestration region(s) 430 and/or the pre-formed fenestration 432 can be at least partially aligned with one or more of the patient's branch vessels. For example, referring to FIG. 4A, the first pre-formed fenestration 432$a_1$ of the first base member 410$a$ can be aligned with and/or otherwise configured to allow blood flow to the patient's brachiocephalic artery when the first base member 410$a$ is positioned within the patient's aortic arch. Accordingly, the single fenestration 432$a_1$ can perfuse the patient's brain during at least a portion of the implantation procedure, e.g., before and/or during the creation of one or more additional fenestrations in the first base member 410$a$, which are then used to perfuse one or more other branching arteries (e.g., the left common carotid artery, and/or left subclavian artery). This is described in greater detail below with reference to FIG. 5.

In some embodiments, the pre-formed fenestration 432 can provide the structure to maintain blood flow to at least one of the head and neck vessels during implantation of the graft(s). For example, because the pre-formed fenestration 432 is an opening through the base member 410, blood can flow through the pre-formed fenestration 432 and into one or more of the branch vessels during an implant procedure of the base member 410. In some embodiments, the pre-formed fenestration 432 may be defined by a bare stent region of the base member 410 in which the graft material does not cover a portion of the stent structure. In embodiments where the base member 410 does not have one or more pre-formed fenestrations, the device can include temporary sutures or other mechanisms to hold at least a portion of at least one end of the base member 410 away from the wall of the aorta so that blood can continues to flow to one or more branch vessels during implantation. After the fenestration and branch graft implantation process is complete, these temporary sutures or other temporary perfusion mechanisms can be removed and/or released, allowing the base member 410 to expand or otherwise lay against the aorta wall at the end, so that all blood flows through the graft. In some embodiments, the sutures and/or other temporary perfusion mechanisms can be included in conjunction with one or more pre-formed fenestrations 432.

The base member 410 can include additional fenestration regions along its sidewall in addition to or in place of the first fenestration region 430$a_1$-$e_1$, and these fenestration regions can include features that facilitate in vivo fenestration of the base member 410. For example, another fenestration can be formed at any suitable location along the base member 410$a$ of FIG. 4A, such as in the region 430$a_2$ identified in FIG. 4A. In the embodiment illustrated in FIG. 4B, the base member 410$b$ includes a second fenestration region 430$b_2$ in which a portion of the struts 416$b$ of the stent structure 415$b$ are unattached to the graft material 418$b$. More specifically, one or more of the struts 416$b$ have a first portion 416$b_1$ attached (e.g., sutured, bonded) to the graft material 418$b$ and a second portion 416$b_2$ that is unattached to the graft material 418$b$, such that each of the second portions 416$b_2$ are independently "loose," "mobile," or freely moveable relative to each other and/or the graft material 418$b$. In the illustrated embodiment, the second fenestration region 430$b_2$ includes five neighboring mobile or uncoupled strut portions 416$b_2$. In other embodiments, the second fenestration region 430$b_2$ can include more than five or fewer than five mobile strut portions 416$b_2$. The second fenestration region 430$b_2$ can have a second dimension $D_2$ (e.g., a length, a width, a diameter, a circumference, a cross-sectional area, or the like) sized to allow for the formation of one or more fenestrations. For example, the second dimension $D_2$ can be equal to or larger than an opening of at least one branch vessel of the patient's aorta, such as the left common carotid artery and/or the left subclavian artery. In the illustrated embodiment, the second dimension $D_2$ is greater than the first dimension $D_1$ such that the second fenestration region 430$b_2$ extends along a longer lateral segment of the base member 410$b$ to provide ample tolerance for alignment with different branch vessel spacings and sizes. In other embodiments, the second dimension $D_2$ can be less than or equal to the first dimension $D_1$. In these and other embodiments, the first dimension $D_1$ and/or the second dimension $D_2$ can be patient-specific, e.g., selected to correspond to the anatomy of a given patient. During an in vivo fenestration formation procedure, individual ones of the movable strut portions 416$b_2$ can be pushed, bent, or otherwise moved away from the desired fenestration site (e.g., using a fenestration tool) to expose the underlying graft material 418$b$. The fenestration can then be formed (e.g., cut) directly through the more pliable graft material without the strut portions 416$b_2$ preventing the cutting tool from penetrating the graft material 418$b$ in the second fenestration region 430$b_2$.

Figure 4A:
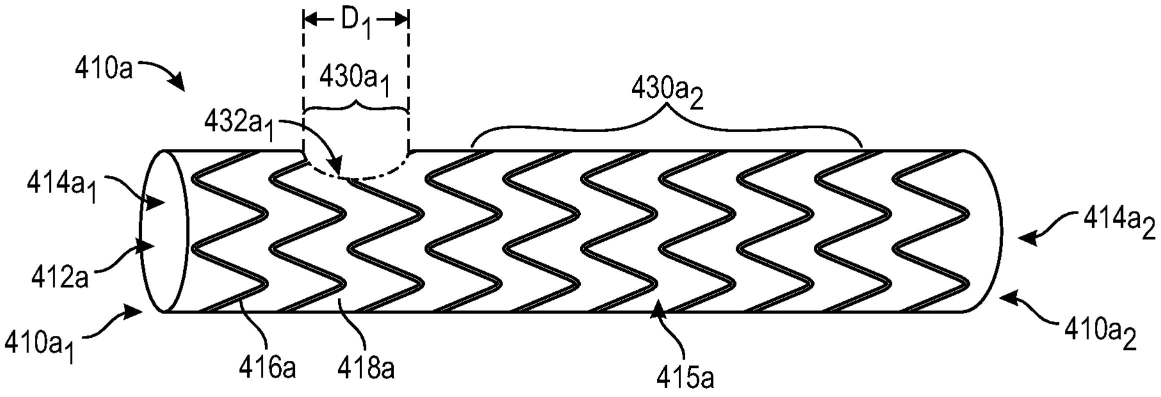
FIGS. 4A-4E are perspective views of base members of aortic repair devices configured in accordance with embodiments of the present technology.
Figure 4B:
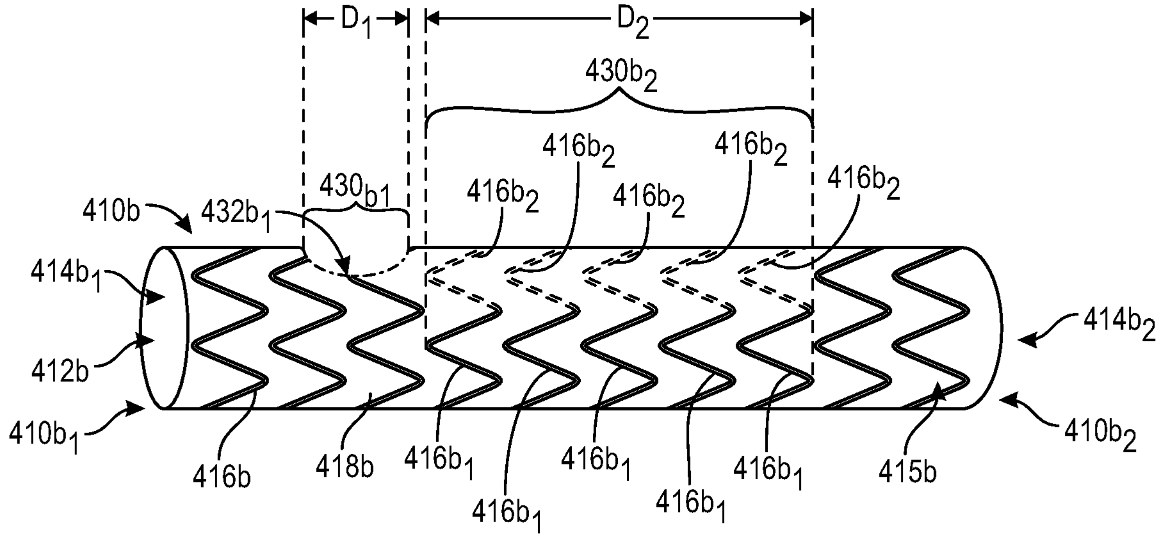
Figure 4C:
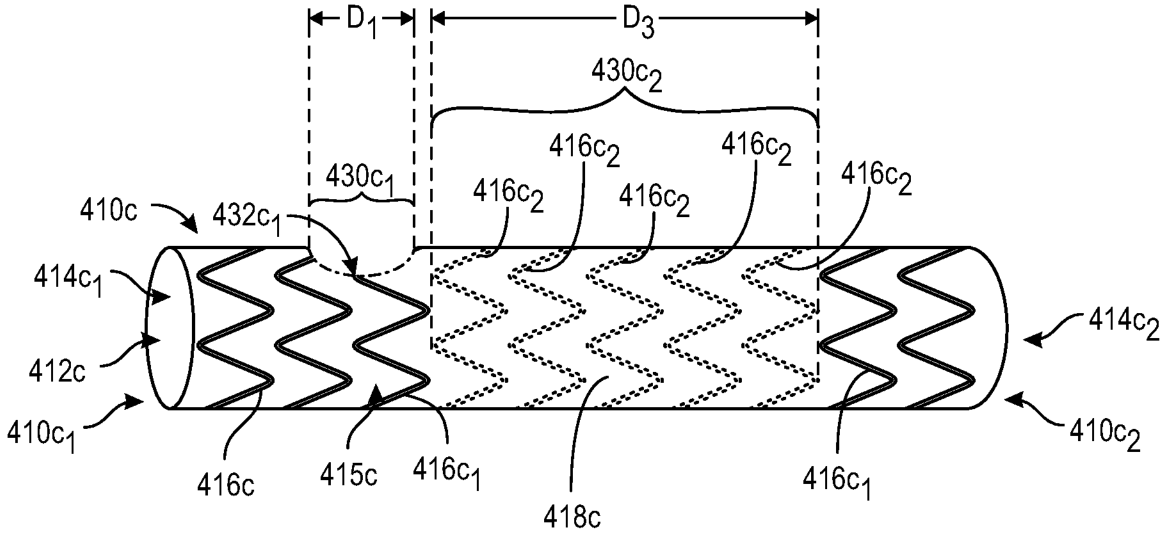

Referring to FIG. 4C, the third base member 410$c$ includes a third fenestration region 430$c_2$ including a plurality of flexible struts 416$c_2$. Individual ones of the flexible struts 416$c_2$ can have a higher frangibility, flexibility, deformability, and/or penetrability than the first struts 416$c_1$ that form the rest of the stent structure. In at least some embodiments, for example, the first struts 416$c_1$ can be made of metal and/or a shape memory material struts 416$c_2$ can be made of a non-metallic material, such as one or more polymers (e.g., polymer beads), or any other suitable non-metallic material. In the illustrated embodiment, the third fenestration region $430c_2$ includes five neighboring (e.g., adjacent) flexible struts $416c_2$. In other embodiments, the third fenestration region $430c_2$ can include more than five or fewer flexible struts $416c_2$, can be interspersed with the first, more rigid struts $416c_1$, and/or the flexible struts $416c_2$ can have other suitable arrangements. The third fenestration region $430c_2$ can have a third dimension $D_3$ (e.g., a width, a diameter, a circumference, a cross-sectional area, or the like) sized generally similar to the second dimension $D_2$ described above with respect to FIG. 4B. During an in vivo fenestration formation procedure, the flexible struts $416c_2$ can be punctured, broken, or bent by a cutting tool such that, unlike the more rigid struts $416c_1$ along other regions of the stent structure, the flexible struts $416c_2$ allow (or do not substantially prevent) the cutting tool to penetrate the graft material 418*c* in the third fenestration region $430c_2$.

Figure 4D:
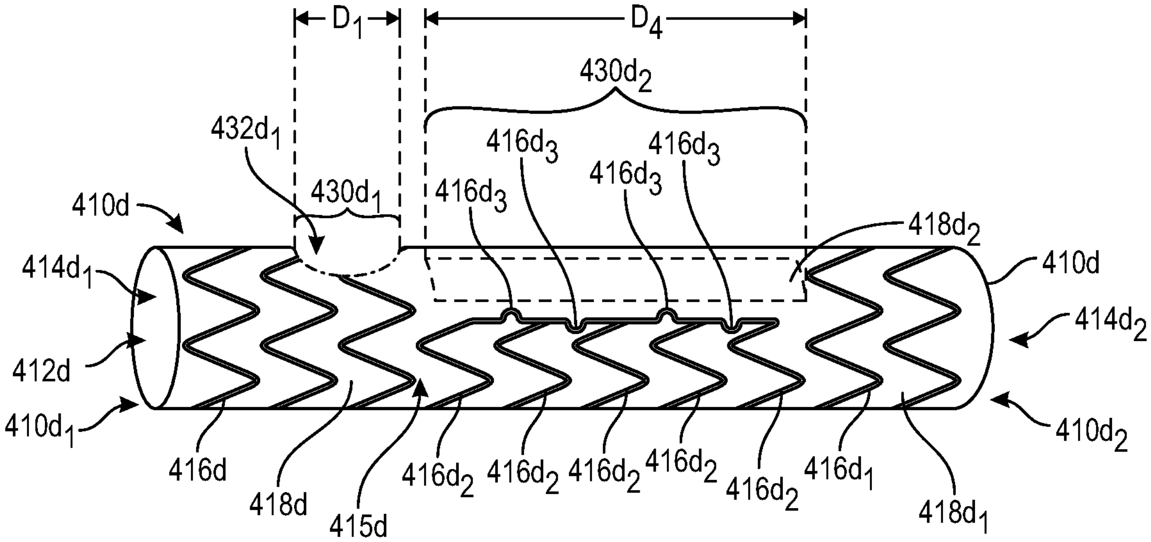

Referring to FIG. 4D, the fourth base member 410*d* includes one or more first struts $416d_1$ or stents that extend fully around (e.g., circumscribe) the perimeter/circumference of the base member 410*d*, and one or more second struts $416d_2$ or stents that extend only partially around the perimeter/circumference of the base member 410*d*. The portion of the base member 410*d* in which the graft material 418*d* is left bare by the partial stents $416d_2$ can define a fourth fenestration region $430d_2$ In some embodiments, the base member 410*d* can include one or more third struts 416*d*3 (also referred to as connecting struts, interstitial struts) that extend at least partially between the termini of two or more of the second struts $416d_2$, e.g., in a direction generally parallel to a longitudinal axis of the base member 410*d* (tangential to the direction of the circumferential struts $416d_1$). In at least some embodiments, a single third strut 416*d*3 can couple all of the second struts $416d_2$ together. The second struts $416d_2$ and/or the third struts 416*d*3 can define a substantially stent-free region $418d_2$ (shown in dashed line) of the graft materials 418*d*, which in turn can define the fourth fenestration region $430d_2$. For example, the second struts $416d_2$ and/or the third struts 416*d*3 can border but not pass through the stent-free region $418d_2$. Accordingly, the stent-free region $418d_2$ is easier to puncture for fenestration and/or have a reduced resistance to penetration compared to other regions $418d_1$ of the base member 410*d*. The fourth fenestration region $430d_2$ can have a fourth dimension $D_4$ (e.g., a width, a diameter, a circumference, a cross-sectional area, or the like) sized at least generally similar to the second dimension $D_2$ (FIG. 4B). During an in vivo fenestration formation procedure, the graft material 418*d* in or near the stent-free region $418d_2$ can be penetrated using a cutting tool. The arrangement of the second struts $416d_2$ and/or the third struts 416*d*3 allows (does not substantially prevent) the cutting tool to penetrate the graft material 418*d* in the fourth fenestration region $430d_2$.

Figure 4E:
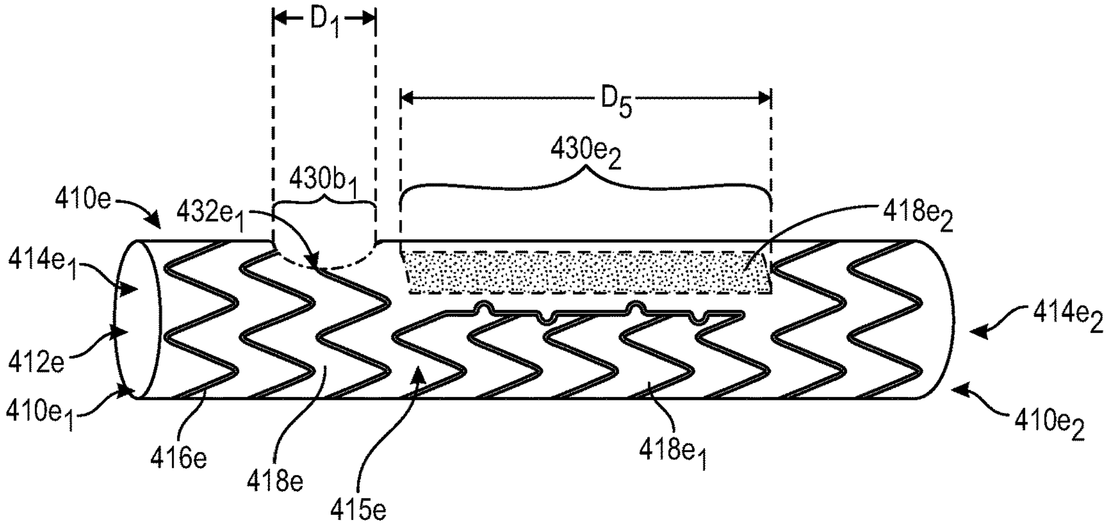

Referring to FIG. 4E, the fifth base member 410*e* includes a fifth fenestration region $430e_2$ and includes certain features at least generally similar to the fourth base member 410*d* of FIG. 4D. In the embodiment illustrated in FIG. 4E, the graft material 418*e* includes a first graft material $418e_1$ outside of the fifth fenestration region $430e_2$ and a second graft material $418e_2$ (shown using dashed line) within the fifth fenestration region $430e_2$. The first graft material $418e_1$ can be made from a fabric and/or any of the other graft material(s) described previously herein. The second graft material $418e_2$ can include a material or combination of materials more easily penetrated (e.g., by a cutting tool) than the first graft material $418e_1$. Additionally, or alternatively, the second graft material $418e_2$ can include a material or combination of materials configured to form (e.g., automatically form) a substantially fluid-impermeable seal when fenestrated and/or with a branch member inserted through the fifth fenestration region $430e_2$. In some embodiments, for example, the second graft material $418e_2$ can include a polyurethane impregnated fabric, or another suitable material. The fifth fenestration region $430e_2$ can have a fifth dimension $D_5$ (e.g., a width, a diameter, a circumference, a cross-sectional area, or the like) sized generally similar to the second dimension $D_2$ (FIG. 4B). Fenestrating the fifth fenestration region $430e_2$ can be generally similar to the fenestration procedure of the fourth fenestration region $430d_2$, as described above regarding FIG. 4D. Additionally, during and/or after fenestration, at least a portion of the second graft material $418e_2$ can independently form a substantially fluid impermeable seal with a branch member.

Figure 5:
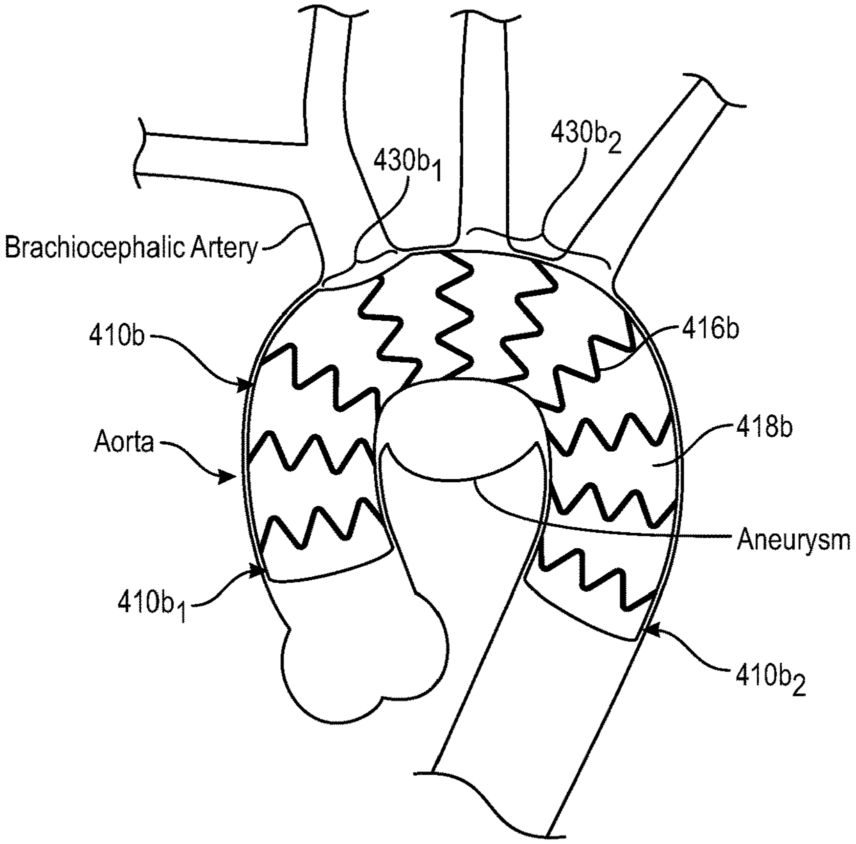
FIG. 5 is a side view of the base member of FIG. 4B positioned in an aortic arch in accordance with embodiments of the present technology.

FIG. 5 is a side view of the base member 410*b* of FIG. 4B positioned in an aortic arch in accordance with embodiments of the present technology. Although FIG. 5 is described with reference to the base member 410*b* of FIG. 4B, it will be appreciated that one or more of the other base members described herein can operate in a generally similar or identical manner to the base member 410*b* and aortic repair device 400*b*. In the illustrated embodiment, the base member 410*b* is deployed across an aneurysm (or other diseased portion) along a portion of the aortic arch and/or the ascending aorta such that the proximal end portion $410b_1$ of the base member 410*b* is positioned in the ascending aorta proximate to the aortic root, and the distal end portion $410b_2$ is positioned at the opposite side of the aneurysm within the descending aorta, thereby causing the base member 410*b* to define a fluid conduit extending across the aneurysm to divert blood from the diseased region. The struts 416*b* can expand the graft material 418*b* into contact with the inner wall of the aorta and/or one or more of the branch vessels to provide a seal between the vessel and the base member 410*b*. More particularly, the base member 410*b* can sealingly contact the inner wall of the proximal aorta such that all or substantially all blood flow through the aorta enters the first opening $414b_1$. Additionally, one or more of the fenestration regions $430b_{1-2}$ can be at least partially aligned with one or more of the branch vessels. As shown in FIG. 5, for example, the preformed fenestration of the first fenestration region $430b_1$ can be aligned with the branching brachiocephalic artery, while the longer second fenestration region $430b_2$ can span one or two additional branching arteries to facilitate in situ fenestration. Once implanted, the base member 410*b* can direct the blood flow (i) through base member 410*b* and out into the aorta to perfuse the aorta and (ii) through the fenestration region $430b_1$ and into the brachiocephalic artery to perfuse the brachiocephalic artery.

In some aspects of the present technology, the base member 410*b* can be positioned against/adjacent to a diseased portion of the aorta, such as the origin of a dissection and/or aneurysm, to block blood flow into the diseased portion by diverting the blood flow through the base member 410*b* and past the diseased portion. In additional aspects of the present technology, the entire outer surface of the base member 410*b* has a tubular shape configured to engage and seal with the inner wall of the aorta. That is, the base member 410*b* can provide a relatively long sealing region along all or substantially all of a length of the base member 410*b*.

The base member 410*b* can be delivered to the aorta in a collapsed configuration within a catheter system (not shown). The catheter system can access the aorta via any suitable intravascular path—such a transfemoral approach, a transcarotid approach, a transsubclavian approach, transapical approach, and so on.

In some embodiments, as described in further detail below, other implantable devices can be modularly coupled to the base member 410 during the same or a different intravascular procedure. For example, a separate tubular stent graft or other implant (e.g., a branch member) can be coupled to one or more of the fenestration regions 430$b_{1-2}$ and extend into the brachiocephalic artery or another branch vessel. Likewise, a separate tubular stent graft or another implant can be coupled to the base member 410*b* and extend farther through the aorta and/or to a branch vessel, such as described previously herein with reference to FIGS. 3C-3F.

Figure 6A:
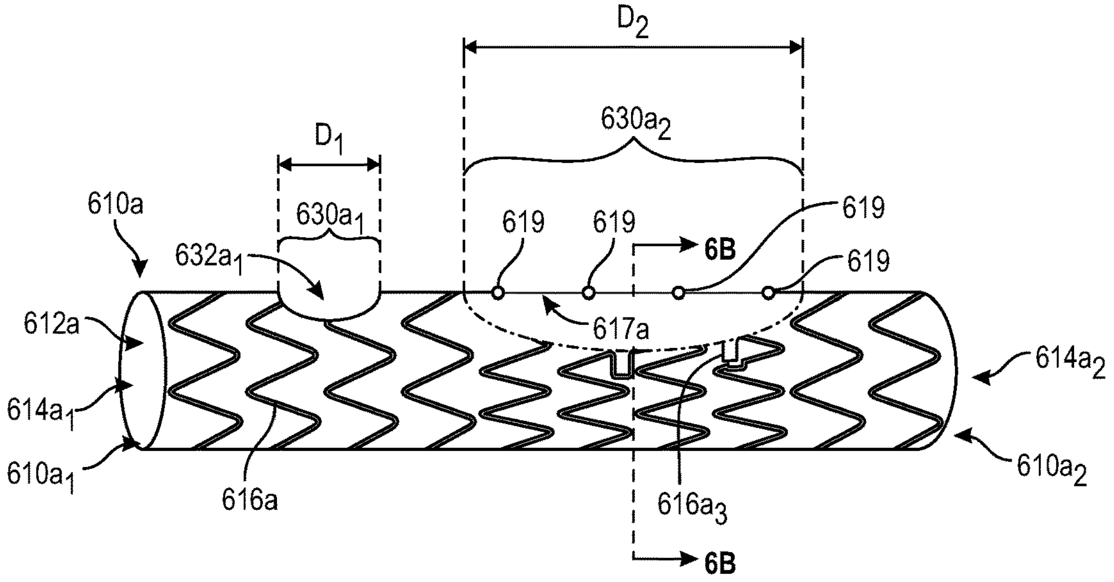
FIGS. 6A and 6B are perspective and side cross-sectional views of a base member of an aortic repair device configured in accordance with embodiments of the present technology.
Figure 6B:
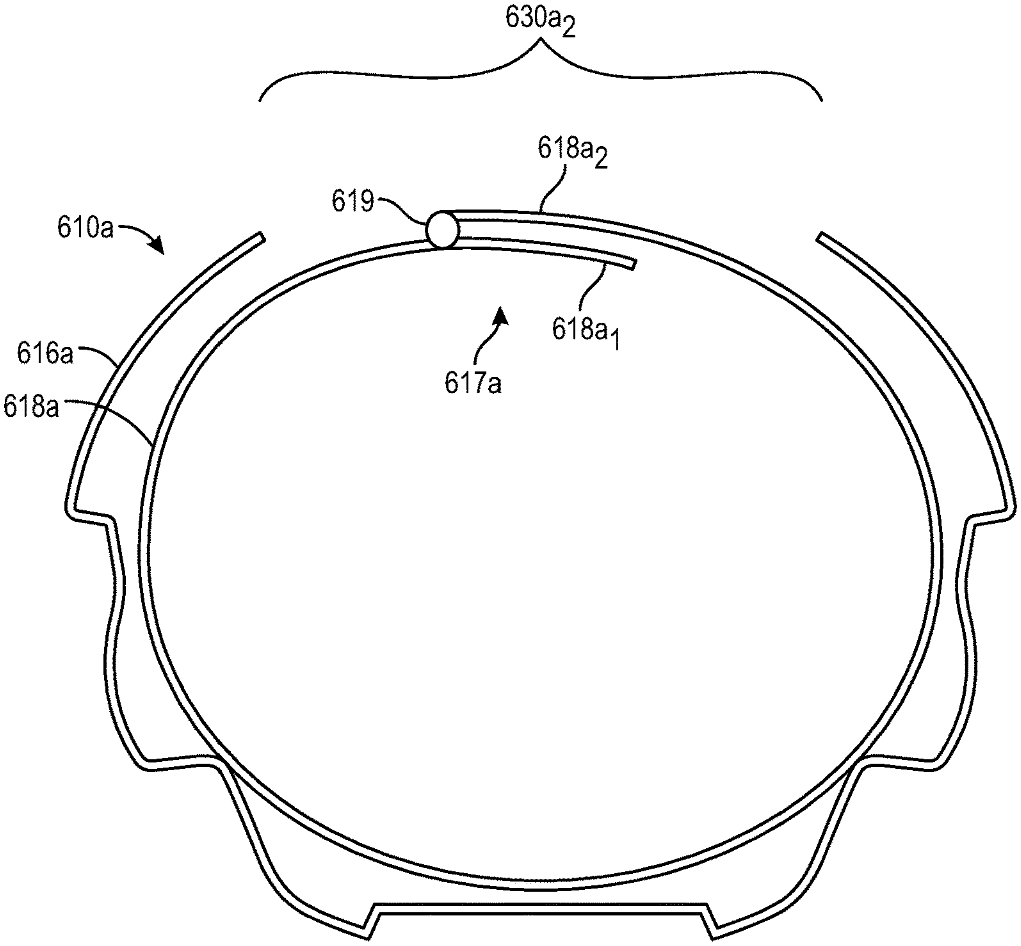
Figure 6C:
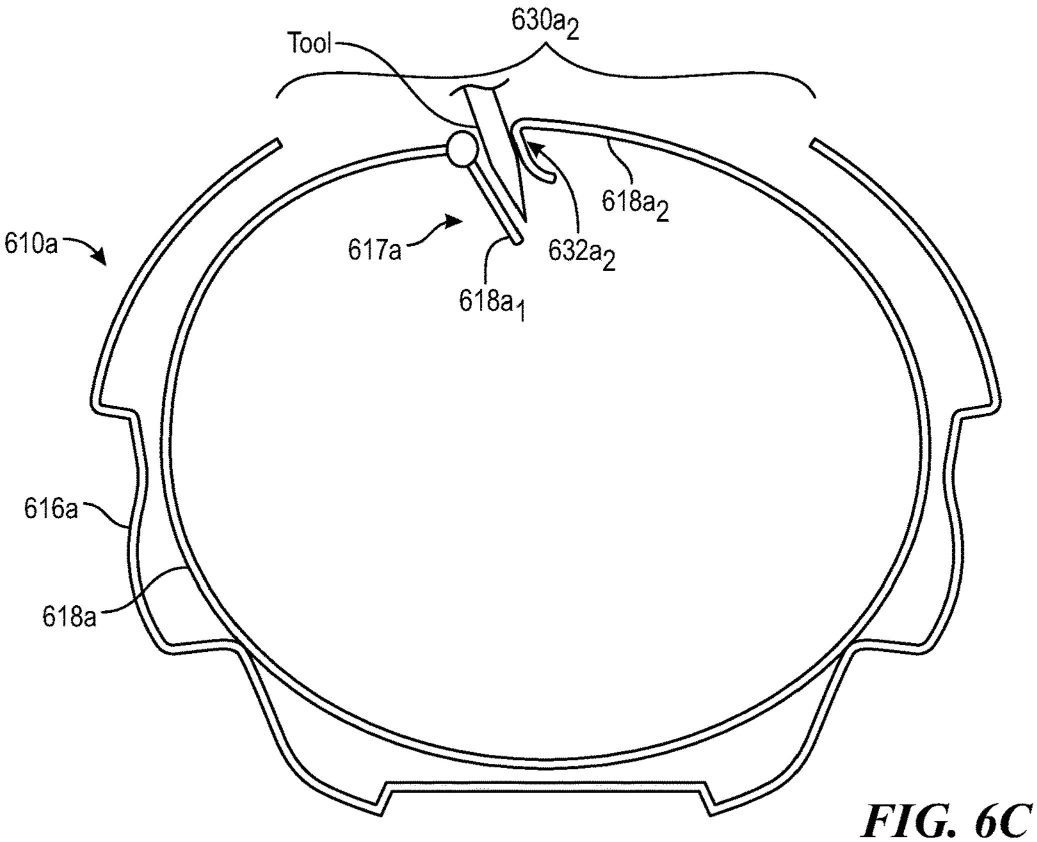
FIGS. 6C and 6D are side cross-sectional views of the base member of FIGS. 6A and 6B during different stages of a fenestration process in accordance with embodiments of the present technology.
Figure 6D:
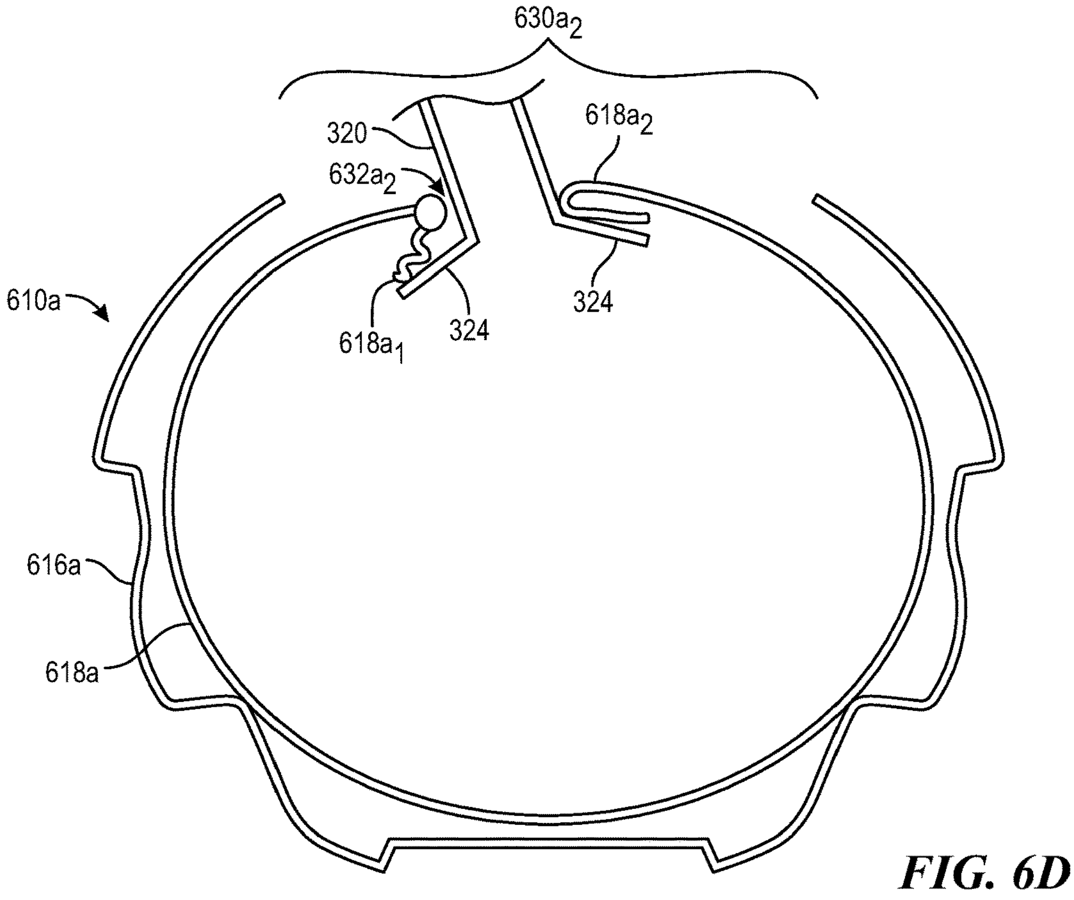

FIGS. 6A-6D illustrate a base member 610*a* configured in accordance with some embodiments of the present technology. Specifically, FIG. 6A is a perspective view of the base member 610*a*, FIG. 6B is a cross-sectional view of the base member 610*a* taken along section line 6B-6B in FIG. 6A, and FIGS. 6C and 6D are side cross-sectional views of the base member 610*a* of FIG. 6A during an in vivo fenestration procedure. The base member 610*a* can include certain features generally similar to the features of one or more of the base members 410*a-e* described above with respect to FIGS. 4A-4E, with like numbers (e.g., first fenestration region 630$a_1$ versus the respective first fenestration regions 430$a_1$-$e_1$) indicating elements with at least generally similar or identical structure and/or function.

Referring to FIG. 6A, the base member 610*a* can include a fenestration region 630$a_2$ defined by a relatively or completely stent-free section (e.g., similar in structure and function to the fourth base member 410*d* (FIG. 4D) and/or the fifth base member 410*e* (FIG. 4E)). In the illustrated embodiment, for example, the base member 610*a* includes one or more connector struts 616$a_3$, individual ones of which can be generally similar to or the same as one or more of the third struts 416$d_3$ of the fourth base member 410*d*.

Referring to FIGS. 6A and 6B together, the second fenestration region 630$a_2$ includes an overlap or overlapping region 617*a* (best seen in FIG. 6B) of the graft material 618*a* secured together by one or more coupling elements 619. As shown in FIG. 6B, the overlapping region 617*a* can include a first end portion 618$a_1$ of the graft material 618*a* and a second end portion 618$a_2$ of the graft material 618*a* at least partially aligned with (e.g., positioned radially inwardly or outwardly from) the first portion 618$a_1$ such that the first and second end portions of the graft material 618*a* overlap each other to create a section with double the graft material. The coupling elements 619 can be sutures, adhesive elements, one or more struts 616*a* extending at least partially around the perimeter of the base member 610*a*, and/or any other suitable coupling element that can temporarily or permanently secure the overlapping first and second end portions of the graft material together. In at least some embodiments, one or more of the coupling elements 619 can be partially or fully radiopaque. In the illustrated embodiment, the second fenestration region 630$a_2$ includes four coupling elements 619 spaced apart from each other (e.g., intermittently) in a direction generally parallel to the longitudinal axis of the base member 610*a*. In some embodiments, the second fenestration region 630$a_2$ can include more or fewer coupling elements 619, and/or one or more of the coupling elements 619 may have other suitable locations and/or arrangements. In at least some embodiments, for example, the coupling elements 619 can be spaced apart a distance (e.g., a length) corresponding to a dimension (e.g., a diameter) of a branch member, such that the branch member can be coupled to the base member 610 and positioned at least partially between two of the coupling elements 619. The base member 610 (and/or any of the other base members and/or spanning members described herein) may have radiopaque markers to guide the delivery of the branch member delivery tool into the appropriate point in the fenestration region.

As shown in FIG. 6C, the first end portion 618$a_1$ and/or the second end portion 618$a_2$ of the graft material 618*a* can bend or deflect radially inwardly, toward a center or central longitudinal axis of the base member 610*a* when a tool (e.g., a cutting tool, a branch member delivery tool, a cutting zone tool, or the like) is inserted through the second fenestration region 630$a_2$ between two of the coupling elements 619 (FIG. 6A). During insertion, the tool can push or bend the first end portion 618$a_1$ of the graft material to a first (e.g., left) side of the tool, and/or the second end portion 618$a_2$ of the graft material 618*a* to a second (e.g., right) side of the tool opposite the first side. Accordingly, in at least some embodiments, the second fenestration region 630$a_2$ is configured such that the tool passes through the second fenestration region 630$a_2$ and at least partially enters the base member 610*a* without or substantially without piercing, cutting, or dilating the graft material 618*a*.

Referring to FIG. 6D, the first end portion 618$a_1$ and/or the second end portion 618$a_2$ of the graft material 618*a* can also be bent/deflected (e.g., inwardly) by a branch member, such as the branch member 320 of FIG. 3B, as it is coupled to the base member 610*a*. In the illustrated embodiment, for example, the branch member 320 is positioned partially within the base member 610*a* and extends through the second fenestration region 630$a_2$, e.g., via the fenestration 632$a_2$. A coupling portion 324 of the branch member 320, embodiments of which are described in further detail with reference to FIGS. 27-31, can contact the first portion 618$a_1$ and/or the second portion 618$a_2$ of the graft material 618*a*, such that the first end portion 618$a_1$ and/or the second end portion 618$a_2$ can be compacted or "bunched" between the respective end of the branch member 320 and the rest of the graft material 618*a*, as shown in FIG. 6D. In such embodiments, the coupling portion 324 can hold the first end portion 618$a_1$ and/or the second end portion 618$a_2$ of the graft material 618*a* to at least partially prevent the first portion 618$a_1$ and/or the second portion 618$a_2$ of the graft material 618*a* from interfering with fluid flow through the base member 610*a* and/or the branch member 320.

In some embodiments, the overlapping first and second portions 618$a_{1-2}$ of the graft material 618*a* are differentially tensioned, for example, by connecting (e.g., sewing) the second end portion 618$a_2$ (e.g., the outer section) of the graft material 618*a* slightly tighter than the first end portion 618$a_1$ (e.g., inner section) of the graft material 618*a*. In some embodiments, this is expected to enhance the seal between the base member 610 and the branch member 320. Additionally, or alternatively, one or more of the opening(s) formed by the overlapping regions 617*a* can be longitudinally oriented along the longitudinal axis of the base member 610*a* (e.g., as shown in FIGS. 6A-6D), circumferentially and/or radially oriented around the longitudinal axis of the base member 610*a*, or at some diagonal angle between these two orientations. In at least some embodiments, one or more of the overlapping regions 617*a* are aligned with the orientation of one or more of the stents 616*a*.

In these and other embodiments, the edges of the first and second end portions 618$a_{1-2}$ can be reinforced, such as with additional suturing. This reinforcement suturing can extend circumferentially around at least a portion of the peripheral edge of the opening formed by the overlapping region 617$a$. The circumference of the opening can be configured so that, when the branch member 320 (FIG. 6D) is placed therethrough, the overlapping region 617$a$ forms a substantially fluid-impermeable seal with the branch member 320 that provides a durable junction expected to withstand the stresses or fatigue it may endure over the patient's lifetime. Additional wrapping sutures may extend around this reinforcement suturing, for example, to hold the reinforcement suturing in place. This reinforcing suture can also assist in forming a seal when the fenestration 632$a_2$ is closed, and/or structurally reinforcing the fenestration 632$a_2$ when the branch member 320 is placed therethrough.

To enhance the strength of the fenestration 632$a_2$, and/or to further provide a robust connection between the base member 610$a$ and the branch member 320, one or more wires, such as stent wires, can be positioned at least partially around the peripheral edge of the fenestration 632$a_2$ and/or the fenestration region 630$a_2$ (FIG. 6A). For stents 616$a$ with a generally diamond-shaped pattern, the fenestration 632$a_2$ and/or the fenestration region 630$a_2$ can be positioned in the center of one of the diamonds, so that the branch member 320 can engage with the surrounding wires. If the branch member 320 is larger than the spacing between stent wires, some of the struts of the stents 616$a$ can be modified, shortened, and/or removed to enlarge the spacing between stent struts to provide for a bare graft region that can be punctured to create an opening that is at least generally similar in size to the branch graft. For example, the stent structs can be arranged in a diamond pattern rather than a herringbone pattern in that region, e.g., to crate larger potential opening areas. In these and other embodiments, the base member 610$a$ can be configured to close against the branch member 320, for example, to improve the seal/connection between the base member 610$a$ and the branch member 320. For example, the stents 616$a$ proximate the fenestration region 630$a_2$ can be configured to compress or expand in response to insertion of the branch member 320. For stents 616$a$ that extend longitudinally along the base member 610$a$, the stents 616$a$ can expand radially and/or foreshorten, such that the stents 616$a$ may naturally bow open as the base member 310 is inserted through the overlapping region 617$a$, e.g., due to the foreshortening of the distance between the stent ends. This can provide a direct metallic support around some or all of the overlapping region 617$a$, which is expected to provide a robust and/or durable connection between the base member 610$a$ and the branch member 320 at the branch graft ostium. In some embodiments, one or more of the stents 616$a$ proximate the fenestration region 430$a_2$ can be pre-shaped and/or biased toward a preferred geometry in which the pre-shaped stents overlap each other prior to insertion of the base member 310. When the base member 310 is inserted through the fenestration region 430$a_2$, the pre-shaped stents can press against the branch member 320, thereby providing a secure seal/connection with the base member 610$a$. In embodiments in which the stents 616$a$ have a Z-stent pattern, the bend of the Z-stents can be aligned with/around the fenestration region 430$a_2$, such that the branch member 320 can engage the Z-stents as well as the base member 610$a$.

Figure 7:
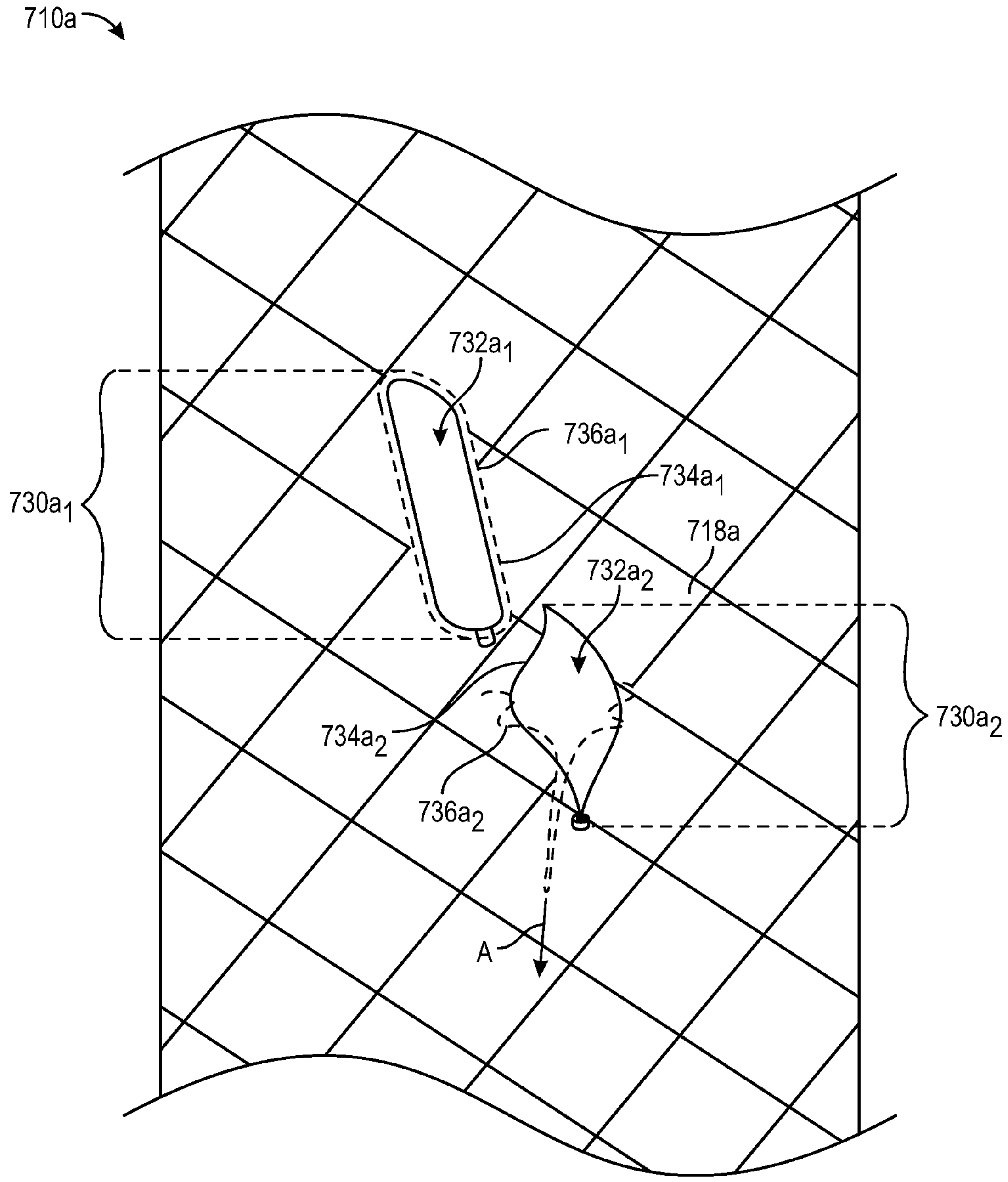
FIG. 7 is an enlarged top view of a portion of a base member of an aortic repair device configured in accordance with embodiments of the present technology.

FIG. 7 is a top view of a portion of a base member 710$a$ of an aortic repair device 700$a$ configured in accordance with embodiments of the present technology. The base member 710$a$ can include various features generally similar to the base members 410$a$-$e$, 610$a$ described above with respect to FIGS. 4A-6D, with like numbers (e.g., graft material 718$a$ versus the respective graft material 418$a$-$e$ of FIGS. 4A-4E) indicating like elements. As shown in FIG. 7, the base member 710$a$ can include one or more closeable or sealable fenestration regions 730 (referred to individually as a first fenestration region 730$a_1$ and a second fenestration region 730$a_2$). In other embodiments, the base member 710$a$ can include more or fewer fenestration regions 730$a$, such as less than two, more than two, or any other suitable number of fenestration region 730$a$.

Each of the fenestration regions 730$a_{1-2}$ can include a fenestration 732$a_{1-2}$ (e.g., an opening) extending through the graft material 718$a$, and defined at least partially by a closeable border 734$a$ (also referred to as a "closable edge" or a "closable perimeter"). A closing or sealing element 736$a$ (shown in dashed line) can extend partially or fully around the associated perimeter 734$a_{1-2}$ and/or fenestration 732$a_{1-2}$ and can include one or more sutures, one or more cords, one or more shape memory materials, and/or any other suitable material. In the illustrated embodiment, the sealing elements 736$a$ are shown spaced laterally outward from the associated perimeter 734$a$ for the sake of illustrative clarity; it will be appreciated that, in these and other embodiments, individual ones of the sealing elements 736$a$ can at least partially or fully contact the associated perimeter 734$a$.

Each of the sealing elements 736$a_{1-2}$ can be configured to adjust (e.g., open and/or close) the corresponding fenestration 732$a_{1-2}$. In the illustrated embodiment, for example, the second sealing element 736$a_2$ includes a cord, and the cord has been drawn or pulled in the direction indicated by the arrow A such that the second sealing element 736$a_2$ draws the second perimeter 734$a_2$ together to seal or close the second fenestration 732$a_2$. In some embodiments, individual ones of the sealing elements 736$a_{1-2}$ can draw the associated perimeter 734$a_{1-2}$ toward an object (e.g., a branch member) inserted within the respective fenestration 732$a_{1-2}$, e.g., to at least partially seal or couple the object with the corresponding fenestration region 730. Additionally, or alternatively, individual ones of the sealing elements 736$a_{1-2}$ can seal unused fenestrations regions 730$a_{1-2}$, e.g., fenestrations regions that are not used as part of an aortic repair procedure. In the illustrated embodiment, the first sealing element 736$a_1$ and the second sealing element 736$a_2$ are separate and configured to selectively and independently close the associated fenestrations 732$a_{1-2}$. In other embodiment, the first sealing element 736$a_1$ and the second sealing element 736$a_2$ can be operably coupled and/or otherwise configured to operate in tandem, such that using one of the sealing elements (e.g., the first sealing element 736$a_1$) to seal the associated fenestration (e.g., the first fenestration 732$a_1$) causes the other sealing element (e.g., second sealing element 736$a_2$) to seal the other fenestration (e.g., the second fenestration 732$a_2$).

In some embodiments, one or both of the sealing elements 736$a_{1-2}$ can include a pre-tied slip-knot (not shown) and/or other feature that can be cinched or tightened by pulling on a single end of the associated sealing element 736$a_{1-2}$. The sealing element 736$a_{1-2}$ and/or a cord associated therewith may extend through a delivery catheter to the proximal end of the delivery system to allow a user (e.g., a physician) to pull on the sealing elements 736$a_{1-2}$ to tighten or close the associated fenestration 732$a_{1-2}$. In some embodiments, one or both of the sealing elements 736$a_{1-2}$ may pass through a relatively incompressible tube which abuts the slip-knot, so that the sealing elements 736$a_{1-2}$ can be tightened without pulling on the base member 710$a$ and/or displacing the base member 710$a$ from its position within the patient. An aortic repair device including the base member 710$a$ can further comprise a system for cutting the sealing elements 736$a_{1-2}$ at or near to the slip-knot. Additionally, or alternatively, one or more of the cutting tools described with reference FIGS. 20A-26C can be used to cut the sealing elements 736$a_{1-2}$.

IV. SELECTED EMBODIMENTS OF FENESTRATION TOOLS

FIGS. 8-22D illustrate various fenestration tools configured for use with one or more base members of the present technology, such as any of the base members described above with reference to FIGS. 3A-7. Although some of the fenestration tools are described with reference to "pre-fenestrated base members" or "base members fenestrated in situ" for the sake of illustration, such description is not limiting and at least some or all of the fenestration tools of the present technology can be configured for use with pre-fenestrated base members, base members fenestrated in situ, and/or any other suitable base members. Additionally, although some of the fenestration tools are described with reference to the left common carotid artery, it will be appreciated that the fenestration tools of the present technology can also be used with other arteries, such as the brachiocephalic artery and/or the left subclavian artery, the renal arteries, celiac artery, mesenteric arteries, and others. Furthermore, although some of the fenestration tools are described and/or illustrated as approaching a base member via a branch vessel of the aorta, it will be appreciated that one or more of the fenestration tools can also be inserted within the base member/aorta and used to approach one or more of the branch vessels from within the base member/aorta.

A. Selected Embodiments of Centering Tools

FIGS. 8-10B illustrate centering tools 840, 940, 1040 (respectively) configured in accordance with embodiments of the present technology. The various centering tools 840, 940, 1040 can include some features that are at least generally similar or identical in structure and/or function to one another, and/or can operate in a generally similar or identical manner to one another. Moreover, one or more of the different features of the centering tools 840, 940, 1040 of the present technology can be combined with each other and/or omitted.

Each of the centering tools 840, 940, 1040 can include a shaft 842, 942, 1042 having a distal end portion 842*a*, 942*a*, 1042*a*, and an expandable component 844, 944, 1044 coupled to the shaft at or near the distal end portion 842*a*, 942*a*, 1042*a*. Each of the expandable components 844, 944, 1044 can be annular and extend at least partially around the corresponding shaft 842, 942, 1042. Additionally, each of the expandable components 844, 944, 1044 can be configured to expand from a first, low-profile state (e.g., used during device delivery to the target site) to a second, deployed state. In the second state, each of the expandable components has a larger cross-sectional dimension than in the low-profile state, which allows the expandable components 844, 944, 1044 to engage an inner wall of the base member 310 (via the fenestration 332), for example, to maintain the fenestration 332 in a desired position (e.g., centered) relative to the branch vessel.

The centering tools 840, 940, 1040 can be delivered through a branch vessel of the patient's aorta while in the low-profile delivery state and extend through the fenestration 332 such that the expandable component 844, 944, 1044 is positioned within the interior lumen of the base member 310. In at least some embodiments, for example, the expandable components 844, 944, 1044 are positioned within the base member 310 and transitioned to the deployed state, and the centering tools 840, 940, 1040 are drawn proximally away from the aorta and/or against an inner surface of the base member 310 to draw the base member 310 toward the branch vessel and/or center the fenestration 332 relative to the branch vessel. The expandable components 844, 944, 1044 can be positioned within the base member 310 before the base member 310 is fully expanded, e.g., when the base member 310 is in a partially-expanded state. In this state, the base member 310 is expected to be easier and/or safer to manipulate or position within the aorta. In some aspects of the present technology, the centering tools 840, 940, 1040 can facilitate precise alignment of the fenestration 332 with the branch vessel and/or maintain the relative position of the fenestration 332 to the branch vessel when attaching a branch member to the base member 310.

Figure 8:
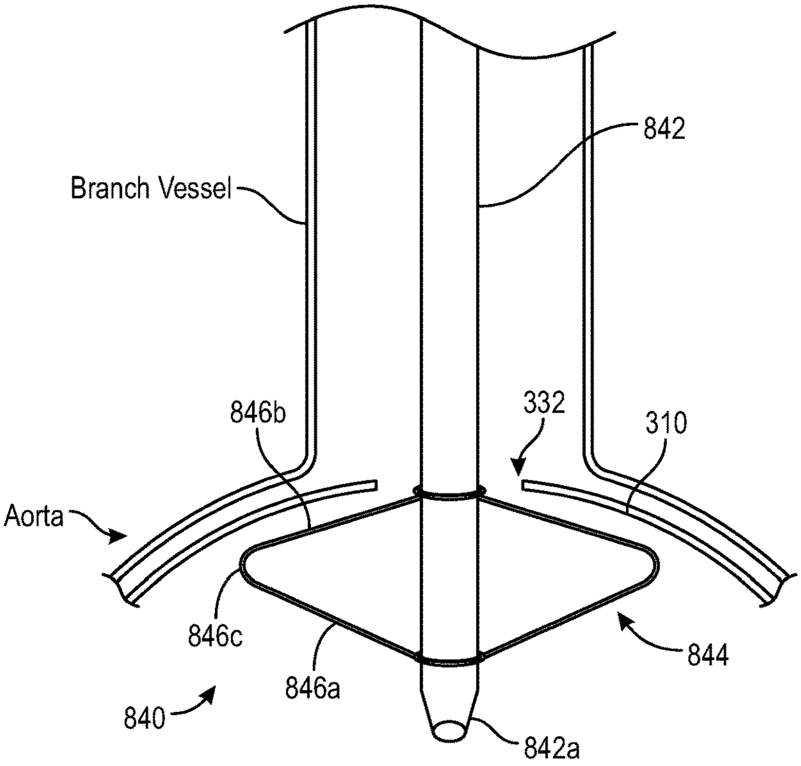
FIG. 8 is a side view of a centering tool inserted into a fenestration of a base member via a branch vessel, the centering tool configured in accordance with embodiments of the present technology.

In the embodiment illustrated in FIG. 8, the expandable component 844 includes a first (e.g., distal) surface 846*a*, a second (e.g., proximal) surface 846*b* opposite the first surface 846*a*, and an intermediate or apex region 846*c* between the first surface 846*a* and the second surface 846*b*. One or both of the first surface 846*a* and the second surface 846*b* can extend at an angle relative to the shaft 842 and radially outward toward the apex region 846*c*, such that the expandable component 844 can have a diamond shape. The apex region 846*c* can define a maximum outer dimension (e.g., outer width or outer diameter) of the expandable component 844. The expandable component 844 can be formed from a balloon, or another expandable structure. During a procedure, the centering tool 840 can be drawn proximally back into the branch vessel such that the second surface 846*b* contacts the inner surface of the base member 310 proximate the fenestration 332. The expandable component 844 can move the base member 310 toward the branch vessel and center the fenestration 332 relative to the branch vessel.

Figure 9:
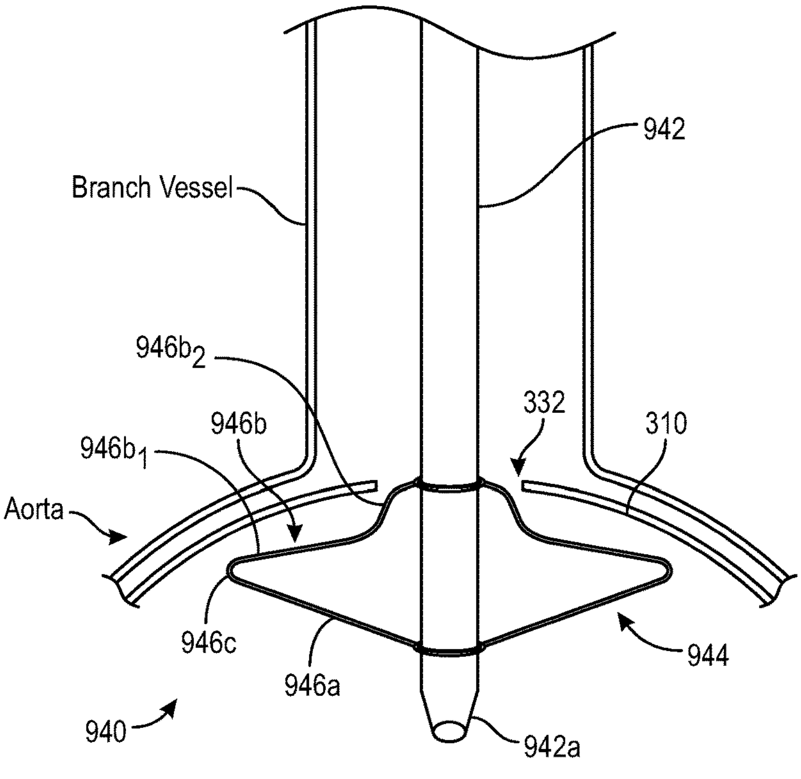
FIG. 9 is a side view of a centering tool inserted into a fenestration of a base member via a branch vessel, the centering tool configured in accordance with embodiments of the present technology.

In the embodiment illustrated in FIG. 9, the expandable component 944 includes a first (e.g., distal) surface 946*a*, a second (e.g., proximal) surface 946*b* opposite the first surface 946*a*, and an intermediate or apex region 946*c* between the first surface 946*a* and the second surface 946*b*, each of which can be at least generally similar to the correspondingly named and/or numbered first surface 846*a*, second surface 846*b*, and apex region 846*c* of FIG. 8. Additionally, the second surface 946*b* can include a first region 946$b_1$ and a second region 946$b_2$. The first region 946$b_1$ can be at least partially between the apex region 946*c* and the second region 946$b_2$. The second region 946$b_2$ can extend at an angle from the first region 946$b_1$, radially inward in the proximal direction away from the distal end portion 942*a* and/or toward the shaft 942. Accordingly, the second region 946$b_2$ can define a tubular or necked portion of the expandable component 944 configured to engage and/or be received at least partially within the fenestration 332. In at least some embodiments, for example, the second region 946$b_2$ is sized to be positionable within the fenestration 332. In such embodiments, when the centering tool 940 is drawn proximally to move the base member 310 toward the branch vessel, at least a portion of the second region 946$b_2$ can pass through the fenestration 332 and extend proximally beyond the base member 310 and/or into the branch vessel. In some aspects of the present technology, the second region 946$b_2$ is expected to improve the centering tool's engagement with the base member 310 and/or the alignment of the fenestration relative to the branch vessel.

Figure 10A:
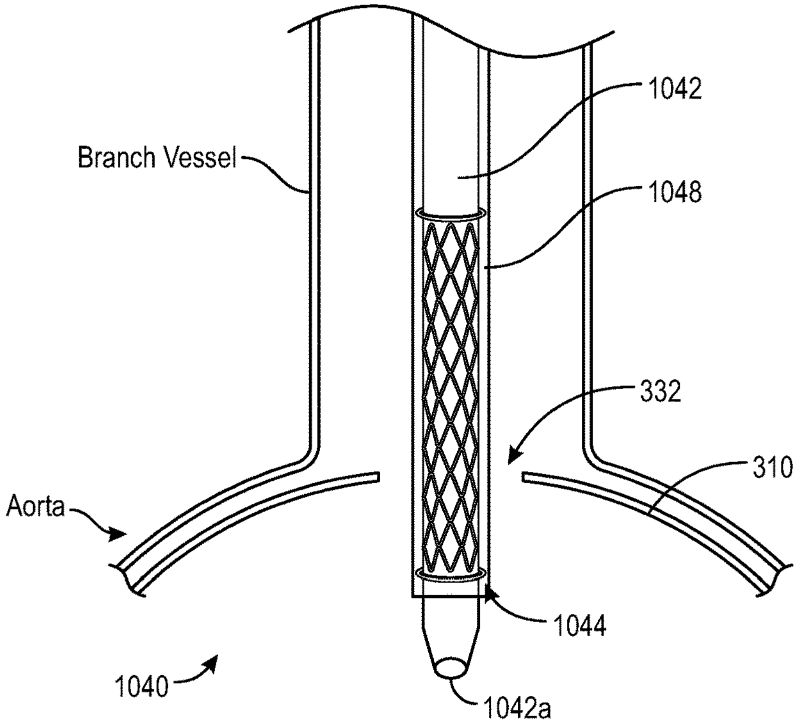
FIGS. 10A and 10B is a side view of a centering tool in a first state and a second state, respectively, as the centering tool is inserted into a fenestration of a base member via a branch vessel, the centering tool configured in accordance with embodiments of the present technology.
Figure 10B:
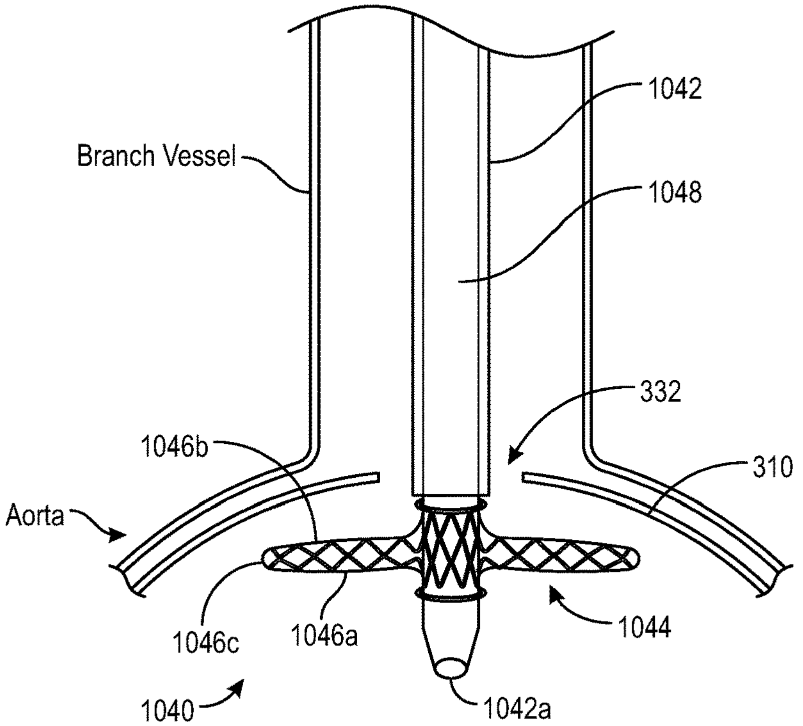

In the embodiment illustrated in FIGS. 10A and 10B, the expandable component 1044 is shown in a first, low-profile, delivery state in FIG. 10A, and a second, deployed state in FIG. 10B. The expandable component 1044 can include a braided structure (e.g., a frame or basket structure) formed from a plurality of filaments (e.g., stent material, pliable polymeric components). In the second, deployed state (shown in FIG. 10B), the expandable component 1044 has a first or distal surface 1046*a*, a second or proximal surface 1046*b* opposite the first surface 1046*a*, and an intermediate or apex region 1046*c* between the first surface 1046*a* and the second surface 1046*b* each of which can be at least generally similar to the correspondingly named and/or numbered first surface 846*a*, second surface 846*b*, and apex region 846*c* of FIG. 8. In the first state, the expandable component 1044 can be positioned within a delivery sheath 1048 and assume a generally elongate or longitudinal profile. A user can position the expandable component 1044 beyond the delivery sheath 1048 to allow the expandable component 1044 to assume a generally radial or disk-shaped profile and transition from the first state toward and/or to the second state. The relative positions of the expandable component 1044 and the delivery sheath 1048 can be adjusted (e.g., to transition the expandable component 1044 between the first and second states) by moving the shaft 1042 and/or the delivery sheath 1048 relative to each other. For example, moving the delivery sheath 1048 proximally uncovers the expandable component 1044 and allows the expandable component 1044 to transition from the first state to the second state. Additionally, or alternatively, moving the shaft 1042 distally extends the expandable component 1044 from within the delivery sheath 1048 and allows the expandable component 1044 to transition from the first state to the second state.

In some aspects of the present technology, the centering tools 840, 940, 1040 can provide more precise alignment of the fenestration 332 with the branch vessel which, in turn, can reduce the risk of failure when perfusing the branch artery with a branch member, such as the branch member 320 of FIG. 3B, or any of the branch members described in detail below with reference to FIGS. 27-31. In these and other aspects, the improved alignment is expected to improve the durability and/or sealing between the base member 310 and a branch perfusion member coupled to the base member 310.

Figure 11A:
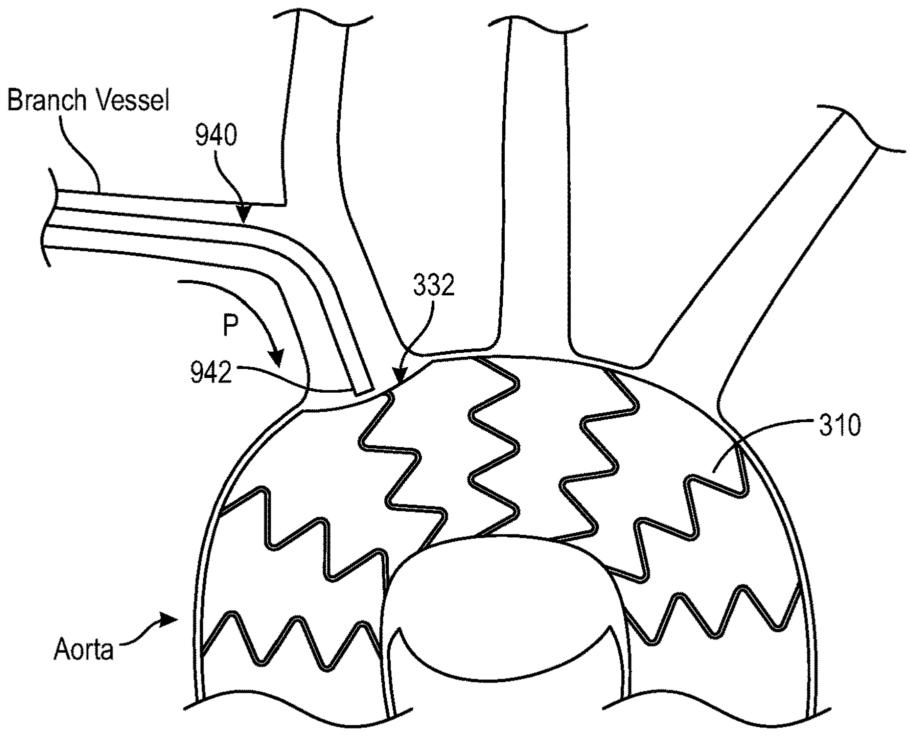
FIGS. 11A-11C are side views of select steps in a process for centering a branch member delivery system relative to a base member of an aortic repair device using a centering tool in accordance with embodiments of the present technology.
Figure 11B:
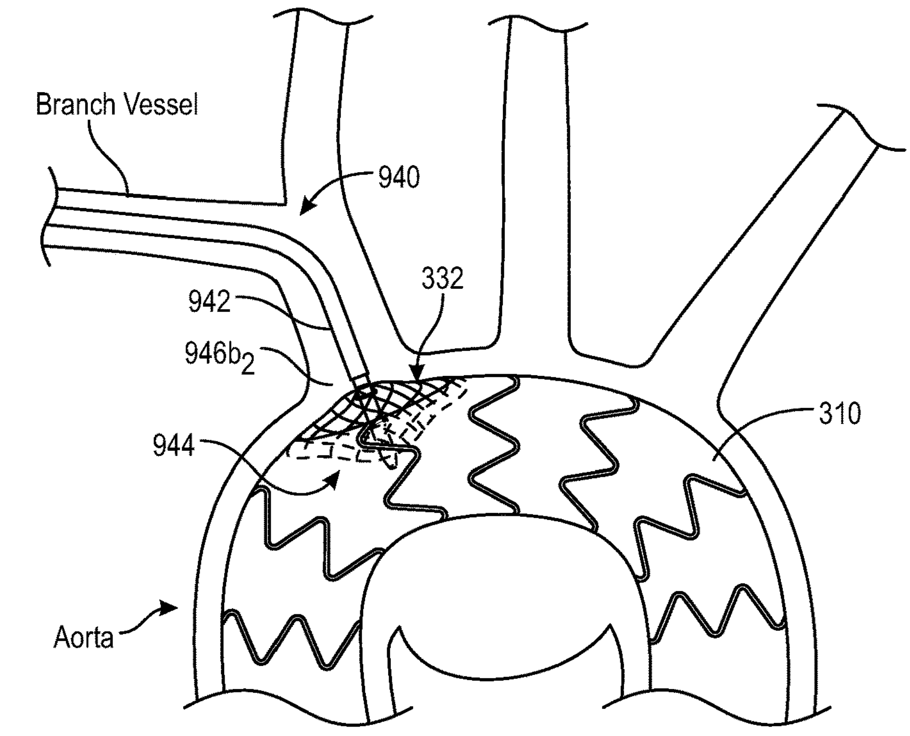
Figure 11C:
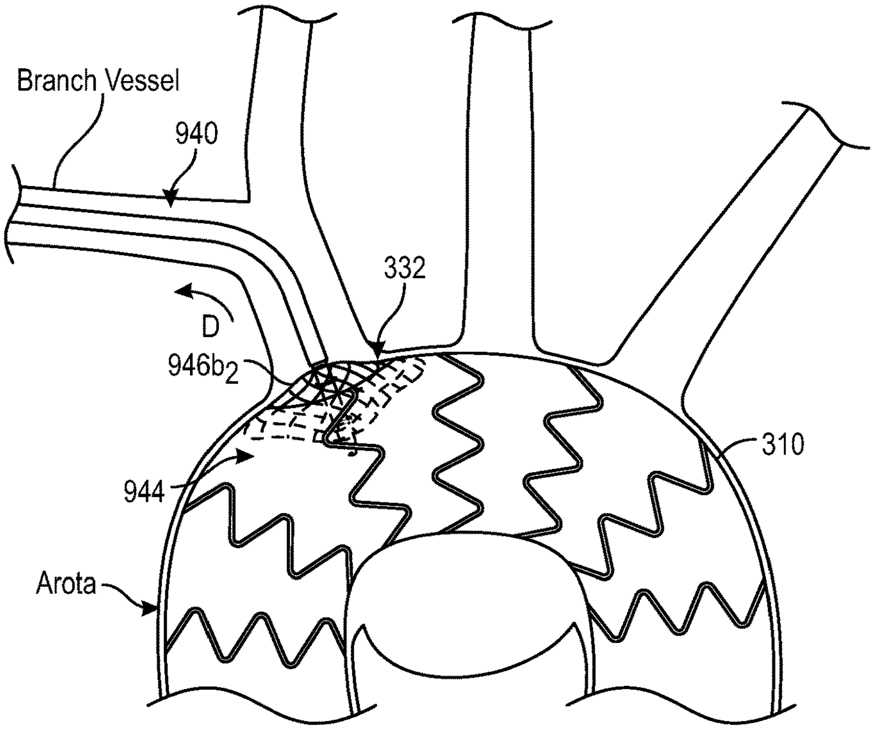

FIGS. 11A-11C are side views of select steps in a process for centering a base member 310 relative to a branch vessel using the centering tool 940 of FIG. 9 in accordance with embodiments of the present technology. Referring to FIG. 11A, the shaft 942 of the centering tool 940 can be delivered distally through a branch vessel, in the direction indicated by arrow P, and positioned proximate the fenestration 332 of the base member 310. The fenestration 332 can be pre-formed prior to delivery of the base member or formed in situ. At least a portion of the shaft 942 can be positioned within the lumen of the base member 310 via the fenestration 332. Referring to FIG. 11B, the expandable component 944 can be expanded to the second state and positioned to engage the interior of the base member 310 proximate the fenestration 332. In the illustrated embodiment, for example, at least a portion of the second region 946*b*$_2$ of the expandable component 944 extends through the fenestration 332, away from the base member 310 and/or toward the branch vessel. Referring to FIG. 11C, the centering tool 940 can be drawn proximally, in the direction indicated by arrow D, to move the base member 310 toward the branch vessel. As the base member 310 is moved toward the branch vessel, the fenestration 332 can be centered relative to the branch vessel. In the illustrated embodiment, at least a portion of the second region 946*b*$_2$ can extend into the branch vessel as the centering tool 940 is moved proximally, which can improve the alignment of (e.g., center) the fenestration 332 relative to the branch vessel.

FIGS. 12-15B illustrate centering fenestration tools 1240, 1340, 1440, 1540 (also referred to as "centering tools"), respectively, configured in accordance with embodiments of the present technology. The centering tools 1240, 1340, 1440, 1540 can include some features that are at least generally similar in structure and function, or identical in structure and function, to one another and/or one or more of the centering tools 840, 940, 1040 described above with respect to FIGS. 8-10B, and/or can operate in a generally similar or identical manner to one another and/or one or more of the centering tools 840, 940, 1040. Moreover, one or more of the features of the centering tools 1240, 1340, 1440, 1540 can be combined with each other, one or more of the centering tools 840, 940, 1040 described above, and/or omitted.

Each of the centering tools 1240, 1340, 1440, 1540 can include a shaft 1242, 1342, 1442, 1542 having a distal end portion 1242*a*, 1342*a*, 1442*a*, 1542*a* and defining a lumen 1243, 1343, 1443, 1543 extending through the shaft 1242, 1342, 1442, 1542. Additionally, each of the centering tools 1240, 1340, 1440, 1540 can include an expandable component 1244, 1344, 1444, 1544 coupled to the shaft 1242, 1342, 1442, 1542 at or near the distal end portion 1242*a*, 1342*a*, 1442*a*, 1542*a*. Each of the expandable components 1244, 1344, 1444, 1544 can be generally annular and/or extend at least partially around the corresponding shaft 1242, 1342, 1442, 1542. Additionally, each of the expandable components 1244, 1344, 1444, 1544 can be configured to expand from a first, low-profile state to a second, deployed state. In the second state, each of the expandable components 1244, 1344, 1444, 1544 can be configured to engage the branch vessel to position (e.g., center) the shaft 1242, 1342, 1442, 1542 and/or the lumen 1243, 1343, 1443, 1543 relative to the branch vessel and/or the fenestration region 330 of the base member 310.

During a procedure, each of the centering tools 1240, 1340, 1440, 1540 can be delivered through a branch vessel of the patient's aorta and positioned with the distal end portion 1242*a*, 1342*a*, 1442*a*, 1542*a* proximate to the fenestration region 330. The expandable components 1244, 1344, 1444, 1544 can be transitioned to second state and centered within the branch vessel and/or relative to the fenestration region 330. As the expandable components 1244, 1344, 1444, 1544 expand, each can press against the inner surface of the branch vessel and automatically center the shaft 1242, 1342, 1442, 1542 relative to the branch vessel and/or holding the shaft 1242, 1342, 1442, 1542 substantially stationary relative to the branch vessel and/or the base member 310. Once centered, a cutting tool, such as any of the cutting tools described in detail below with reference to FIGS. 20A-21B, can be delivered through the lumen 1243, 1343, 1443, 1543 and used to form a fenestration through the base member 310 in the fenestration region 330. In some aspects of the present technology, the centering tools 1240, 1340, 1440, 1540 can improve the alignment of a fenestration formed in the fenestration region 330 with the branch vessel. For example, by centering the shaft 1242, 1342, 1442, 1542 and the lumen 1243, 1343, 1443, 1543 within the branch vessel before fenestration, the fenestration (i.e., opening) formed in the fenestration region 330 is expected to also be centered with the branch vessel. This, in turn, is expected to improve the alignment of and/or reduce the risk of failure when perfusing the branch vessel with a branch member inserted into the branch vessel via the fenestration.

Figure 12:
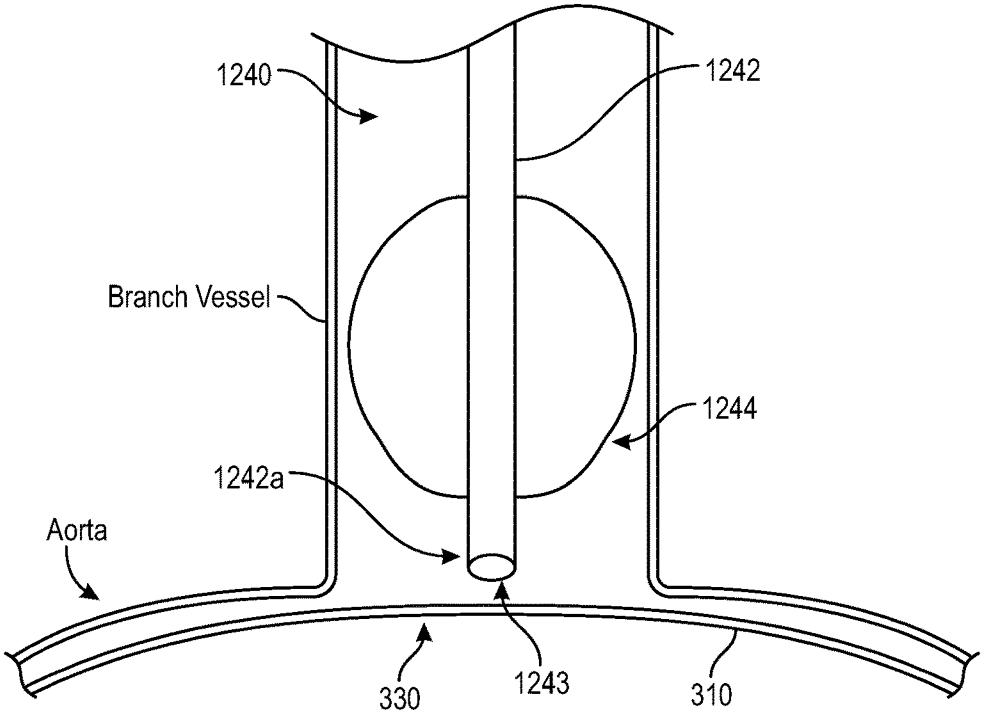
FIGS. 12-15B are side views of respective centering tools positioned in a branch vessel proximate a base member in an aortic arch, the centering tools configured in accordance with embodiments of the present technology.

In the embodiment illustrated in FIG. 12, the expandable component 1244 is a balloon that can inflate or otherwise expand from the first state to the second state (shown in FIG. 12). In some embodiments, the balloon is compliant and configured to at least partially conform to the inner topology of the branch vessel when in the second state. As the balloon expands, the balloon can contact the branch vessel around all, or at least a portion, of a circumference of the balloon to center the shaft 1242 within the branch vessel.

Figure 13:
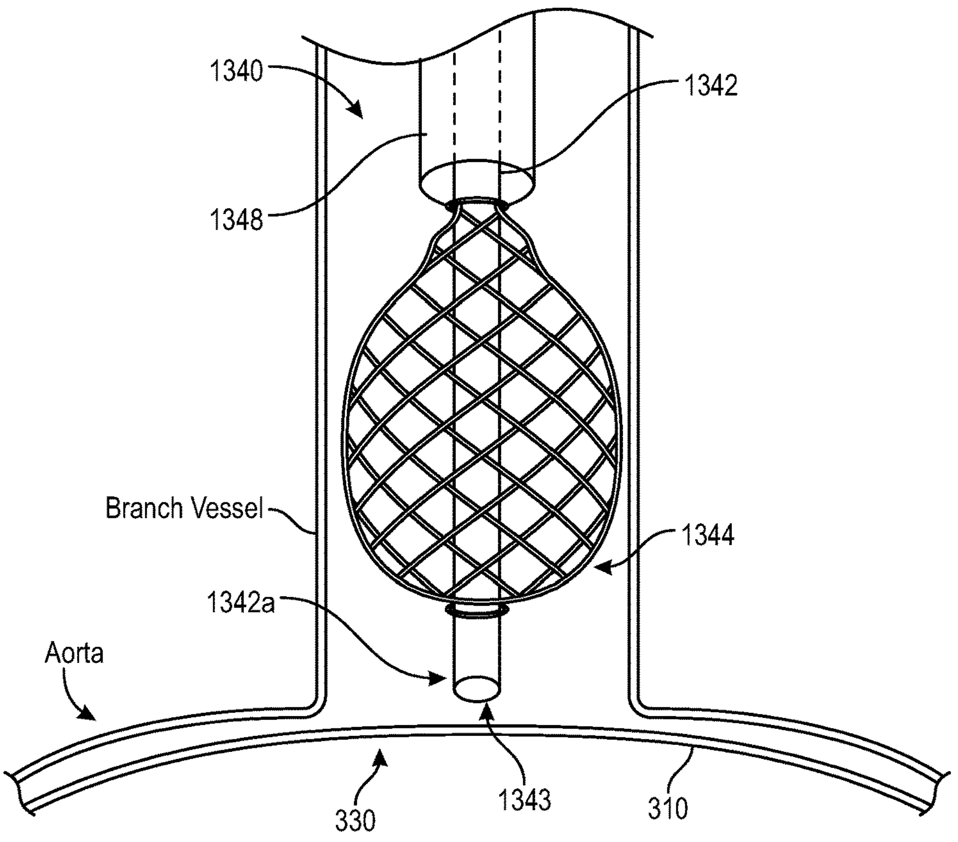

In the embodiment illustrated in FIG. 13, the expandable component 1344 is an expandable frame or basket structure. The expandable frame can be made from a braided stent structure, a laser cut structure, a mesh structure, a braided balloon structure, and/or other suitable expandable frames or basket-like structures. The expandable frame can be positioned within a delivery sheath 1348 in the first state. The delivery sheath 1348 can be withdrawn proximally, and/or the shaft 1342 can be moved distally, to uncover the expandable component 1344 and allow the expandable frame to transition to the second state (shown in FIG. 13). In some embodiments, the expandable component 1344 can be configured to automatically transition to the second state when uncovered. As the expandable frame expands toward and/or to the second state, the expandable frame can contact the branch vessel around all, or at least a portion, of a circumference of the expandable frame to center the shaft 1342 within the branch vessel.

Figure 14:
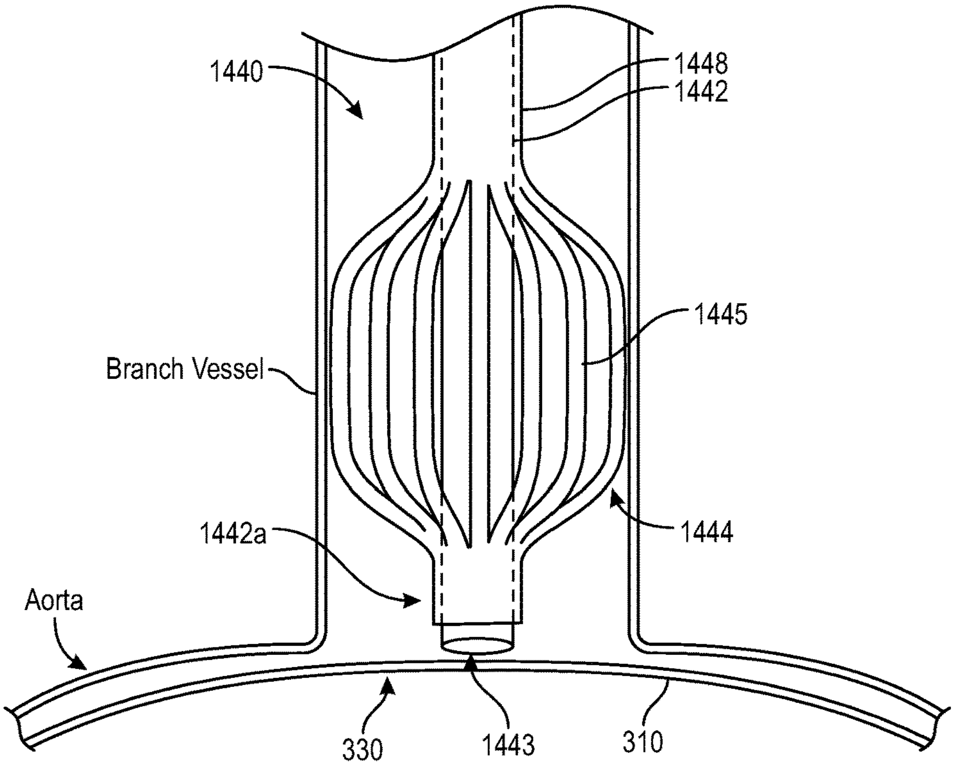

In the embodiment illustrated in FIG. 14, the expandable component 1444 includes a plurality of deformable struts 1445 formed in an outer sheath 1448 that can be disposed around the shaft 1442. Individual ones of the deformable struts 1445 can extend in a direction generally parallel to the longitudinal axis of the shaft 1442 and can be configured to flex or deform radially outwardly (e.g., away from the shaft 1442) to transition the expandable component 1444 toward the second state, and radially inwardly (e.g., toward the shaft 1442) to transition the expandable component 1444 toward the low-profile, first state. In some embodiments, the outer sheath 1448 can be fixed to the shaft 1442 at or next to the distal end portion 1442*a*. During a fenestration procedure, the outer sheath 1448 can be advanced toward the distal end portion 1442*a* to thereby cause the struts 1445 to flex outwardly and transition the expandable component 1444 to the second state, as shown in FIG. 14. Additionally, or alternatively, the distal end portion 1442*a* can be retracted toward the outer sheath 1448 to transition the expandable component 1444 to the second state. As the struts 1445 flex outwardly, individual ones of the struts 1445 can contact the branch vessel to center the shaft 1442 within the branch vessel.

Figure 15A:
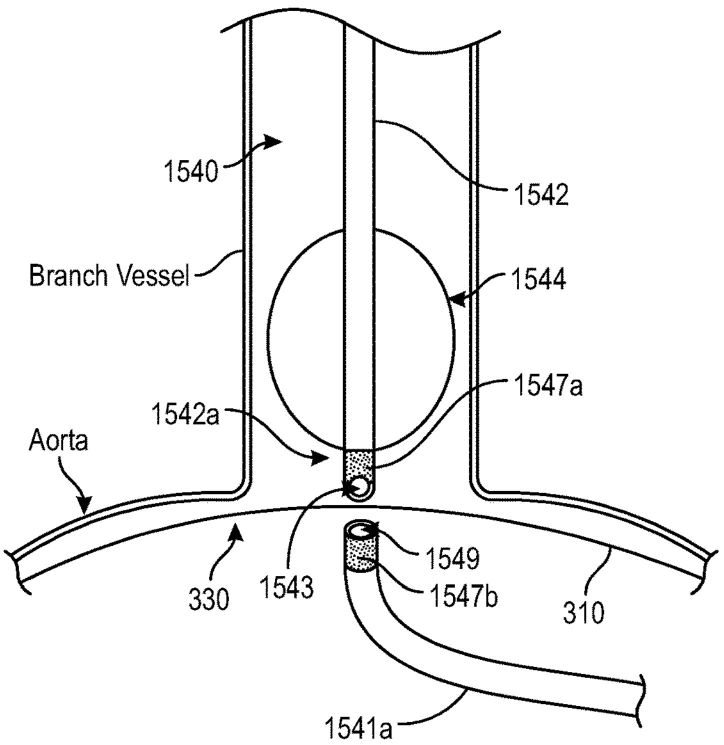

In the embodiment illustrated in FIG. 15A, the centering tool 1540 includes a first coupling element 1547*a* at or proximate the distal end portion 1542*a* of the shaft 1542. The centering tool 1540 further includes a second shaft 1541*a* that can include a second coupling element 1547*b* configured to engage the first coupling element 1547*a* from opposing sides of the wall of the base member 310. In some embodiments, the first and second coupling elements 1547*a-b* are magnets and/or electromagnets of opposite polarities such that they are drawn to each other when they are positioned near each other. The second shaft 1541*a* can define a second lumen 1549 which can be at least partially aligned with the first lumen 1543 of the centering tool 1540 when the first coupling element 1547*a* engages the second coupling element 1547*b*. In the illustrated embodiment, the first and second coupling elements 1547*a-b* are configured to engage with each other across the sidewall of the base member 310. Accordingly, a cutting tool (not shown) can be inserted through the first lumen 1543, pierce the sidewall of the base member 310 to form a fenestration in the fenestration region 330, and enter the second lumen 1549. In some embodiments, the cutting tool may move in the opposite direction. As further shown in FIG. 15A, the centering tool 1540 can also include the expandable component 1544, which can be a balloon, expandable frame, expandable sheath, and/or other suitable expandable structure.

Figure 15B:
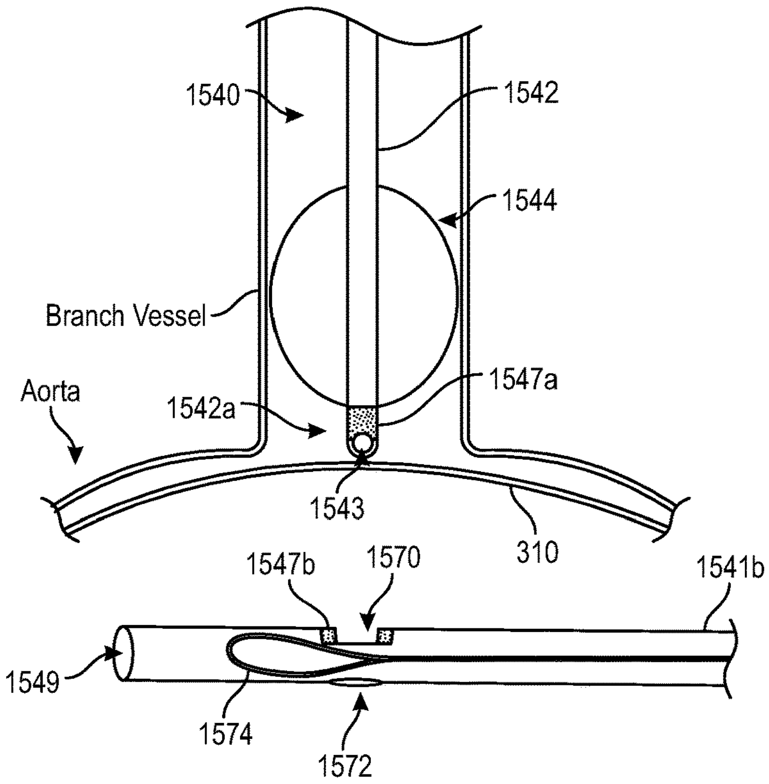

In the embodiment illustrated in FIG. 15B, the centering tool 1540 includes the first shaft 1542 described previously with reference to FIG. 15A and a second shaft 1541*b* at least generally similar in structure and/or function to the second shaft 1541*a* described previously with reference to FIG. 15A. However, the second shaft 1541*b* has an opening 1570 formed through a sidewall of the second shaft 1541*b*, and one or more second coupling elements 1547*b* are positioned around the side opening 1570. During a fenestration procedure, the second coupling elements 1547*b* can be drawn toward and/or otherwise interact with the first coupling elements 1547*a* (e.g., via magnetic attraction) to align the opening 1570 of the second shaft 1541*b* with the lumen 1543 of the opposing first shaft 1542. With the lumen 1543 and the opening 1570 aligned, a user can insert a tool (e.g., a cutting tool) through the lumen 1543 to pierce or otherwise extend through the base member 310 to enter the second shaft 1541*b* via the opening 1570. In some embodiments, the second shaft 1541*b* can further include a second side opening 1572 positioned along a portion of the sidewall spaced apart from the first opening 1570 (e.g., on the opposite side of the first opening 1570), such that the tool inserted through the lumen 1543 can pass completely through the second shaft 1541*b* via the openings 1570, 1572. In some embodiments, the tool (and/or a guidewire thereof) extending through the side opening 1570 can be directed into the lumen 1549 of the second shaft 1541*b*, such that the tool/guidewire extends completely through the lumen 1549 and is accessible outside of the body, providing rail support during the procedure. In various embodiment, direct the tool and/or guidewire into the lumen 1549 of the second shaft 1541*b* a loop or snare component 1574 can be positioned within the lumen 1549 and configured to engage (e.g., cinch around) the tool and/or guidewire. For example, the snare component 1574 can capture the guidewire and/or the tool once inserted through the opening 1570 and then a user can move (e.g., pull) the snare component 1574 to move the guidewire/tool proximally through the lumen 1549 of the second shaft 1541*b*, for example, to provide rail support across the target site.

B. Selected Embodiments of Cutting Zone Tools

FIGS. 16-19 illustrate cutting zone tools 1650, 1750, 1850, and 1950, respectively, configured in accordance with embodiments of the present technology. The various cutting zone tools 1650, 1750, 1850, 1950 can include some features that are at least generally similar or identical in structure and/or function to one another, and/or can operate in an at least generally similar or identical manner to one another. Moreover, one or more of the different features of the cutting zone tools 1650, 1750, 1850, 1950 of the present technology can be combined with each other and/or omitted.

Each of the cutting zone tools 1650, 1750, 1850, 1950 can include a body or shaft 1652, 1752, 1852, 1952 having a distal end portion 1652*a*, 1752*a*, 1852*a*, 1952*a*, and a blocker or catcher component 1654, 1754, 1854, 1954 coupled to the shaft 1652, 1752, 1852, 1952 at or near the distal end portion 1652*a*, 1752*a*, 1852*a*, 1952*a*. In some embodiments, individual ones of the shafts 1652, 1752, 1852, 1952 can define a lumen 1653, 1753, 1853, 1953 through which one or more tools, such as one or more of the cutting tools described in detail with reference to FIGS. 20A-21B, can be delivered. Each of the catcher components 1654, 1754, 1854, 1954 can be configured to at least partially prevent material, such as debris from the base member 310 created when fenestrating the base member 310 in situ, from flowing into the branch vessel. In some embodiments, for example, each of the catcher components 1654, 1754, 1854, 1954 is configured to transition between a first, low-profile delivery state and a second, expanded blocking or catching state (shown in FIGS. 16-19, respectively). In the second state, each of the catcher components 1654, 1754, 1854, 1954 have a larger cross-sectional dimension than in the first state to define a cutting zone 1651, 1751, 1851, 1951 between the catcher component 1654, 1754, 1854, 1954 and the base member 310 configured to catch all, or at least a portion, of the debris created when fenestrating the base member 310 and/or otherwise block all, or at least a portion, of the debris from flowing into the branch vessel.

During a fenestration procedure, a user can navigate the cutting zone tool 1650, 1750, 1850, 1950 through a branch vessel toward the aortic arch and/or a base member 310 positioned therein. At or near the base member 310, the user can expand the cutting zone tool 1650, 1750, 1850, 1950 to the second state to define the cutting zone 1651, 1751, 1851, 1951. In some embodiments, for example, the user can press the catcher components 1654, 1754, 1854, 1954 against the base member 310 to cause at least a portion of the base member 310, such as at least a portion of the fenestration region 330, to bend or flex away from the branch vessel and/or the inner aortic wall. This pressing can trap fenestration debris and/or other material within the cutting zone 1651, 1751, 1851, 1951. Additionally, or alternatively, this pressing can create counter-tension in the base member 310 which can make it easier to pierce the base member 310, e.g., through the fenestration region 330. In these and/or other embodiments, advancing the cutting zone tool 1650, 1750, 1850, 1950 from the branch vessel to press against the base member 310 can deflect a portion of the base member 310 away from the aortic wall and/or the branch vessel wall which, in turn, is expected to provide more space to perform the fenestration. In some embodiments, the user can expand the catcher component 1654, 1754, 1854, 1954 at least partially or fully within the branch vessel (e.g., proximally of an ostium of the branch vessel) to prevent, or at least partially prevent, material from flowing into the branch vessel. In these and/or other embodiments, the user positions another of catcher component distally and/or downstream from the branch vessel to capture other material flowing through the aorta.

Figure 16:
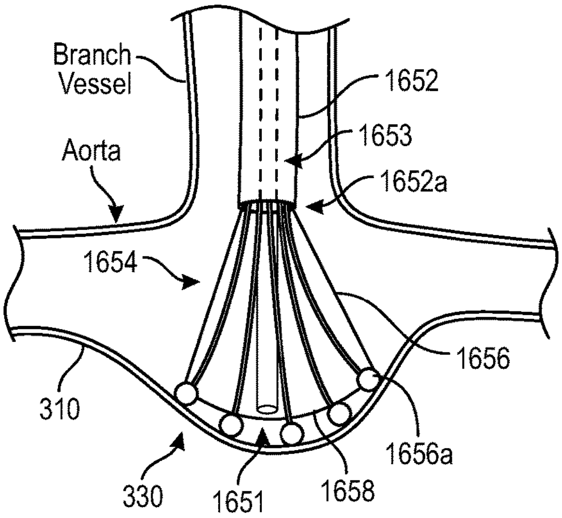
FIGS. 16-19 are side views of respective cutting zone tools positioned at an in situ fenestration site proximate a base member, the cutting zone tools configured in accordance with embodiments of the present technology.

In the embodiment illustrated in FIG. 16, the catcher component 1654 includes one or more fingers or struts 1656 extending distally and/or radially outwardly from the distal end portion 1652*a* of the shaft 1652. Individual ones of the struts 1656 can be formed from a shape memory material such as Nitinol or another suitable material. In some embodiments, individual ones of the struts 1656 can include an atraumatic tip or distal terminus 1656*a*. For illustration purposes, only one of the struts 1656 and atraumatic tips 1656*a* are labeled in FIG. 16. In the illustrated embodiment, the catcher component 1654 further includes a cone or funnel 1658. The funnel 1658 can be formed from a polymer, such as polyurethane, and/or another suitable material, and can be extended at least partially around one or more of the struts 1656. In other embodiments, the funnel element 1658 can be omitted. During a fenestration procedure, the catcher component 1654 can be transitioned between the first and second states by retracting a delivery sheath, such as the delivery sheath 1348 of FIG. 13, configured to constrain the catcher component 1654 in the first configuration and/or advancing the shaft 1652 distally through the delivery sheath to uncover the catcher component 1654 and allow the catcher component 1654 to transition to the second state. In the second (e.g., expanded) state, the catcher component 1654 can "catch" debris created when fenestrating the base member 310 in vivo, for example, by moving a cutting tool proximally through the base member 310 as described in greater detail with reference to FIGS. 21B and FIGS. 22A-22E. In some embodiments, the funnel 1658 can be used to center the cutting zone tool 1650 relative to the branch vessel and define the cutting zone 1651. In some embodiments, the funnel 1658 can be used as a contact barrier positionable between other elements (e.g., cutting tool) and anatomy (e.g., aorta, supra-aortic arteries), for example, to protect or shield the anatomy from injury during manipulation of the other elements.

Figure 17:
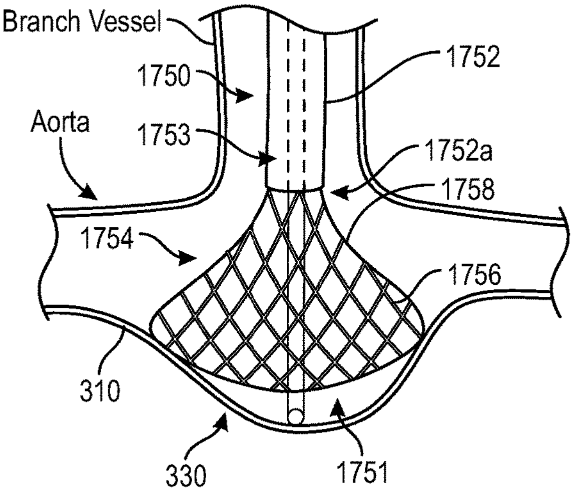

In the embodiment illustrated in FIG. 17, the catcher component 1754 includes a cone or funnel 1758. The funnel 1758 can be at least generally similar in structure and/or function to the funnel 1658 of FIG. 16, but can include a plurality of braided filaments 1756 instead of a material extending around one or more struts. During a procedure, the catcher component 1754 can be transitioned between the first and second states by retracting a delivery sheath, such as the delivery sheath 1348 of FIG. 13, configured to constrain the catcher component 1754 in the first configuration and/or advancing the shaft 1752 distally through the delivery sheath to uncover the catcher component 1754 and allow the catcher component 1754 to transition to the second state. In the second (e.g., expanded) state, the catcher component 1754 can "catch" debris created when fenestrating the base member 310 in vivo, such as when a cutting tool is pulled back through the base member 310, as described in greater detail with reference to FIGS. 21B and FIGS. 22A-22F. In some embodiments, the funnel 1758 can be configured to transition to the second state automatically when the shaft 1752 is advanced distally through the branch vessel toward the base member 310. In such embodiments, the funnel 1758 can be used to center the cutting zone tool 1750 relative to the branch vessel and define the cutting zone 1751. In some embodiments, the funnel 1758 can be used as a contact barrier positionable between other elements (e.g., cutting tool) and anatomy (e.g., aorta, supra-aortic arteries), for example, to protect or shield the anatomy from injury during manipulation of the other elements.

Figure 18:
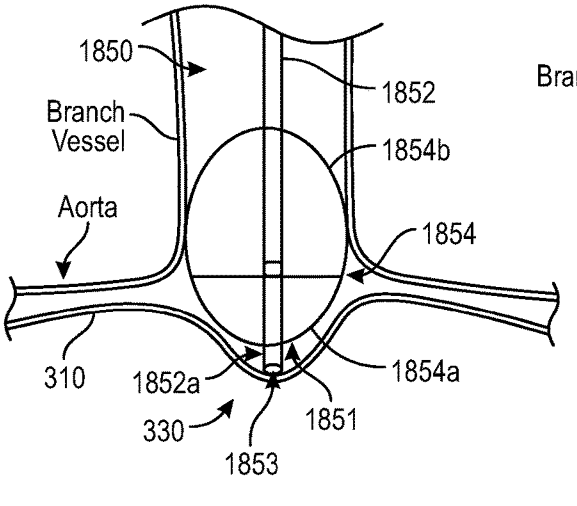

In the embodiment illustrated in FIG. 18, the catcher component 1854 includes a balloon, which can include features at least generally similar in structure and/or function as those of the balloon 1244 described above with reference to FIG. 12. Additionally, the catcher component 1854 includes a distal region 1854*a* having a first material property and a proximal region 1854*b* having a second material property different than the first material property. In the illustrated embodiment, for example, the distal region 1854*a* has a first stiffness and the proximal region 1854*b* has a second stiffness less than the first stiffness such that the distal region 1854*a* is less compliant the first proximal region 1854*b*. In these and other embodiments, the proximal region 1854*b* can be configured to engage the branch vessel, such as described in detail regarding the balloon 1244 of FIG. 12, and the distal region 1854*a* can be configured to press against the base member 310 to cause the base member 310 to bend/flex and define the cutting zone 1851.

Figure 19:
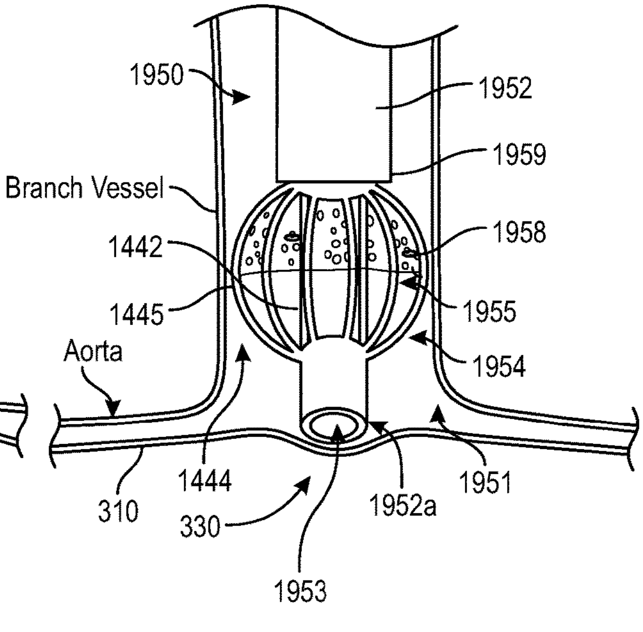

In the embodiment illustrated in FIG. 19, the catcher component 1954 includes at least some aspects that are at least generally similar in structure and/or function to the expandable component 1444 of FIG. 14. For example, the catcher component 1954 includes a plurality of deformable struts 1445 disposed about an inner shaft 1442. The deformable struts 1445 can define an interior 1955 of the catcher component 1954, and the interior 1955 can be configured to contain a membrane or filter 1958. In the illustrated embodiment, the filter 1958 has a concave and/or hemispherical shape that faces toward the base member 310. In other embodiments, the filter 1958 can have a convex shape, or another suitable shape. The filter 1958 can include micropores configured to catch or block debris within the interior 1955 while allowing fluid (e.g., blood) flow through the catcher component 1954. During a fenestration procedure, the filter 1958 can be configured to transition between the first and second states in response to movement of the deformable struts 1445. In some embodiments, the cutting zone tool 1950 includes a delivery sheath 1959 which can be advanced over the catcher component 1954 to transition the catcher component 1954 from the second state (shown in FIG. 19) to the first state.

C. Selected Embodiments of Fenestration Cutting Tools

FIGS. 20A-D, 21A, and 21B illustrate cutting tools 2060 and 2160*a-b*, respectively, configured in accordance with embodiments of the present technology. The cutting tools 2060, 2160*a-b* can include some features that are at least generally similar in structure and function, or identical in structure and function to one another, and/or can operate in an at least generally similar or identical manner to one another. Moreover, one or more of the different features of the cutting tools 2060, 2160*a-b* of the present technology can be combined with each other and/or omitted. Each of the cutting tools 2060, 2160*a-b* can have a cutting feature 2062, 2162 configured to pierce or penetrate through a base member, such as the base member 310, to form a fenestration therethrough. The cutting tools 2060, 2160*a-b* can be used in tandem with one or more of the other tools described herein, as described with reference to FIGS. 22A-22F. Generally, any of the cutting features and/or cutting tools described herein can include one or more sharpened surfaces, pointed surfaces, serrated surfaces, edges, blades, cutting balloons, and/or other types of mechanical cutting structures configured to cut or pierce through the base member 310. Additionally, or alternatively, the cutting features and/or cutting tools can include various other modalities or mechanisms for forming fenestrations, such as bipolar energy, electrical current, RF energy, microwave energy, high-frequency ultrasound (HIFU), laser energy, and/or hydro-dissection.

Figure 20A:
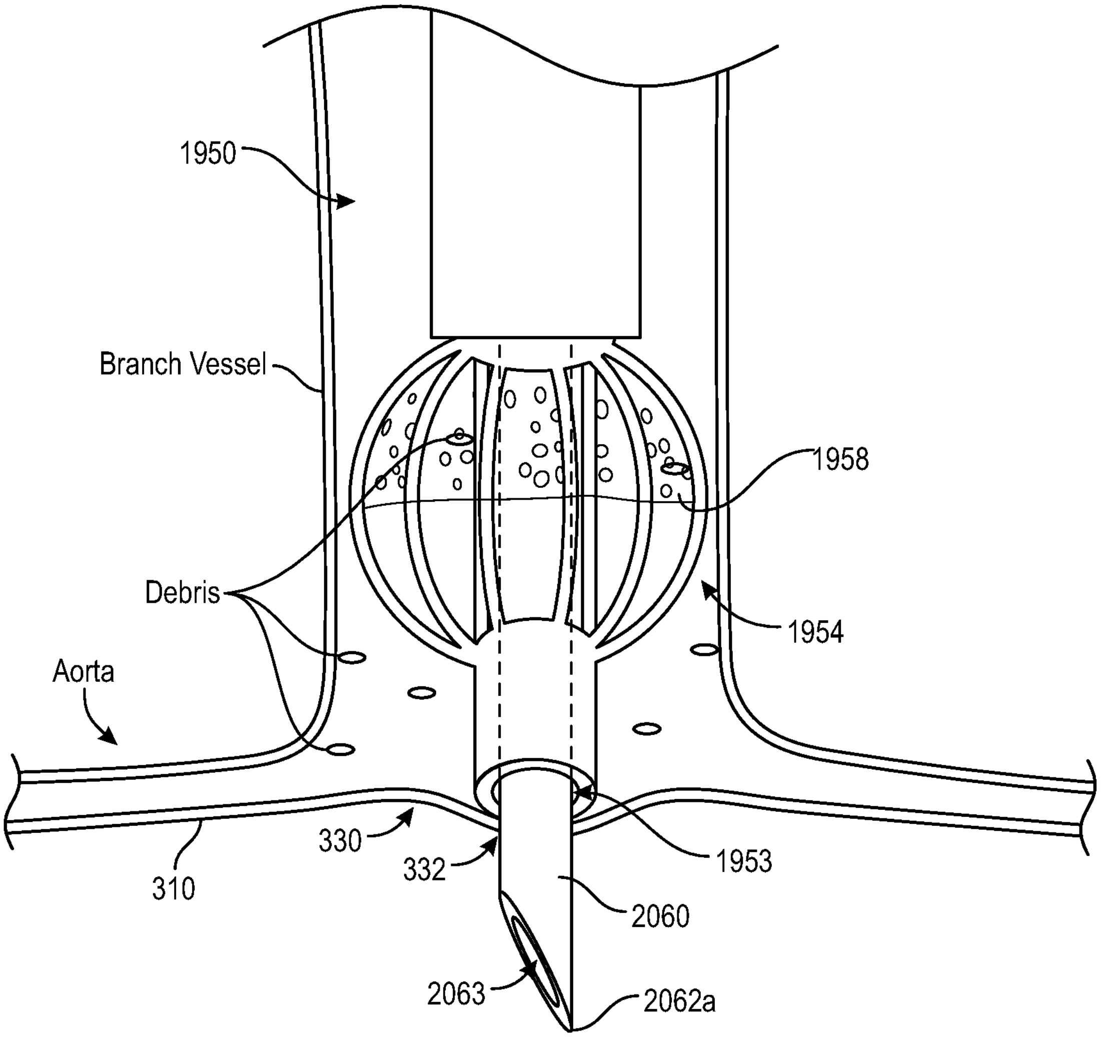
FIGS. 20A-21B are side views of respective cutting tools for forming in situ fenestrations through a base member of an aortic repair device, the cutting tools configured in accordance with embodiments of the present technology.
Figure 20B:
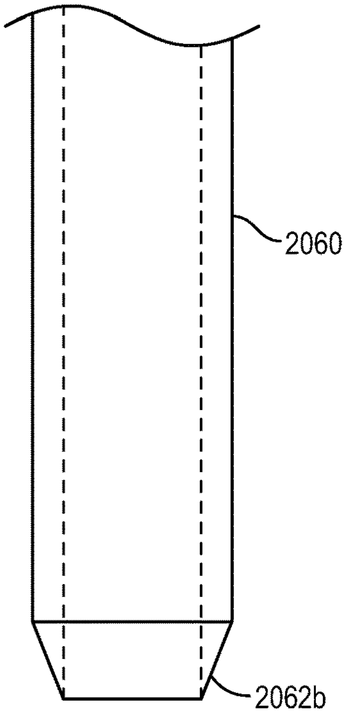
Figure 20C:
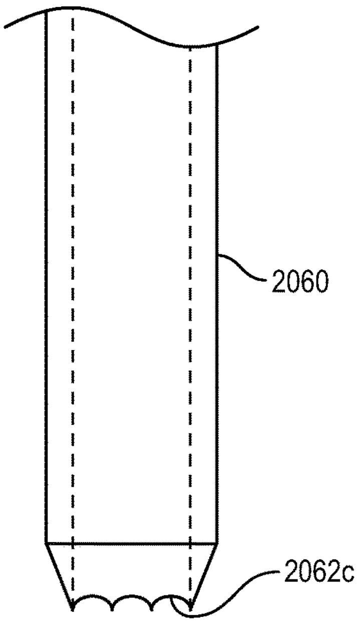
Figure 20D:
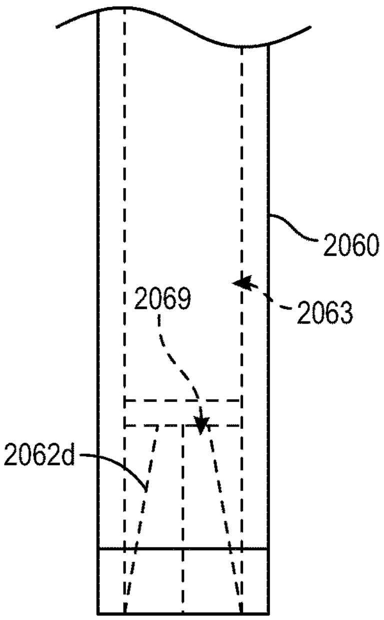

As shown in FIG. 20A, the cutting tool 2060 has pierced through the fenestration region 330 of the base member 310 to form an initial opening that will begin to define the fenestration 332. In some embodiments, the cutting tool 2060 includes a lumen 2063 that can be used to dispense fluid (e.g., saline, therapeutic agents, etc.) and/or deploy other tools, such as additional cutting tools or guidewire(s). In illustrated embodiment, debris from the base member 310 formed from moving the cutting tool 2060 through the base member 310 can be caught by the filter 1958, as described in detail with reference to FIG. 19. In these and/or other embodiments, the cutting tool 2060 can be used with any of the cutting zone tools and/or centering tools described herein. Additionally, although in FIG. 20A the cutting tool 2060 is illustrated piercing the base member 310 from the branch vessel toward the aorta, in other embodiments the cutting tool 2060 can be used to pierce the base member 310 from the aorta toward the branch vessel.

In FIG. 20A, the cutting feature 2062*a* is defined by a beveled or angled edge of the cutting tool 2060. In other embodiments, the cutting tool 2060 can include other cutting features. For example, in the embodiment illustrated in FIG. 20B, the cutting feature 2062*b* is defined by a chamfered edge ("chamfered edge 2062*b*") of the cutting tool 2060. The chamfered edge 2062*b* can be pressed against and/or rotated relative to a base member to form a fenestration therethrough. In the embodiment illustrated in FIG. 20C, the cutting feature 2062*c* includes one or more serrations ("serrations 2062*c*"). The serrations 2062*c* are expected to improve the cutting engagement with a base member and can be pressed against and/or rotated relative to the base member to form a fenestration therethrough. In the embodiment illustrated in FIG. 20D, the cutting feature 2062*d* includes one or more internal cutting fins ("cutting fins 2062*d*") positioned within the lumen 2063 of the cutting tool 2060. The cutting fins 2062*d* can be angled radially inward to define a central passage or opening 2069 between the cutting fins 2062*d* through which one or more tools (e.g., additional cutting tools, guidewires, and the like) can be inserted. Each of the cutting fins 2062*d* can be configured to form a generally or substantially linear incision through the base member about which the graft material of the base member can be bent or deflected.

Figure 21A:
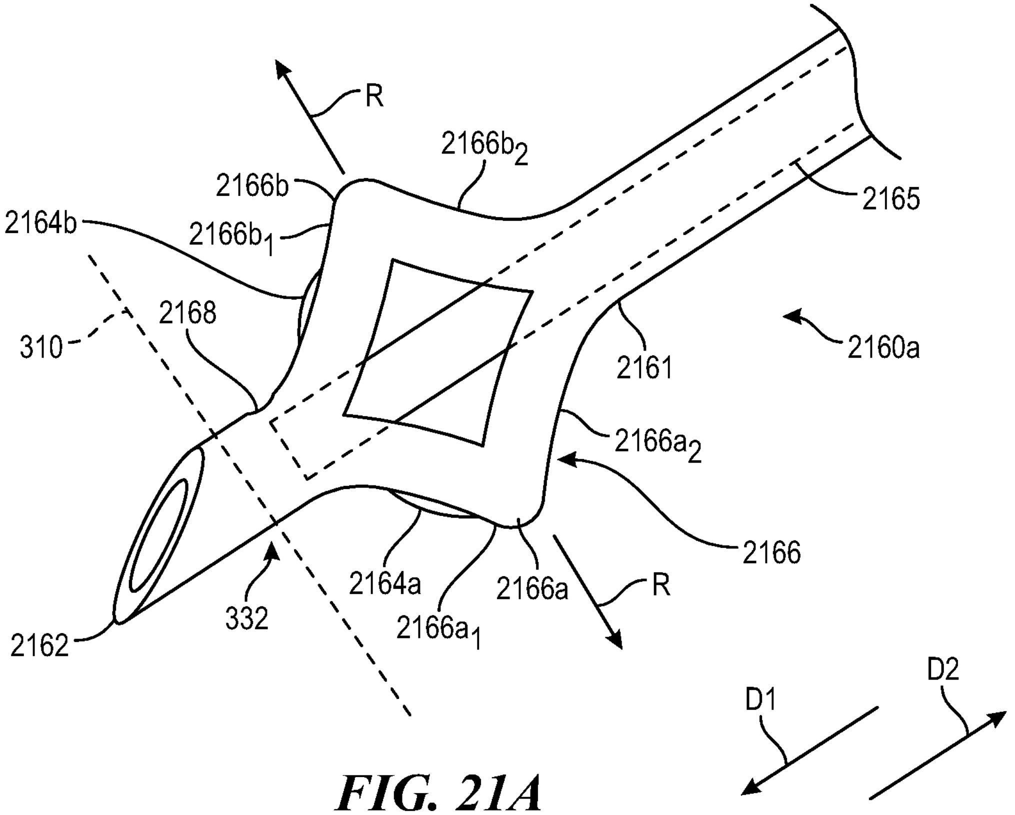
Figure 21B:
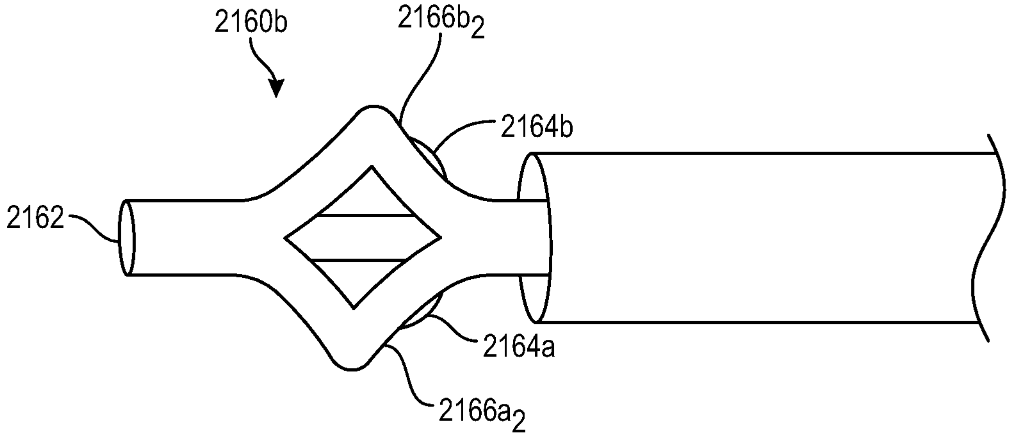

In the embodiment illustrated in FIG. 21A, the cutting tool 2160*a* includes one or more second cutting features 2164*a-b* positioned proximally from a first, distal cutting feature 2162. Each of the second cutting features 2164*a-b* can be carried by an expandable cutting member 2166 (also referred to as the "cage 2166"). In the illustrated embodiment, the cage 2166 includes a plurality of expandable arms or struts 2166*a-b* that bend or flex radially outward from a longitudinal axis of the cutting tool 2160*a*, such as in the direction indicated by the arrows R in FIG. 21A. Additionally, each of the struts 2166*a-b* can have a distal region 2166$a_1$, 2166$b_1$ and a proximal region 2166$a_2$, 2166$b_2$, individual ones of which can include a corresponding one of the second cutting features 2164*a-b*. In the illustrated embodiment, for example, the distal region 2166$a_1$ of the first strut 2166*a* includes one of the second cutting features 2164*a* and the distal region 2166$b_1$ of the second strut 2166*b* includes another of the second cutting features 2164*b*. Additionally, or alternatively, one or more of the proximal regions 2166$a_2$, 2166$b_2$ can include one or more of the second cutting features 2164*a-b*, such as shown with reference to cutting tool 2160*b* of FIG. 21B. In some embodiments, the cutting tool 2160*a* can include a recessed or narrowed region 2168 between the first cutting feature 2162 and the second cutting features 2164*a-b*.

The cage 2166 can be configured to transition from a first, low-profile delivery state to a second, expanded state (shown in FIG. 21A) by moving individual ones of the struts 2166*a-b* radially outward, such as in the direction indicated by the arrows R in FIG. 21A. In the illustrated embodiment, the struts 2166*a-b* are moved radially outward by moving an outer shaft portion 2161 of the cutting tool 2160*a* relative to an inner shaft portion 2165 of the cutting tool 2160*a* to drive expansion of the cage 2166. For example, the outer shaft portion 2161 can be moved toward the first cutting feature 2162 to compress the cage 2166 and cause radially outward flexing of the struts 2166*a-b*. In the second state, the cage

2166 and/or the second cutting features 2164*a*-*b* can define a greater dimension (e.g., width, diameter, and the like) than the first cutting feature 2162, as shown in FIG. 21A. In the first state, the cage 2166 and/or the second cutting features 2164*a*-*b* can define a dimension less than the first cutting feature 2162. In at least some embodiments, for example, the narrowed region 2168 can be configured such that, when the cutting tool 2160*a* is in the first state, the cage 2166 and/or the second cutting features 2164*a*-*b* are positioned radially inward relative to the first cutting feature 2162, such that the first cutting feature 2162 defines a maximum outer dimension of the cutting tool 2160*a*. In some aspects of the present technology, this can reduce or prevent the likelihood that the cage 2166 and/or the second cutting features 2164*a*-*b* will damage a tool, such as a catheter, used to deliver the cutting tool 2160*a* through a patient's vasculature.

During a fenestration procedure, one or both of the first cutting feature 2162 and the second cutting features 2164*a*-*b* can be used to initially penetrate the base member 310 and/or form the fenestration 332. In the embodiment illustrated in FIG. 21A, for example, the first cutting feature 2162 has been advanced in a first direction D1 toward and through the base member 310 to form an initial opening through the base member. The cage 2166 can be transitioned to the second, expanded state and the second cutting features 2164*a*-*b* can be used enlarge the initial opening to form the fenestration 332. For example, once the cage 2166 is in the second state, continued movement of the cutting tool 2160*a* in the first direction D1 can move the second cutting features 2164*a*-*b* into contact with and/or through the base member 310 to enlarge the initial opening and form the fenestration 332. In these and other embodiments, such as when the proximal regions 2166*$a_2$*, 2166*$b_2$* include one or more of the second cutting features 2164*a*-*b* as described with reference to FIG. 21B, the cage 2166 can be transitioned to the second state after the cage 2166 has passed through the base member 310 and moved in a second direction D2 opposite the first direction D1 (e.g., withdrawing the cutting tool 2160*a*-*b*) into contact with and/or through an interior surface of the base member 310 to enlarge the initial opening and form the fenestration 332.

Figure 22A:
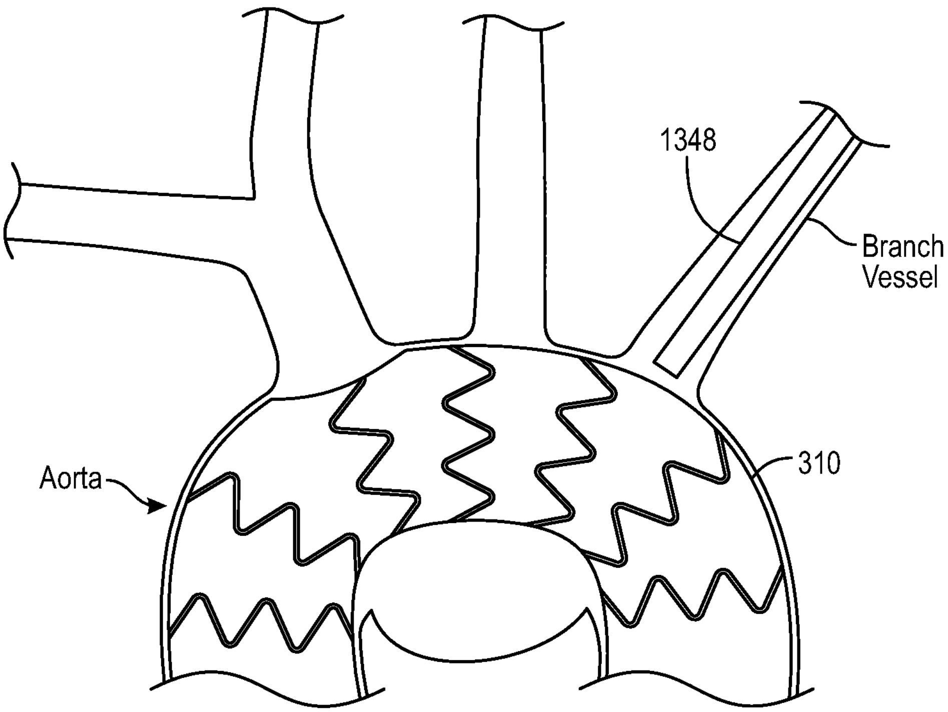
FIGS. 22A-22F are side views of select steps in a process for forming a fenestration in a base member in situ in accordance with embodiments of the present technology.
Figure 22B:
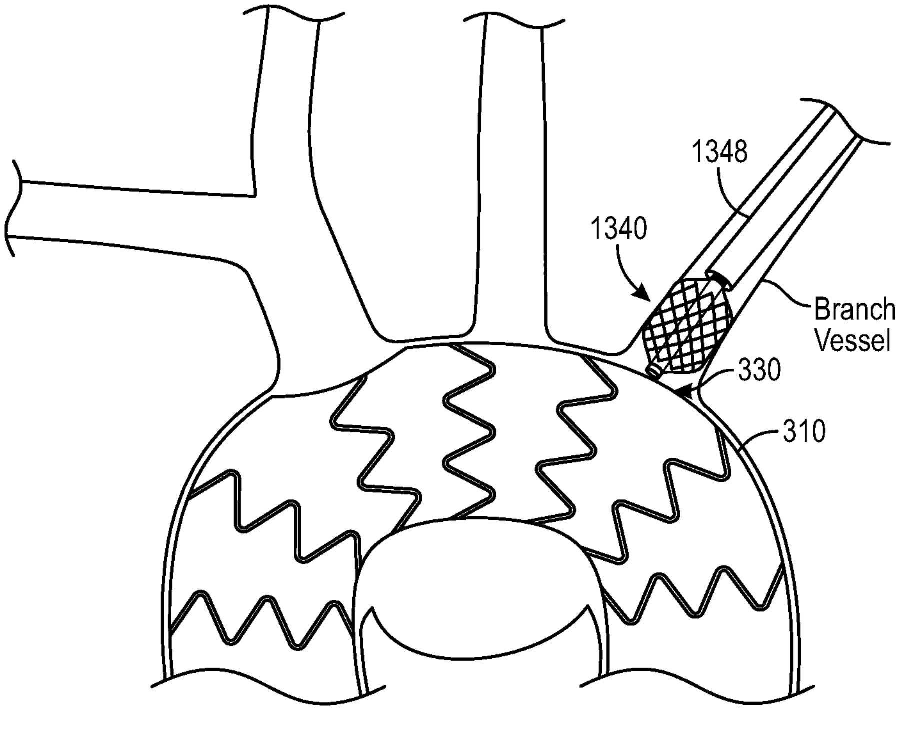

FIGS. 22A-22F are side views of select steps in a process for forming a fenestration in a base member in situ in accordance with embodiments of the present technology. Referring to FIG. 22A, a delivery sheath, such as the delivery sheath 1348 of FIG. 13, can be advanced through a branch vessel toward the aorta and/or the base member 310 positioned therein. As shown in FIG. 22B, a centering tool, such as the centering tool 1340 of FIG. 13, can be deployed from the delivery sheath 1348 and transitioned to the second state to center the centering tool 1340 within the branch vessel and/or relative to a fenestration region 330 of the base member 310.

Figure 22C:
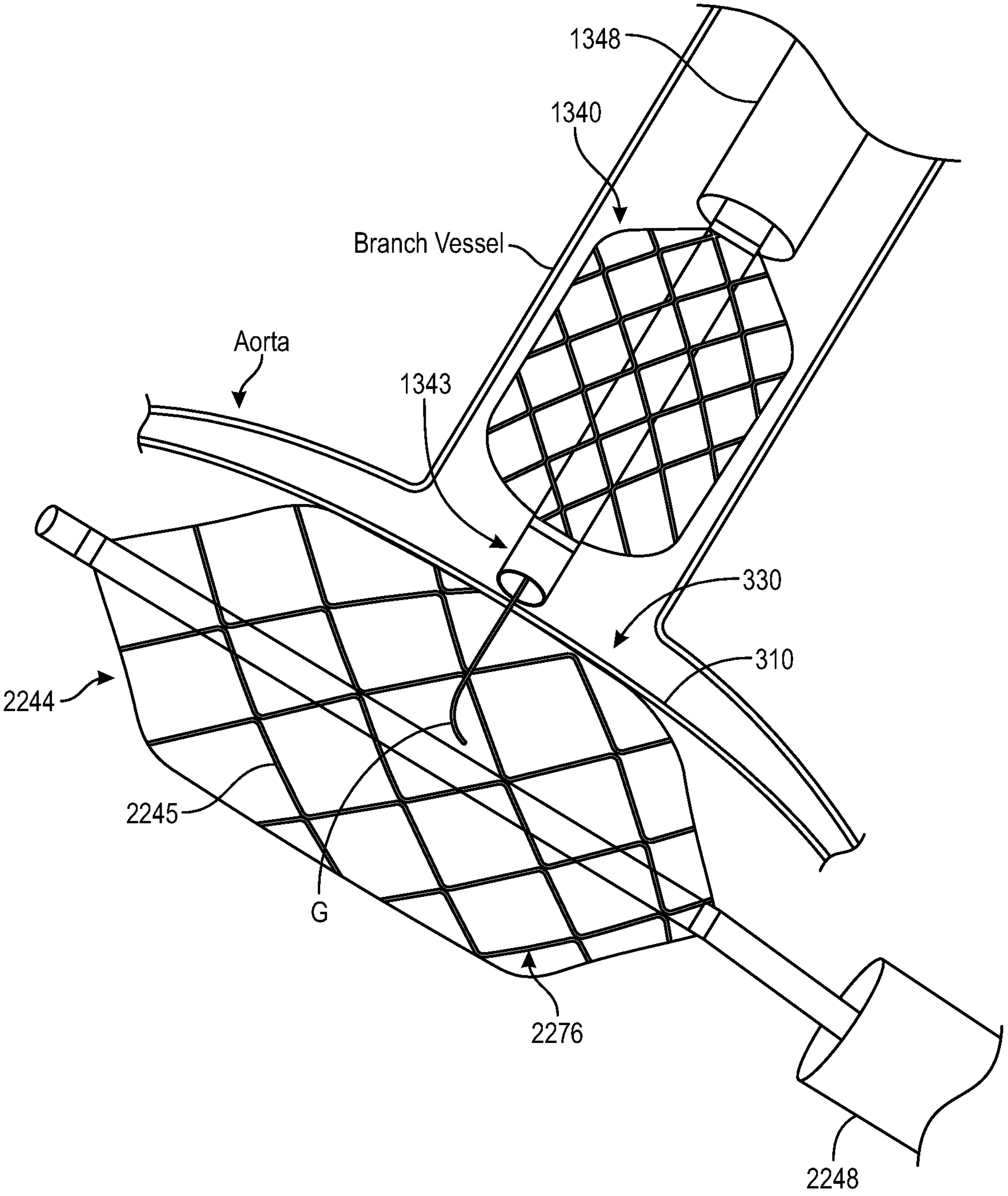

As shown in FIG. 22C, in some embodiments an expandable component 2244 can be positioned within the base member 310 and used to press the base member 310 toward and/or against the branch vessel and/or the centering tool. In the illustrated embodiment, the expandable component 2244 includes an expandable cage structure including one or more resilient struts 2245 (e.g., shape-memory material) defining one or more openings 2276. At least one of the openings 2276 can be aligned with the lumen 1343 of the centering tool 1340 such that a tool (e.g., a cutting tool) positioned within the centering tool 1340 can pass through the opening 2276, such as along guidewire G. For the sake of illustration, the expandable component 2244 is not shown in FIG. 22D or 22E. After the fenestration 332 (FIG. 22E) is formed, the expandable component 2244 can be transitioned to a low-profile delivery state and removed from the patient. The expandable component 2244 can be transitioned to the low-profile delivery state by, for example, retracting the expandable component 2244 into delivery sheath 2248 and/or advancing the delivery sheath 2248 over the expandable component 2244. In some embodiments, transitioning the expandable component 2244 to the low-profile delivery state can cause the expandable component 2244 to engage or otherwise capture (e.g., "grab") the guidewire G to place it in tension and, in some embodiments, draw the guidewire G proximally out of the patient to provide rail support to facilitate subsequent fenestration and/or delivery steps.

Figure 22D:
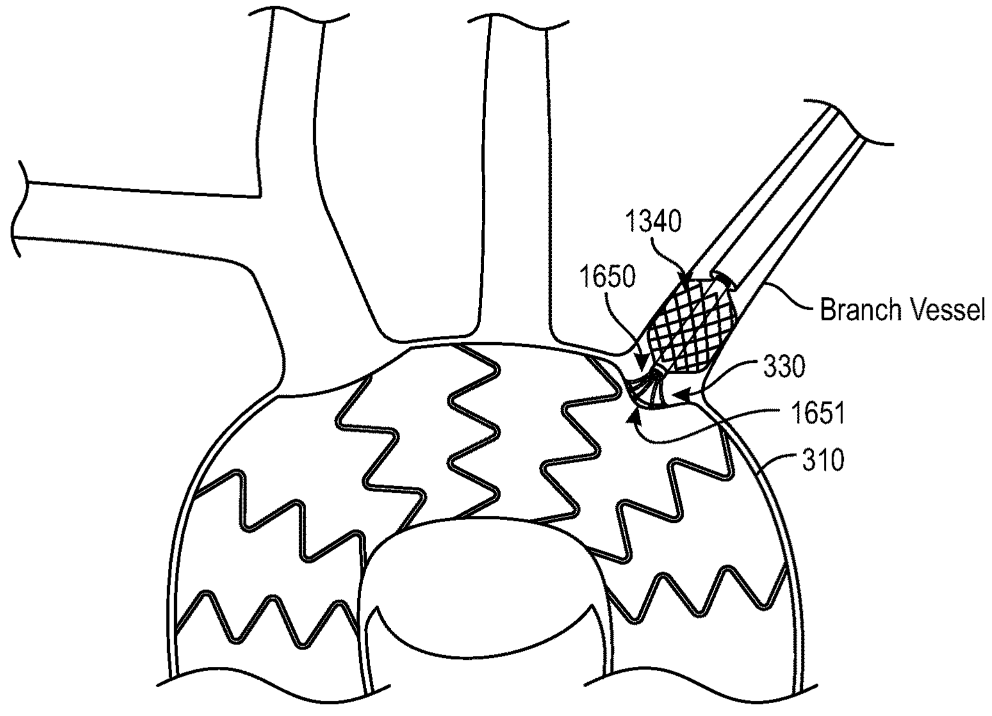
Figure 22E:
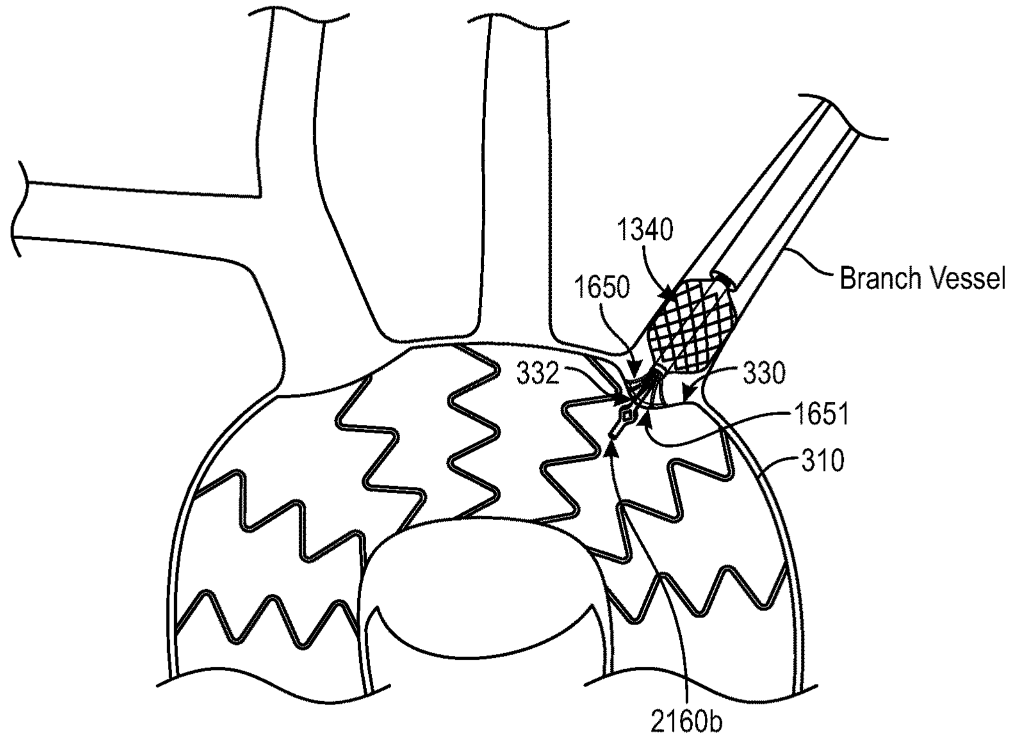

As shown in FIG. 22D, a cutting zone tool, such as the cutting zone tool 1650 of FIG. 16, can be advanced through the centering tool 1340 and pressed against the base member 310 to define the cutting zone 1651. As shown in FIG. 22E, a cutting tool, such as one or both of the cutting tool 2160*b*, can be advanced through the cutting zone tool 1650 to pierce the base member 310 and form the fenestration 332 in the fenestration region 330. In some embodiments, the cutting tool 2160*b* is advanced through a small or initial incision formed in the base member 310, transitioned to a second (e.g., expanded) state, and retracted through the base member 310 toward and/or into the cutting zone tool 1650 to form the fenestration 332. Because the cutting tool 2160*b* is retracted toward the cutting zone tool 1650, any debris created by forming the fenestration 332 is expected to be directed toward and/or into the cutting zone 1651 formed by the cutting zone tool 1650, such that the cutting zone tool 1650 can capture or receive all or substantially all the debris within the cutting zone 1651. Additionally, or alternatively, because the cutting tool 2160*b* is retracted toward the cutting zone tool 1650, the cutting zone tool 1650*c* (e.g., the funnel of the cutting zone tool) can surround the cutting tool 2160*b* to at least partially prevent the cutting tool 2160*b* from contacting/cutting the aorta and/or the branch vessel. In some embodiments, it is expected that cutting tools configured to cut through base members using a proximally-directed or "pulling" motion, such as described with reference to the cutting tool 2160*b* and FIG. 22E, can be easier to control and/or less likely to cause inadvertent injury to patients and/or equipment compared to other cutting tools, such as cutting tools configured to cut through base members using a distally-directed or "pushing" motion.

Figure 22F:
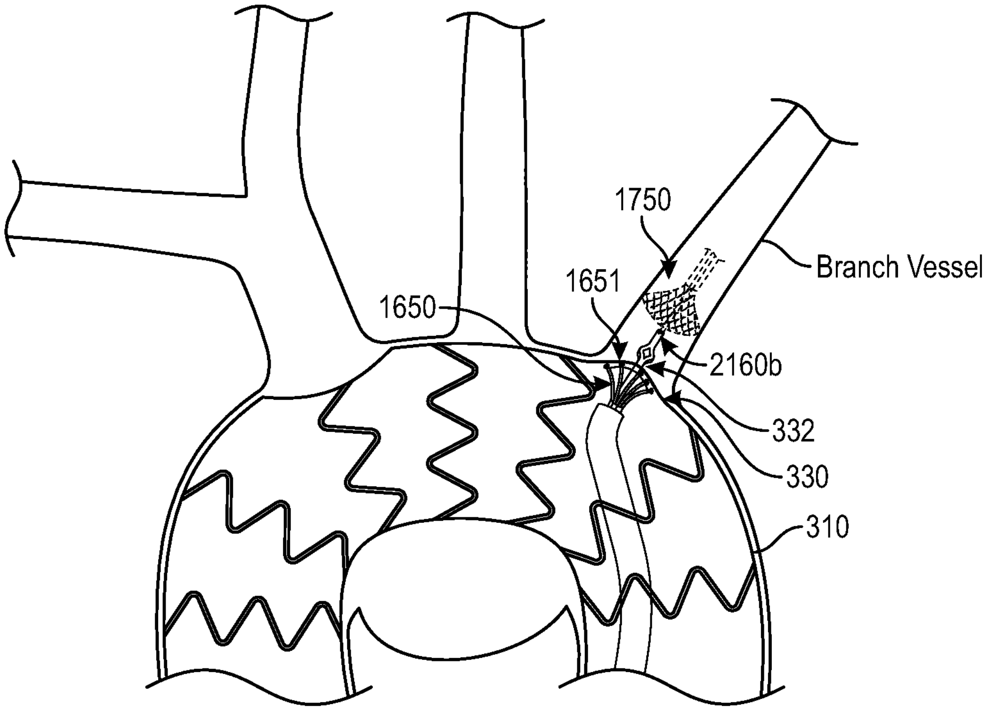

In some embodiments the cutting tools for the present technology can be used to form the fenestration 332 starting from within the base member 310. For example, as shown in FIG. 22F, the cutting tool 2160*b* can be advanced through the fenestration region 332 of the base member 310, toward and/or into the branch vessel to initially pierce the base member 310. In some embodiments, a cutting zone tool, such as the cutting zone tool 1750, can be advanced toward the base member 310 from within the branch vessel. The cutting zone tool can capture debris formed during fenestration and/or can shield the branch vessel from the cutting tool 2160*b*, e.g., to prevent the sharp surfaces of the cutting tool 2160*b* from coming in contact with the branch vessel or other portions of the patient's anatomy. The cutting zone tool 1750 is shown distal of the branch vessel ostium to better illustrate the cutting tool 2160*b*, but it will be appreciated that, in at least some embodiments, the cutting zone tool 1750 can be positioned near or through the branch vessel ostium, e.g., pressed against or proximate the fenestration region 332 of the base member 310. In some instances, this initial piercing of the base member 310 can form the fenestration. In these and/or other instances, the cutting tool 2160*b* can then be expanded and pulled back through the base member, e.g., to form the fenestration 332. The cutting zone tool 1650 can be used to press at least a portion of the base member 310 toward and/or into the branch vessel, e.g., to assist with forming the fenestration 332. Additionally, or alternatively, the cutting zone tool 1650 can be used to form the cutting zone 1651 to capture all, or at least a portion, debris from the base member 310 and/or other material created when fenestrating the base member 310.

D. Selected Embodiments of Grasper Tools

FIGS. 23A-26C illustrate grasper tools 2380 configured in accordance with embodiments of the present technology. The grasper tools 2380 can include some features that are at least generally similar in structure and function, or identical in structure and function to one another, and/or can operate in a generally similar or identical manner to one another. Moreover, one or more of the different features of the grasper tools 2380 of the present technology can be combined with each other and/or omitted. The grasper tools 2380 can be used in tandem with one or more of the other tools described herein. Each of the grasper tools 2380 can be configured to "grasp" or otherwise engage a base member, such as the base member 310, as described in greater detail with reference to FIGS. 24A-24C.

Figure 23A:
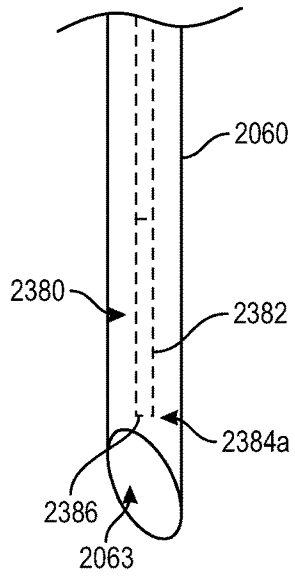
FIGS. 23A-26C are side views of respective grasper tools configured in accordance with embodiments of the present technology.

Referring to FIG. 23A, the grasper tool 2380 includes an adjustable portion 2382. The adjustable portion 2382 can comprise a shape memory material, such as nitinol, and can be configured to change state/shape. In FIG. 23A, the adjustable portion 2382 is positioned within the lumen 2063 of the cutting tool 2060 and has a first, generally linear/elongate state 2384*a* ("first state 2384*a*"). In some embodiments, the lumen 2063 of the cutting tool 2060 can be configured to constrain/hold the adjustable portion 2382 in the first state 2384*a*, such that advancing the adjustable portion 2382 out of/beyond the lumen 2063 can allow the adjustable portion 2382 to transition from the first state 2384*a* to another state. Additionally, or alternatively, the grasper tool 2380 can be positioned within one or more of the other tools described herein, such as one or more of the centering tools, cutting zone tools, and/or another suitable tool. In these and other embodiments, the adjustable portion 2382 can include a tip or terminus 2386, which can be configured to cut or pierce at least partially though a base member, such as the base member 310, or another base member described herein.

Figure 23B:
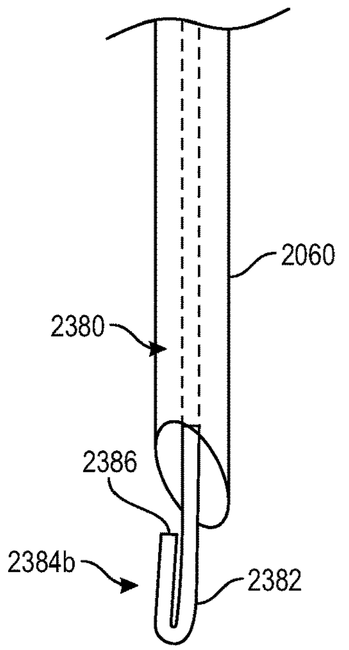
Figure 23C:
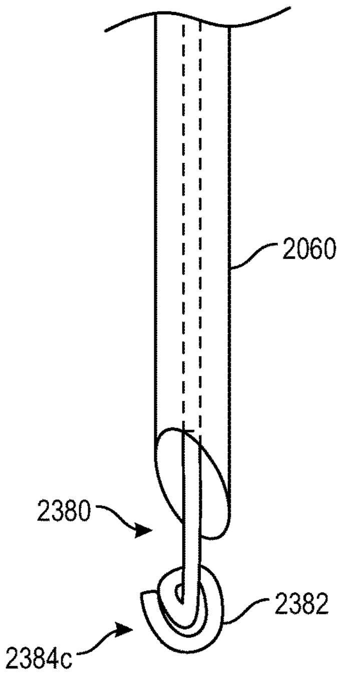
Figure 23D:
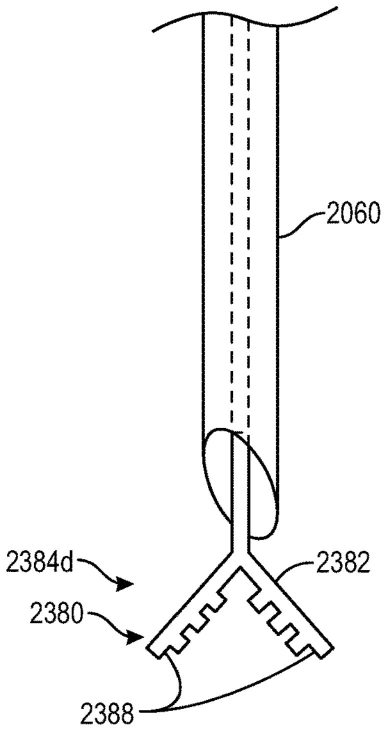

FIGS. 23B-23D illustrate respective states 2384*b-d* to which the adjustable portion 2382 can be configured to transition. In some embodiments, the adjustable portion 2382 is configured to transition from the first state 2384*a* to one of the other states 2384*b-d*. In other embodiments, the adjustable portion 2382 is configured to transition between any two or more of the states 2384*a-d*. Referring to FIG. 23B, the adjustable portion 2382 has a second, hook-shaped state 2384*b* ("second state 2384*b*") in which at least part of the adjustable portion 2382 curves back toward the cutting tool 2060 such that the tip 2386 faces toward the cutting tool 2060. In some embodiments, the cutting tool 2060 and/or the grasper tool 2380 can be advanced through a base member, such as the base member 310, in a first location, and then the adjustable portion 2382 can be transitioned to the second state 2384*b*. In the second state 2384*b*, the tip 2386 can be retracted back toward the base member to pierce through the base member at a second location, for example, to hook the base member and allow the base member to be manipulated via the grasper tool 2380.

Referring to FIG. 23C, the adjustable portion 2382 has a third, coiled state 2384*c* ("third state 2384*c*"). In the third state 2384*c*, the adjustable portion can have a greater outer dimension (e.g., diameter) than the cutting tool 2060 and/or than the first state 2384*a*. Accordingly, the adjustable portion 2382 can be advanced to contact a surface (e.g., inner or outer) of the base member and used to push, pull, or otherwise manipulate the base member.

Referring to FIG. 23D, the adjustable portion 2382 has a fourth state 2384*d* in which the adjustable portion 2382 includes a plurality of pincers or engagement members 2388 configured to engage or grasp at least a portion of a base member, such as the base member 310. In the illustrated embodiment the adjustable portion 2382 includes two engagement members 2388 in the fourth state 2384*d*. In other embodiments, the adjustable portion 2382 can include more engagement members 2388. The engagement members 2388 can be configured to engage/grasp a base member without or substantially without piercing through the base member. This is described in further detail with reference to FIGS. 24A-26C.

Figure 24A:
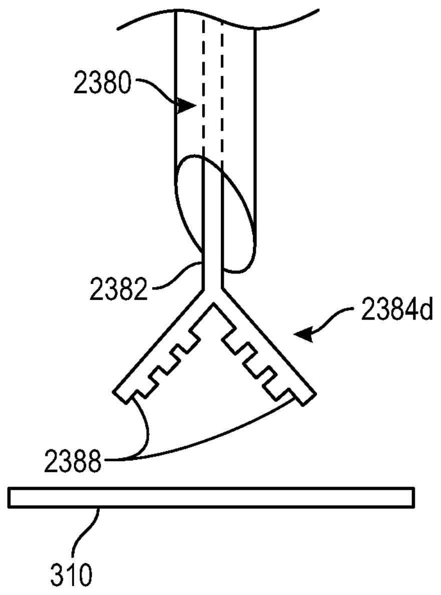
Figure 24B:
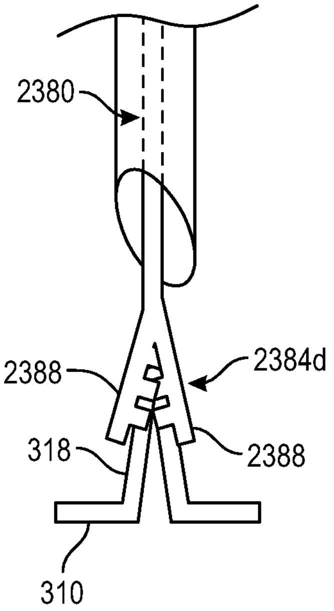
Figure 24C:
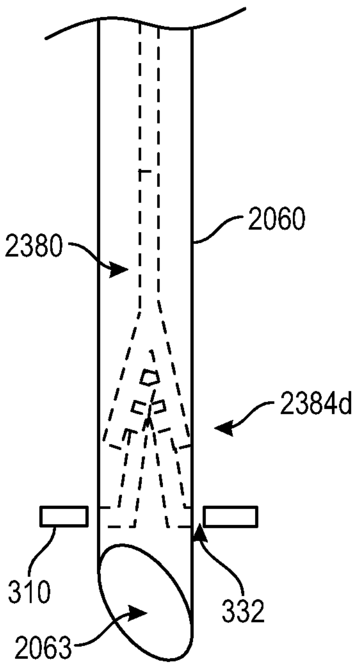

Referring to FIG. 24A, the grasper tool 2380 can be used during a procedure to form a fenestration through a base member, such as the base member 310. In the illustrated embodiment, for example, with the adjustable portion 2382 in the fourth state 2384*d*, the engagement members 2388 can be advanced toward the base member 310 through the cutting tool 2060. Referring to FIG. 24B, the engagement members 2388 can engage or grasp at least a portion of the base member 310, such as a portion of the graft material 318 of the base member 310. Referring to FIG. 24C, with the engagement members 2388 grasping the base member 310, the engagement members 2388 can be retracted back within the lumen 2063 of the cutting tool 2060. This movement of the engagement members 2388 can pull the base member 310 into contact with the cutting tool 2060 to thereby form a fenestration 332 through the base member 310. Continued movement of the engagement members 2388 can fully withdraw the grasper tool 2380 and the grasped portion of the base member 310 from the cutting tool 2060. Although described with respect to the fourth state 2384*d* and the associated engagement members 2388, the method illustrated in FIGS. 24A-24C can also be performed with the second state 2384*b* (FIG. 23B) and/or the third state 2384*c* (FIG. 23C) of the adjustable portion 2382.

Figure 25A:
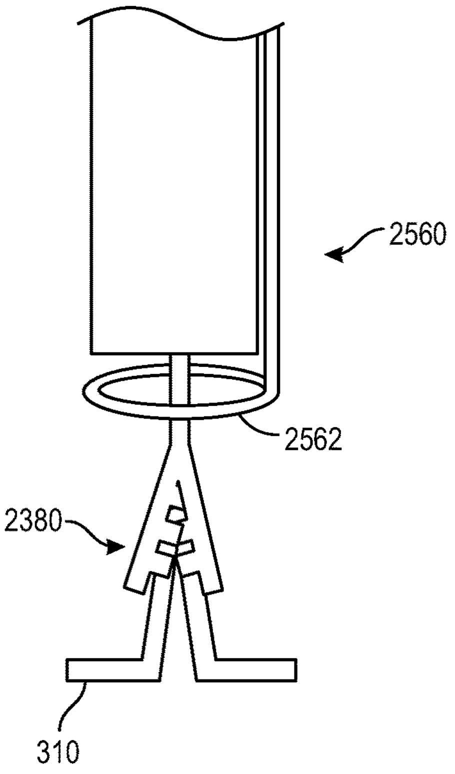
Figure 25B:
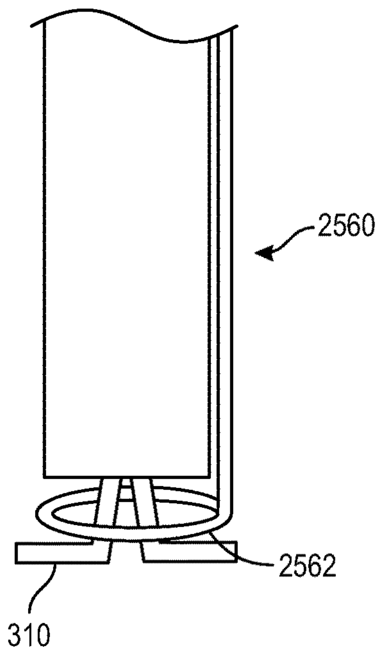
Figure 25C:
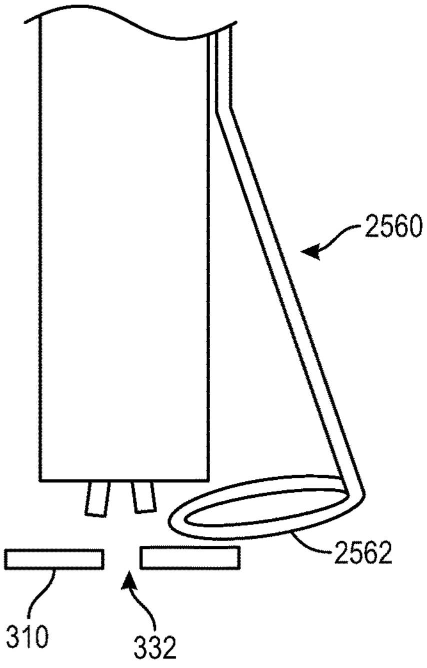
Figure 26A:
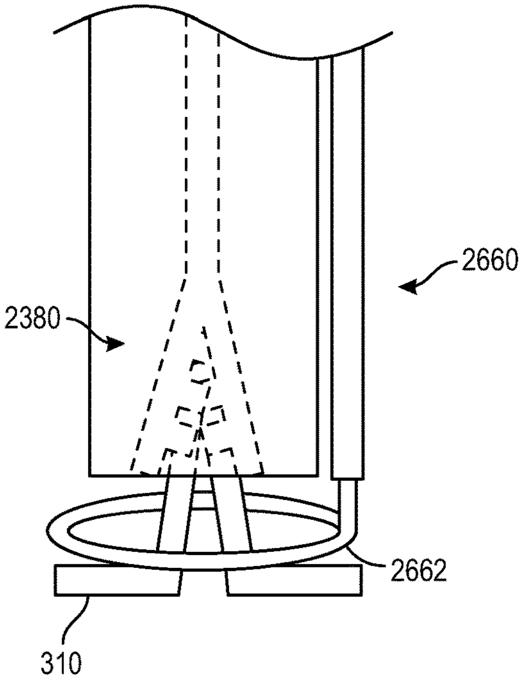
Figure 26B:
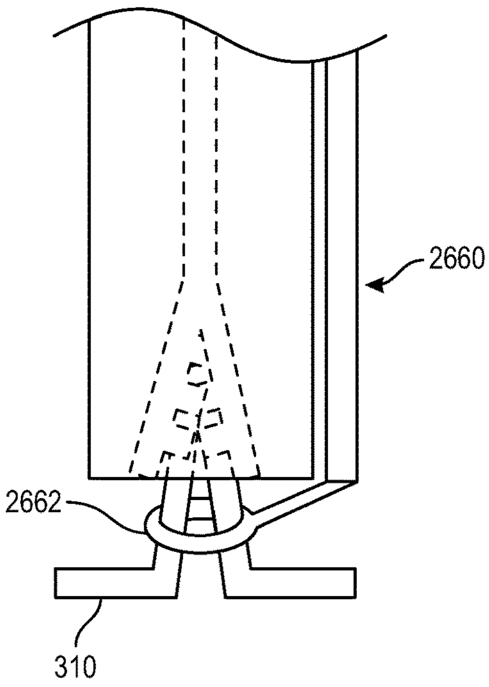
Figure 26C:
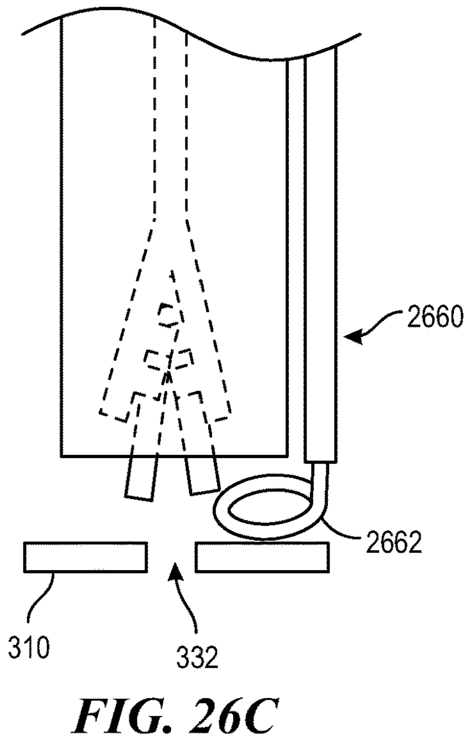

FIGS. 25A-26C illustrated additional tools that can be used with the grasper tool 2080 to form fenestrations in base members in accordance with embodiments of the present technology. Specifically, FIGS. 25A-25C illustrate a cutting tool 2560 and FIGS. 26A-26C illustrate another cutting tool 2660. Referring to FIG. 25A, the cutting tool 2560 includes a circular cutting ring or feature 2562. The grasper tool 2080 can engage at least a portion of the base member 310, as described in further detail with reference to FIGS. 23A-24C. Referring to FIG. 25B, the grasper tool 2080 can be used to draw the base member 310 toward the circular cutting feature 2562, for example, until at least part of the base member 310 is positioned within and/or extends through the circular cutting feature 2562. With portion of the base member 310 in this position, the circular cutting feature 2562 can be moved (e.g., laterally) relative to the base member 310 to cut through the base member 310 and form the fenestration 332 therethrough, as shown in FIG. 25C.

Referring to FIG. 26A, the cutting tool 2660 includes a circular cutting ring or feature 2662 at least generally similar to the circular cutting feature 2562 of FIGS. 25A-25C. Additionally, the circular cutting feature 2662 can be configured to tighten or close around a grasped portion of the base member 310. The grasper tool 2380 can be used to engage a portion of the base member 310 and draw the engaged portion of the base member 310 through the circular cutting feature 2662, as shown in FIG. 26A. With the engaged portion of the base member 310 in this position, the circular cutting feature 2662 can be tightened, which can bring the circular cutting feature 2662 into contact with the base member 310, as illustrated in FIG. 26B. Continued tightening of the circular cutting feature 2662 can cause the circular cutting feature 2662 to cut through the base member 310 and form the fenestration 332 therethrough, as shown in FIG. 26C. Additionally, or alternatively, the circular cutting feature 2662 can be electrically conductive and configured to deliver electrical current to the base member 310 to form the fenestration 332.

As described in detail above, one or more of the fenestration tools described with reference to FIGS. 8-26C can also be configured to approach the fenestration region from inside the base member. For example, a centering tool can be pressed against an inner surface of the wall of the base member so it tents outwards and can be moved until the tented portion of the base member extends into the branch vessel. After an initial fenestration is created, another centering tool can be extended from inside the base member into the branch vessel. A balloon, braid, or other expandable member on the centering tool can be inflated in the branch vessel to center the centering tool within the branch vessel. Then, an expandable component mounted on a catheter or tube which can slide over the outside of the centering tool can be expanded within the base member and advanced to push the wall of the base member against the ostium of the branch vessel. Additionally, or alternatively, a cutting zone tool can be pressed against an inner surface of the base member to form a protected cutting zone therewith. Then, a cutting tool can be advanced through the cutting zone tool toward the base member and/or into a branch vessel and used to form a fenestration through the base member. In these and other embodiments, a grasper tool can be used to grasp a portion of the inner surface of the base member, for example, to assist with fenestrating the base member.

V. SELECTED EMBODIMENTS OF BRANCH MEMBERS

FIGS. 27-30 illustrate various branch members 2720, 2820, 2920, and 3020, respectively, configured in accordance with embodiments of the present technology. The branch members 2720, 2820, 2920, 3020 can include some features that are at least generally similar in structure and function, or identical in structure and function, to one another and/or the branch member 320 of FIG. 3B, and/or can operate in a generally similar or identical manner to one another and/or the branch member 320 of FIG. 3B. For example, the branch members 2720, 2820, 2920, 3020 can each include a stent frame and a graft material that together form a conduit through which blood can be diverted. Moreover, one or more of the different features of the branch members 2720, 2820, 2920, 3020 of the present technology can be combined and/or omitted.

Each branch member 2720, 2820, 2920, 3020 can include an elongate portion 2722, 2822, 2922, 3022 sized and shaped to engage an interior vessel wall and a coupling portion 2724, 2824, 2924, 3024 extending radially outwardly from an end region of the elongate portion 2722, 2822, 2922, 3022. The elongate portion 2722, 2822, 2922, 3022 can have a first outer dimension (e.g., width, diameter, etc.), and the coupling portion 2724, 2824, 2924, 3024 can have a second outer dimension greater than the first outer dimension. The coupling portion 2724, 2824, 2924, 3024 can couple the branch member 2720, 2820, 2920, 3020 to a base member through a fenestration in the base member, such as one of the base members 310*a*-*c* of FIGS. 3A-3F, any of the base members described herein with reference to FIGS. 4A-7, or another suitable base member. Additionally, each of the branch members 2720, 2820, 2920, 3020 can be expandable from a first, low-profile delivery state to a second, deployed state (shown in FIGS. 27-30, respectively). In some embodiments, the elongate portion 2722, 2822, 2922, 3022 and the coupling portion 2724, 2824, 2924, 3024 can be separately expandable, e.g., so that one of the elongate portion 2722, 2822, 2922, 3022 or the coupling portion 2724, 2824, 2924, 3024 can be expanded at a first time and the other of the elongate portion 2722, 2822, 2922, 3022 or the coupling portion 2724, 2824, 2924, 3024 can be expanded at a second time after the first time. During a deployment procedure, the branch member 2720, 2820, 2920, 3020 can be expanded from the first state to the second state and coupled to the base member to perfuse the branch vessel. In at least some embodiments, for example, the coupling portion 2724, 2824, 2924, 3024 can be expanded, coupled to, and/or sealed against the inner surface of the base member. In some aspects of the present technology, the increased outer dimension of the coupling portion 2724, 2824, 2924, 3024 relative to the elongate portions 2722, 2822, 2922, 3022 and the fenestration can improve the attachment and/or sealing engagement between the branch member 2720, 2820, 2920, 3020 and the base member.

Figure 27:
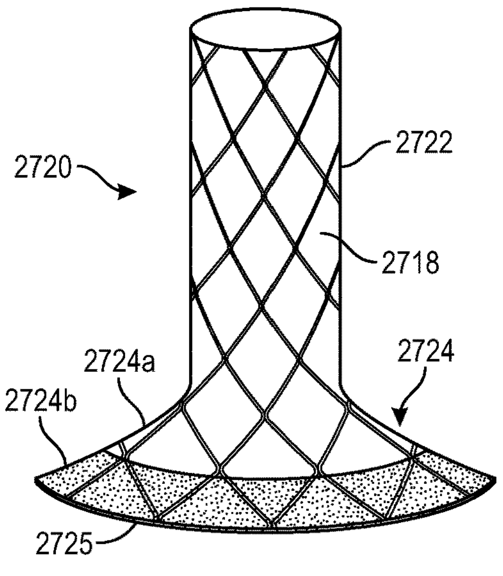
FIGS. 27-31 are respective side views of branch members of an aortic repair device configured in accordance with embodiments of the present technology.

In the embodiment illustrated in FIG. 27, the elongate portion 2722 and the coupling portion 2724 include a braided or mesh structure formed from a plurality of interwoven or interconnected filaments (e.g., a stent frame) attached to a graft material. The coupling portion 2724 includes a first region 2724*a* and a second region 2724*b*. The first region 2724*a* can be proximate to the elongate portion 2722, and the second region 2724*b* can be between the first region 2724*a* and an outer perimeter 2725 of the coupling portion 2724. Accordingly, the second region 2724*b* can define an outer annular rim of the coupling portion 2724. In the illustrated embodiment, the elongate portion 2722 and the first region 2724*a* of the coupling portion 2724 are coated with graft material 2718, and the second region 2724*b* of the coupling portion 2724 is not coated with the graft material 2718. In some aspects of the present technology, branch members with coupling portions that have graft material-free regions have a reduced likelihood of inducing tissue growth that covers or occludes neighboring branch arteries.

Figure 28:
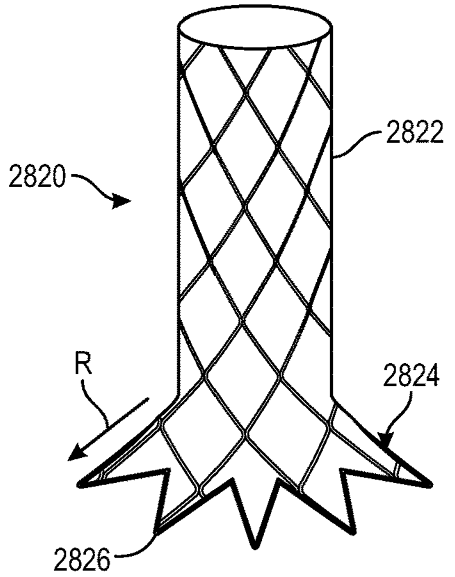

Referring to FIG. 28, the elongate portion 2822 and the coupling portion 2824 includes a braided or mesh structure formed from a plurality of interwoven or interconnected filaments, a plurality of spaced apart stent elements (e.g., circular stent rings connected to a graft material), a balloon-expandable structure, and/or other suitable frame structures. Additionally, the coupling portion 2824 includes one or more elongate units or cells 2826 that flare radially outward from the elongate portion 2822, such as in the direction indicated by arrow R. In some aspects of the present technology, the cells 2826 are expected to improve the fit and/or seal between the coupling portion 2824 and the base member when the branch member 2820 is in the second state. For example, individual ones of the cells 2826 can be deflectable or movable independently, or at least generally independently, of one or more other cells 2826 to allow each of the cells 2826 in the coupling portion 2824 to flexibly conform to the base member.

Figure 29:
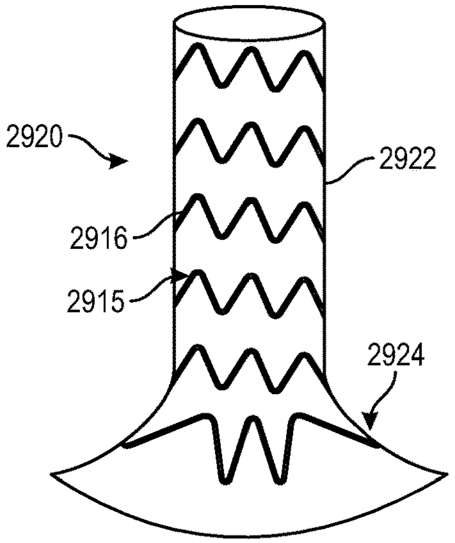

Referring to FIG. 29, the elongate portion 2922 and the coupling portion 2924 can include a stent structure 2915 having a plurality of struts 2916 extending as circular rings around the circumference of the elongate portion 2922, such as Z-stents, any of the struts 416*a-e* described in detail with reference to FIGS. 4A-4E, or other suitable struts.

Figure 30:
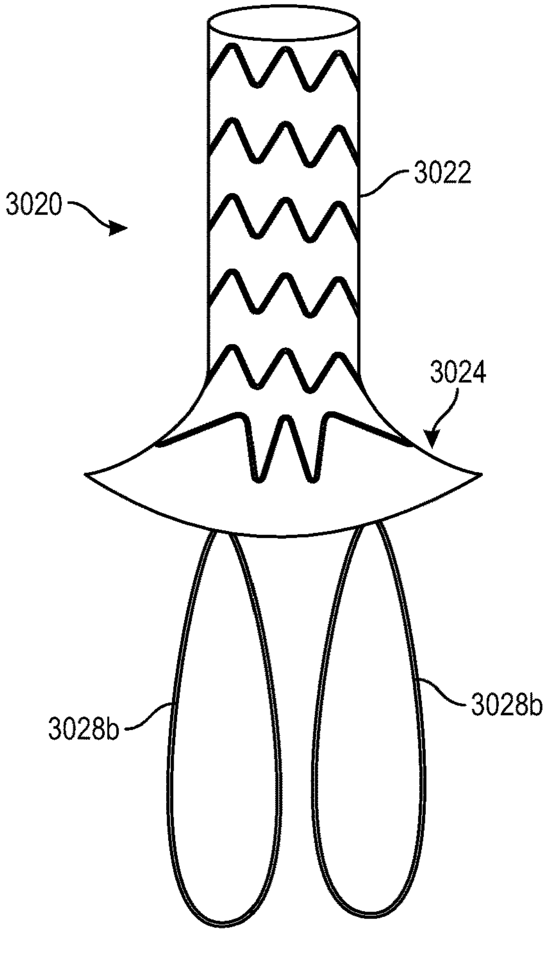

In the embodiment illustrated in FIG. 30, the branch member 3020 has features generally similar to the branch member 2920 of FIG. 29 and can additionally include one or more base member coupling features 3028*a-b* (also referred to as "coupling loops 3028*a-b*"). In the illustrated embodiment, the coupling features 3028*a-b* are rings or loops of semi-rigid material (e.g., wire, stent material, a filament) configured to engage the body of a base member. For example, the coupling loops 3028*a-b* can be sized to extend around the exterior of the base member. The branch member 3020 can first be positioned within the branch vessel such that the coupling members extend into the aortic arch before transitioning the branch member 3020 to the second state. The base member can then threaded through the coupling loops 3028*a-b* and, upon expansion of the base member, the coupling loops 3028*a-b* secure the base member to the outer surface of the branch member 3020. The coupling portion 3024 can expand within the interior of the base member or external to the base member. For example, after the coupling loops 3028*a-b* have been positioned around the base member, the coupling portion 3024 can be positioned within the base member and expanded. In some embodiments, the coupling loops 3028*a-b* can be deployed within the lumen of the base member via the fenestration, and the outward force of the deployed loops 3028*a-b* on the inner wall of the base member can frictionally secure the two components together. In some aspects of the technology, the coupling features 3028*a-b* can improve the stability and/or reduce the motion of the branch member 3020 relative to the base member to which it is coupled and, in turn, reduce the likelihood of fracture and/or separation between the branch member 3020 and the base member.

Figure 31:
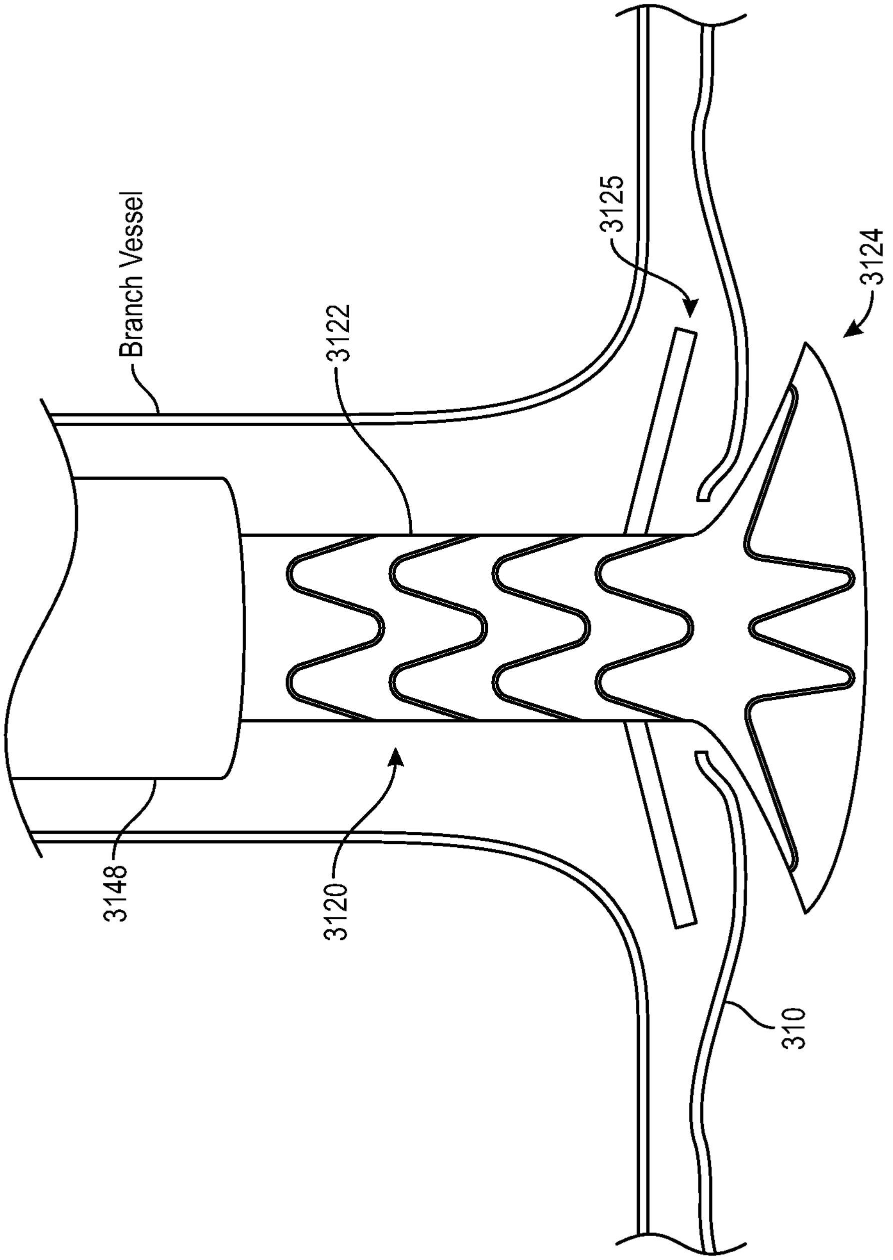

FIG. 31 illustrates another branch member 3120 configured in accordance with embodiments of the present technology. The branch member 3120 can be generally similar or identical in structure and/or function to one or more of the branch members described in detail with reference to FIGS. 27-30. As shown in FIG. 31, the branch member 3120 includes a second radially flared coupling portion 3125 spaced proximal to the first radially flared coupling portion 3124 by a distance and configured to engage the outer surface of the base member 310. When deployed, the first and second flared coupling portions 3124, 3125 can sandwich a portion of the sidewall of the base member 310 surrounding the fenestration. This is expected to enhance the seal between the base member 310 and branch member 3120, increase the mechanical fixation strength of the base member 310 and branch member 3120, and/or reduce or prevent the first flared coupling portion 3124 from moving inwardly to extend into the central lumen of the base member 310 due to motion, migration, or mispositioning of the branch member 3120. This dual-sided engagement of the base member 310 can be of particular use when it is difficult, or not possible, to closely align the fenestration of the base member with the ostium of the branch vessel (e.g., using one or more of the center tools described further herein with reference to FIGS. 8-15B), for example, due to aneurysmal expansion of the aorta, dissection of the aorta, or other anatomic variations of the aorta or branch vessel.

During delivery, the second flared coupling portion 3125 can be compressed within a delivery sheath or cover sleeve 3148 and extend in the proximal direction. During implantation, the cover sleeve 3148 can be withdrawn to deploy the first flared coupling portion 3124 within the base member 310. The first flared coupling portion 3124 can be positioned against the inner wall of the base member 310, and continued movement of the cover sleeve 3148 can deploy the second flared coupling portion 3125, e.g., external to the base member 310, to pinch or "sandwich" at least a portion of the base member 310 between the first flared coupling portion 3124 and the second flared coupling portion 3125. Further continued movement of the cover sleeve 3148 can deploy the elongate portion 3122 of the branch member 3120 within the branch vessel.

Figure 32A:
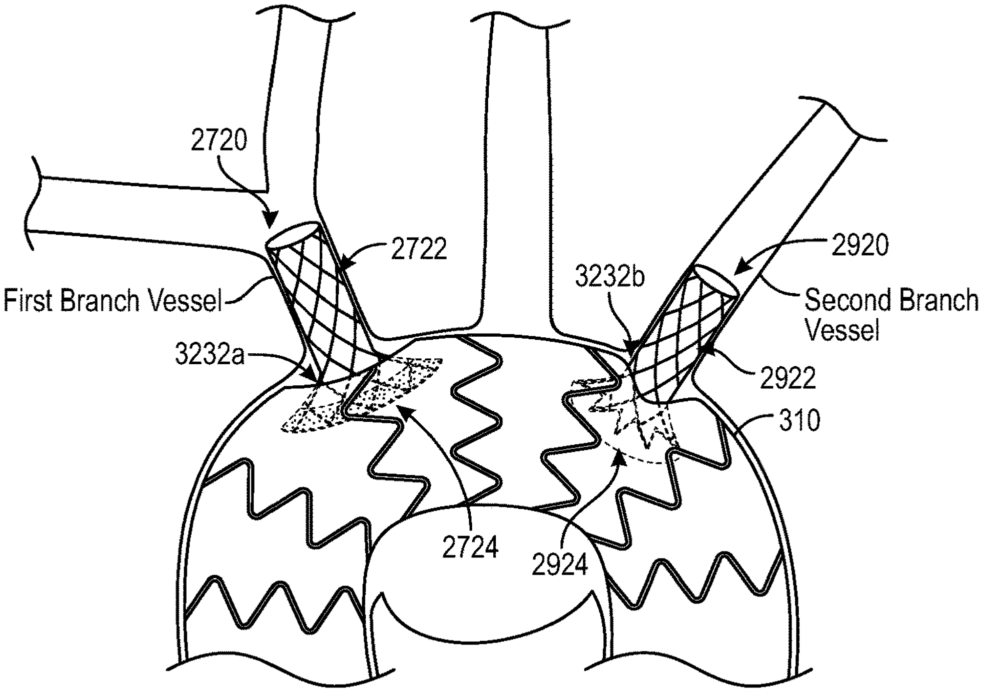
FIGS. 32A and 32B are respective side views of two branch members coupled to a base member positioned within an aortic arch in accordance with embodiments of the present technology.

FIG. 32A is a side view of the branch members 2720, 2920 of FIGS. 27 and 29, respectively, coupled to the base member 310 in accordance with embodiments of the present technology. The branch member 2720 is positioned through a preformed fenestration 3232*a* in the base member 310. The elongate portion 2722 of the branch member 2720 extends proximally into a first branch vessel (e.g., the brachiocephalic artery). The coupling portion 2724 of the branch member 2720 is coupled to a portion of the inner surface of the base member 310 proximate the preformed fenestration 3232*a*. The branch member 2920 is positioned through a fenestration 3232*b* formed in situ in the base member 310, such as described in detail with reference to FIGS. 20A-26C. The elongate portion 2922 of the branch member 2920 extends distally into a second branch vessel (e.g., the left subclavian artery). The coupling portion 2924 of the branch member 2920 is coupled to a portion of the inner surface of the base member 310 proximate the in situ fenestration 3232*b*.

Figure 32B:
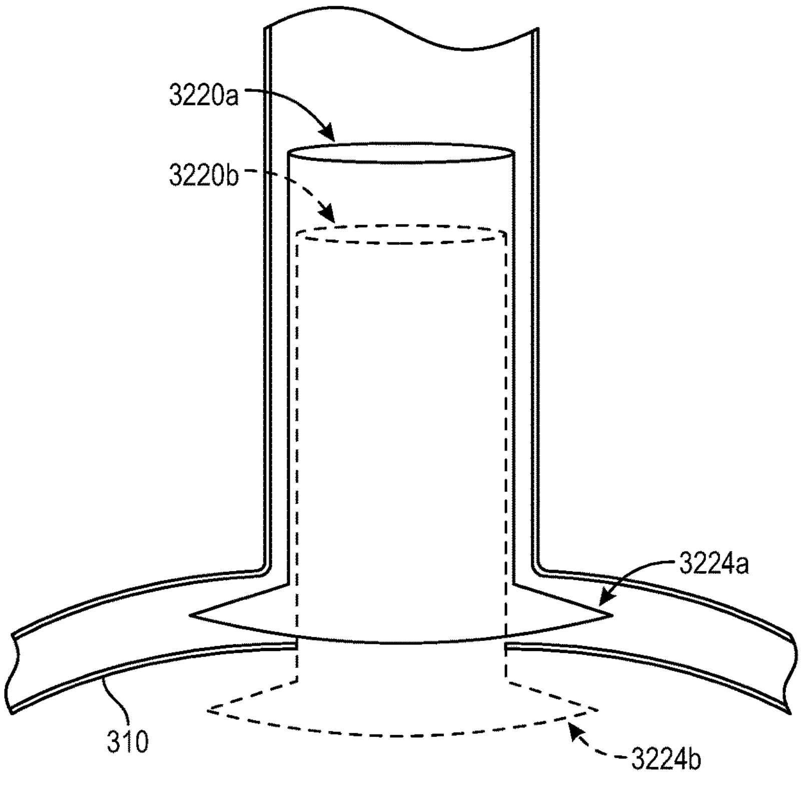

Referring to FIG. 32B, in some embodiments, a first branch member 3220*a* (including, for example, any one or more of the branch members described herein with reference to FIGS. 3B, 3E, 3F, and 27-31) can be deployed with the flared coupling portion contacting 3224*a* the exterior of the base member 310. Then a second branch member 3220*b* (including, for example, any one or more of the branch members described herein with reference to FIGS. 3B, 3E, 3F, and 27-31; shown in dashed-line in FIG. 32B) can inserted through the first branch member 3220*a* and be deployed with the flared coupling portion 3224*b* inside the base member 310, and the second branch member 3220*b* could be pulled back so that the wall of the base member 310 is tightly sandwiched between the flared coupling portions 3224*a-b* of the two branch members 3220*a-b*.

VI. SELECTED EMBODIMENTS OF FENESTRATION METHODS

Figure 33A:
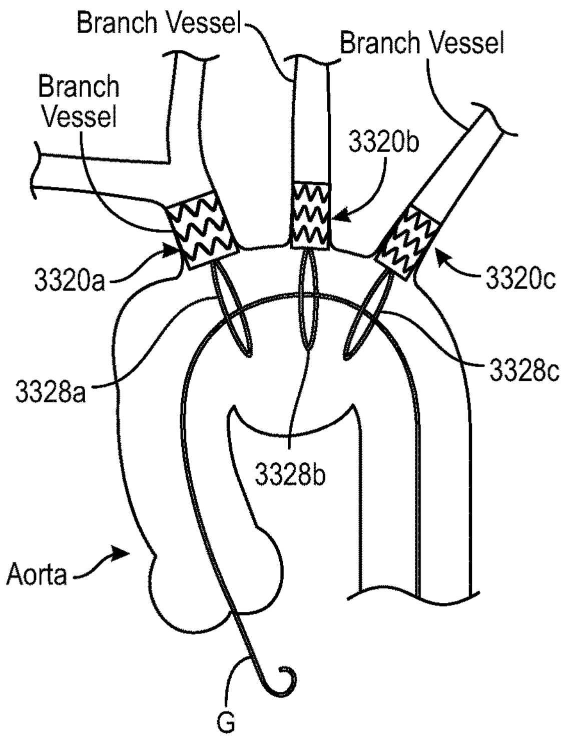
FIGS. 33A-33D are side views of select steps in a process for coupling the branch member of FIG. 30 with a base member in situ in accordance with embodiments of the present technology.

FIGS. 33A-33D are side views of select steps in a process for coupling one or more branch members 3320*a-c* with a base member 3310 in situ, in accordance with embodiments of the present technology. Referring to FIG. 33A, one or more branch members 3320*a-c* can be positioned within a respective branch vessel of the patient's aorta. In the illustrated embodiments, individual ones of the branch members 3320*a-c* include one or more coupling features 3328*a-c*, which can be at least generally similar to the coupling features 3028*a-b* described in detail with reference to FIG. 30. For the branch members 3320*a-c* that include coupling features 3328*a-c* with loop shapes, a guidewire G can be threaded through individual ones of the loop-shaped coupling features 3328*a-c*, as shown in FIG. 33A.

Figure 33B:
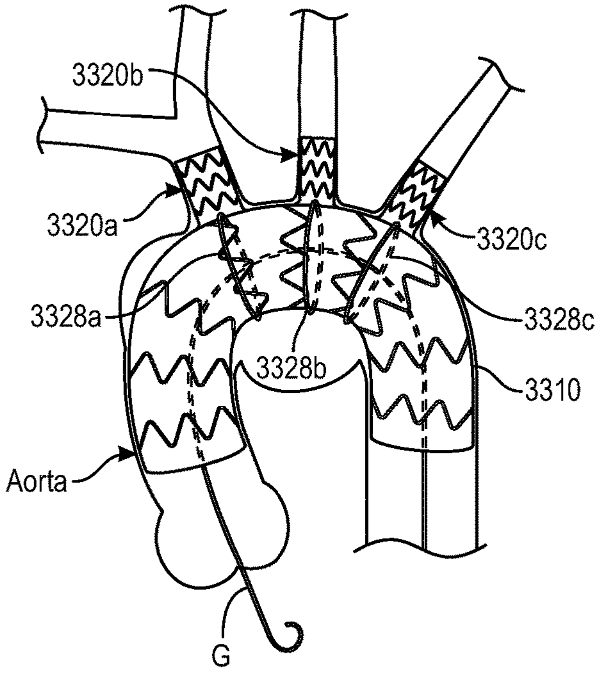

Referring to FIG. 33B, the base member 3310 can be introduced into the aorta over the guidewire G and transitioned to the second (expanded) state, as shown in FIG. 33B. Because the guidewire G was fed through the coupling features 3328*a-c* (FIG. 33A), introducing the base member 3310 into the aorta over the guidewire G can include feeding the base member 3310 through individual ones of the coupling features 3328*a-c*. Accordingly, when the base member 3310 is expanded to the second state, the exterior of the base member 3310 can contact individual ones of the coupling features 3328*a-c* and hold the base member 3310 relative to individual ones of the corresponding branch members 3320*a-c*. In some aspects, this can improve the alignment of the branch members 3320*a-c* with the base member 3310 and/or reduce movement of the base member 3310 relative to individual ones of the branch members 3320*a-c*.

Figure 33C:
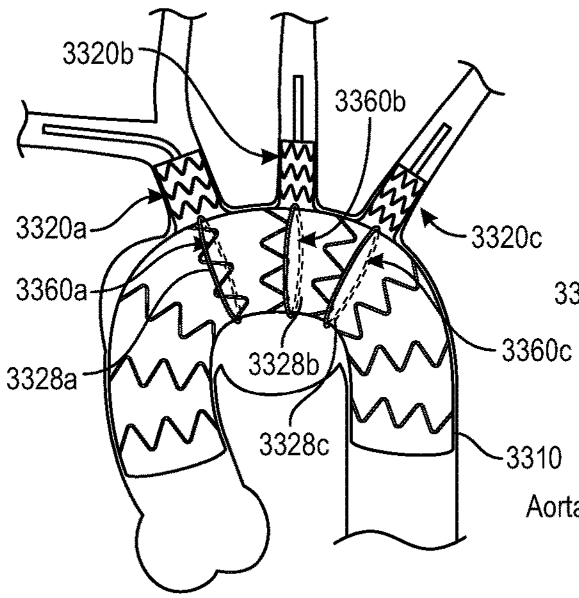

Referring to FIG. 33C, one or more cutting tools 3360*a-c* can be delivered through individual ones of the branch members 3320*a-c* and used to pierce the base member 3310. Individual ones of the cutting tools 3360*a-c* can include any of the cutting tools described in detail with reference to FIGS. 20A-26C, or another suitable cutting tool. In some embodiments, individual ones of the coupling features 3328*a-c* can compress the base member 3310 against the respective branch members 3320*a-c* and provide a counterforce that makes piercing the base member 3310 with individual ones of the cutting tools 3360*a-c* easier. After individual ones of the cutting tools 3360*a-c* pierce the base member 3310, the resulting holes through the base member 3310 can be enlarged or dilated, for example, using one or more additional cutting tools.

Figure 33D:
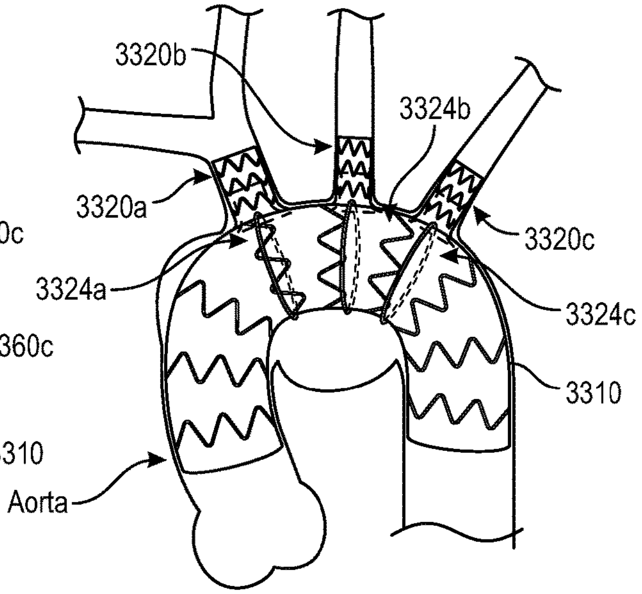

Referring to FIG. 33D, coupling portions 3324*a-c* of the branch members 3320*a-c* can be expanded to the second state and used to couple individual ones of the branch members 3320*a-c* to the base member 3310. Individual ones of the coupling portions 3324*a-c* can include any of the coupling portions described in detail with reference to FIGS. 27-31, or another suitable coupling portion. In some embodiments, coupling the branch members 3320*a-c* to the base member 3310 includes forming a substantially fluid-impermeable seal between individual ones of the branch members 3320*a-c* and the base member 3310, such that substantially all the fluid (e.g., blood) that enters the aorta passes through one of the branch members 3320*a-c* and/or the base member 3310 without leaking into the aorta between the base member 3310 and one of the branch members 3320*a-c*.

Figure 34A:
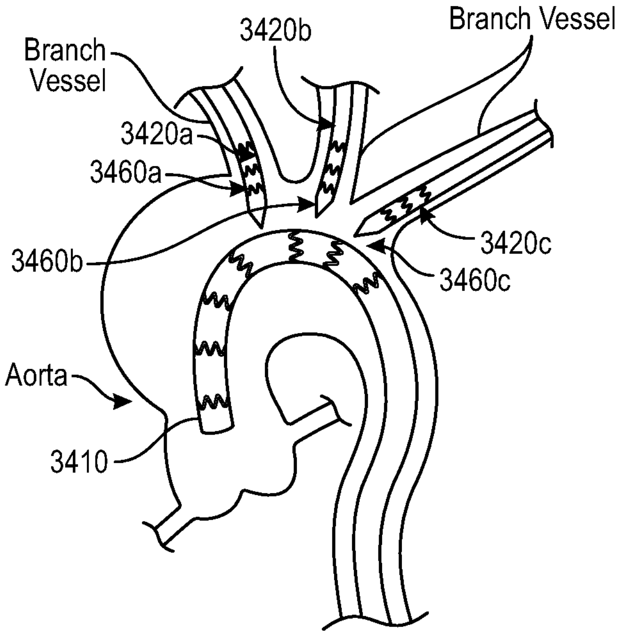
FIGS. 34A-34C are side views of select steps in a process for fenestrating a base member of an aortic repair device in situ in accordance with embodiments of the present technology.
Figure 34B:
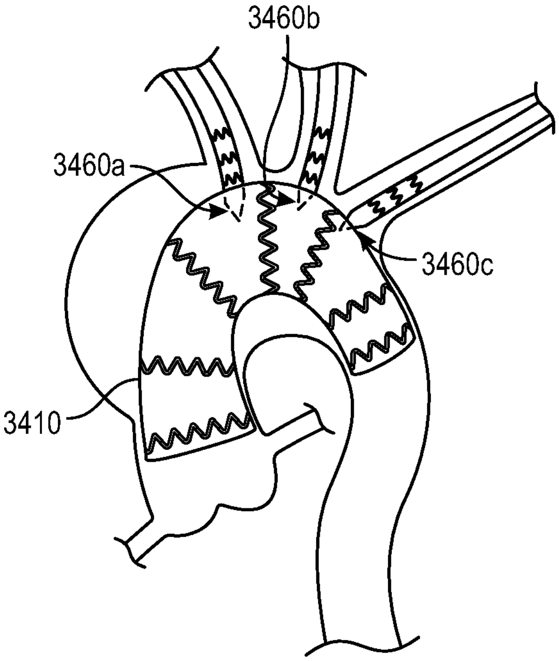
Figure 34C:
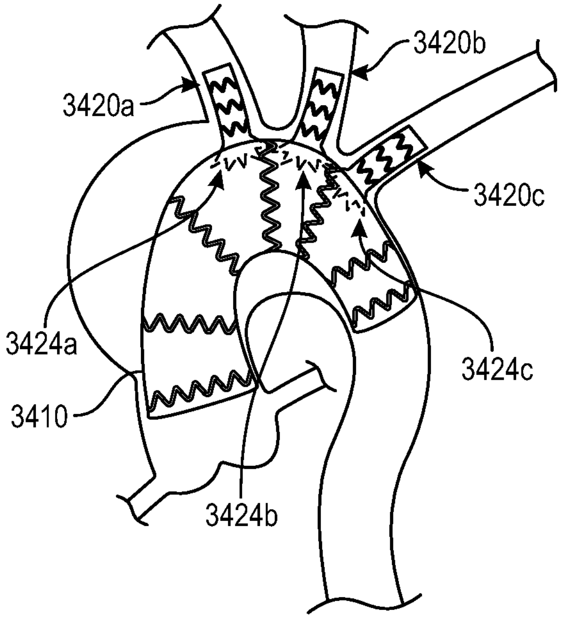

FIGS. 34A-34C are side views of select steps in a process for fenestrating a base member 3410 in situ in accordance with embodiments of the present technology. Referring to FIG. 34A, the base member 3410 can be positioned within the aorta in the first state. One or more cutting tools 3460*a-c* can be inserted through respective branch arteries and extend at least partially into the aorta. Individual ones of the cutting tools 3460*a-c* can include any of the cutting tools described in detail with reference to FIGS. 20A-26C, or another suitable cutting tool. In the illustrated embodiment, one or more branch members 3420*a-c* are inserted along with individual ones of the cutting tools 3460*a-c*. Individual ones of the branch members 3420*a-c* can include any of the branch members described in detail with reference to FIGS. 27-31, or another suitable branch member.

Referring to FIG. 34B, the base member 3410 can be expanded to the second state. The base member 3410 can contact individual ones of the cutting tools 3460*a-c* as it expands, which can cause the cutting tools 3460*a-c* to pierce through (e.g., fenestrate) the base member 3410. In some embodiments, one or more of the cutting tools 3460*a-c* can be a sharpened tip or edge of a delivery catheter for the branch members 3420*a-c*. After fenestrating the base member 3410, individual ones of the branch members 3420*a-c* can be expanded to the second state, as shown in FIG. 34C, and individual coupling portions 3424*a-c* of the branch members 3420*a-c* can be coupled to the base member 3410. Accordingly, fenestrating the base member 3410 (FIG. 34B) can simultaneously align the branch members 3420*a-c* (FIG. 34C) relative to the base member 3410 and the fenestrations formed by the cutting tools 3460*a-c*.

VII. EXAMPLES

Several aspects of the present technology are described in the following examples:

1. An aortic repair device for treating an aortic arch of a patient, the aortic repair device comprising:
   a base member having a first end portion and a second end portion opposite the first end portion, the base member comprising—
   - a stent structure having a plurality of struts extending around a perimeter of the base member;
   - a graft material coupled to the stent structure and configured to define an enclosed conduit through at least a portion of the stent structure; and
   - a fenestration region at least partially between the first end portion and the second end portion, wherein the fenestration region is sized and shaped to align with at least one branching vessel from the aortic arch, and wherein the fenestration region is configured to be pierced to form a fenestration in the base member when the base member is positioned within the aortic arch.
2. The aortic repair device of example 1 wherein the stent structure comprises a mobile stent portion configured to move independent from adjacent portions of the stent structure and independent from the graft material, and wherein the mobile stent portion is positioned along the fenestration region.
3. The aortic repair device of example 1 or example 2 wherein the plurality of struts comprises (i) a first plurality of struts made from a first material and (ii) a second plurality of struts made from a second material more penetrable than the first material, and wherein the second plurality of struts are positioned along the fenestration region.
4. The aortic repair device of example 3 wherein the first material is a metal.
5. The aortic repair device of example 3 or example 4 wherein the second material is a polymer.
6. The aortic repair device of example 1 wherein the plurality of struts comprises (i) a first plurality of struts extending fully around the perimeter of the base member, and (ii) a second plurality of struts extending around only a portion of the perimeter of the base member to define a stent-free section along the perimeter of the base member, and wherein the stent-free section aligns at least in part with the fenestration region.
7. The aortic repair device of any of examples 1-6 wherein the base component is formed from a first material having a first fenestration resistance and a second material having a second fenestration resistance less than the first fenestration resistance, and wherein the second material is positioned along the fenestration region.

8. The aortic repair device of any of examples 1-7 wherein the graft material includes a first portion and a second portion radially aligned with the first portion, wherein at least one of the first portion and the second portion are configured to deflect radially inwardly into the enclosed conduit of the base member.

9. The aortic repair device of any of examples 1-8, further comprising a branch perfusion member including a proximal region and a distal region, wherein the proximal region is coupled to the fenestration region of the base member, and wherein the distal region extends radially outward from the base member toward the at least one branching vessel.

10. The aortic repair device of example 9 wherein at least a portion of the distal region is positioned within the at least one branching vessel.

11. The aortic repair device of example 9 or example 10 wherein the proximal region sealingly engages the base member to at least partially prevent fluid within the base member from leaking between the base member and the branch perfusion member.

12. An aortic repair system for treating an aortic arch of a patient, the aortic repair system comprising:

a base member, comprising— a main body having a first end portion and a second end portion, wherein the main body defines a fluid conduit, and wherein the first end portion defines a first fluid opening;

a septum extending through the main body from the second end portion of the main body toward the first end portion of the main body, wherein the septum divides the fluid conduit into a primary lumen having a first cross-sectional area and a secondary lumen having a second cross-sectional area less than the first cross-sectional area, and wherein the second end portion of the main body defines a second fluid opening for the primary lumen; and a leg extending form the second end portion of the main body, wherein the leg defines a leg lumen fluidly coupled to the secondary lumen, and wherein the leg has an end portion defining a third fluid opening for the secondary lumen;

a spanning member configured to be coupled to the second end portion of the main body, the spanning member defining a spanning member lumen configured to be fluidly coupled to the primary lumen via the second fluid opening, wherein the spanning member includes a fenestration region sized and shaped to align with at least one branching vessel from the aortic arch, and wherein the fenestration region is configured to be pierced to form a fenestration in the spanning member to perfuse the at least one branching vessel.

13. The aortic repair system of example 12 wherein:

the base member is configured to be implanted within an ascending portion of the aortic arch with the leg positioned in a first branching vessel from the aortic arch, and the spanning member is configured to extend from the base member toward and/or into a descending portion of the aortic arch to align the fenestration region with a second branching vessel from the aortic arch different than the first branching vessel.

14. The aortic repair system of example 12 or example 13 wherein:

the base member is implanted within an ascending portion of the aortic arch with the leg positioned in a first branching vessel from the aortic arch, and the spanning member is coupled to the second end portion of the base member and extends from the base member toward and/or into a descending portion of the aortic arch to align the fenestration region with a second branching vessel from the aortic arch different than the first branching vessel.

15. The aortic repair system of example 13 or example 14 wherein:

the first branching vessel is a brachiocephalic artery of the patient, and the second branching vessel is a left common carotid artery or a left subclavian artery of the patient.

16. The aortic repair system of any of examples 12-15 wherein the base member is a first base member having a first main body defining a first fluid conduit, a first septum, and a first leg, the aortic repair system further comprising:

a second base member, comprising— a second main body having a third end portion and a fourth end portion, wherein the second main body defines a second fluid conduit, and wherein the third end portion defines a third fluid opening;

a second septum extending through the second main body from the fourth end portion of the second main body toward the third end portion of the second main body, wherein the second septum divides the second fluid conduit into a tertiary lumen having a third cross-sectional area and a quaternary lumen having a fourth cross-sectional area less than the third cross-sectional area, and wherein the fourth end portion of the second main body defines a fourth fluid opening for the tertiary lumen; and a second leg extending form the second end portion of the main body, wherein the second leg defines a second leg lumen fluidly coupled to the quaternary lumen, and wherein the leg has an end portion defining a third fluid opening for the secondary lumen;

wherein the spanning member is configured to couple to the fourth end portion of the second main body to fluidly couple the spanning member lumen with the tertiary lumen with the fenestration region positioned between the first base member and the second base member.

17. The aortic repair system of example 16 wherein:

the first base member is configured to be implanted within an ascending portion of the aortic arch with the first leg positioned in a first branching vessel from the aortic arch, the second base member is configured to be implanted within a descending portion of the aortic arch with the second leg positioned in a second branching vessel from the aortic arch different than the first branching vessel, and the spanning member is configured to extend between the first base member and the second base member to align the fenestration region with a third branching vessel from the aortic arch different than the first and second branching vessels.

18. The aortic repair system of example 16 or example 17 wherein:

the first base member is implanted within an ascending portion of the aortic arch with the first leg positioned in a first branching vessel from the aortic arch, the second base member is implanted within a descending portion of the aortic arch with the second leg positioned in a second branching vessel from the aortic arch different than the first branching vessel, and the spanning member is coupled between the first base member and the second base member to align the fenestration region with a third branching vessel from the aortic arch different than the first and second branching vessels.

19. The aortic repair system of example 17 or example 18 wherein:

the first branching vessel is a brachiocephalic artery of the patient, the second branching vessel is a left subclavian artery of the patient, and the third branching vessel is a left common carotid artery of the patient.

20. The aortic repair system of any of examples 12-19 wherein the spanning member comprises a stent structure and graft material coupled to the stent structure to define the spanning member lumen, wherein the stent structure includes a mobile stent portion configured to move independent from adjacent portions of the stent structure and independent from the graft material, and wherein the mobile stent portion at least partially defines the fenestration region.

21. The aortic repair system of any of examples 12-20 wherein the spanning member comprises a stent structure including a plurality of struts, the plurality of struts comprising (i) a first plurality of struts made from a first material and (ii) a second plurality of struts made from a second material more penetrable than the first material, and wherein the second plurality of struts at least partially define the fenestration region.

22. The aortic repair system of example 21 wherein the first material is a metal.

23. The aortic repair system of example 21 or example 22 wherein the second material is a polymer.

24. The aortic repair system of any of examples 12-23 wherein the spanning member comprises a stent structure including a plurality of struts, the plurality of struts comprising (i) a first plurality of struts extending fully around the perimeter of the base member, and (ii) a second plurality of struts extending around only a portion of the perimeter of the base member to define a stent-free section along the perimeter of the base member, and wherein the stent-free section at least partially defines the fenestration region.

25. The aortic repair system of any of examples 12-24 wherein the spanning member comprises a stent structure and material coupled to the stent structure to define the spanning member lumen, wherein the material includes a first material having a first fenestration resistance and a second material having a second fenestration resistance less than the first fenestration resistance, and wherein the second material at least partially defines the fenestration region.

26. The aortic repair system of any of examples 12-25 wherein the spanning member comprises a stent structure and graft material coupled to the stent structure to define the spanning member lumen, the graft material comprising a first portion and a second portion radially aligned with the first portion, wherein at least one of the first portion and the second portion are configured to deflect radially inwardly into the fluid conduit of the base member.

27. The aortic repair system of any of examples 12-25, further comprising a branch perfusion member including a proximal region and a distal region, wherein the proximal region is configured to coupled to the spanning member at the fenestration region, and wherein the distal region is configured to extend radially outward from the spanning member toward the at least one branching vessel.

28. The aortic repair system of example 27 wherein at least a portion of the distal region is positioned within the at least one branching vessel.

29. The aortic repair system of example 27 or example 28 wherein the proximal region sealingly engages the spanning member at the fenestration region to at least partially prevent fluid within the spanning member lumen from leaking between the spanning member and the branch perfusion member.

30. An aortic repair system for use in an aortic arch of a patient, the aortic repair system comprising:

a base member having a first end portion, a second end portion opposite the first end portion, and a sidewall extending between the first and second end portions, the base member comprising— a stent frame;

a graft material extending around at least a portion of the stent frame to define a lumen through which blood can flow between the first end portion and the second end portion; and a fenestration in the sidewall of the base member, wherein the fenestration is configured to permit fluid flow into the lumen of the base member; and a centering tool comprising— a shaft having a proximal end portion; and an expandable component positioned at the proximal end portion and transitionable between a first state and a second state, wherein— in the first state, the expandable component has a low profile and is configured to be inserted through the fenestration of the base member into the lumen, and in the second state, the expandable component has an increased cross-sectional dimension than in the first state and is shaped and sized to press against an inner surface of the base member proximate to the fenestration.

31. The aortic repair system of example 30 wherein, when the expandable component is in the second state, the centering tool is configured to position the proximal end portion of the shaft substantially stationary relative to the fenestration.

32. The aortic repair system of claim 30 or example 31 wherein the fenestration is configured to be aligned with an ostium of a branching vessel of the aortic arch, and wherein the centering tool is configured to align the fenestration with the ostium.

33. The aortic repair system of any of examples 30-32 wherein the expandable component of the centering tool includes a braided disc.

34. The aortic repair system of any of examples 30-33 wherein the expandable component includes a proximal surface, a distal surface, and an apex portion therebetween, wherein the proximal surface and the distal surface are each angled radially outwardly from the shaft toward the apex portion.

35. The aortic repair system of example 34 wherein the distal surface includes a first region proximate the apex portion and a second region extending radially inward from the first region.
36. The aortic repair system of example 35 wherein the second region is angled relative to the first portion.
37. The aortic repair system of example 35 or example 36 wherein the second region defines a necked portion of the expandable component configured to extend at least partially through the fenestration when the first region is positioned to contact an interior surface of the base member.
38. A method of delivering an aortic arch repair device relative to a branch vessel of an aortic arch of a patient, the method comprising:

moving an expandable component of a centering tool through the branch vessel in a first direction toward the aortic arch while the expandable component is in a delivery state, wherein the expandable component has a low profile in the delivery state;

extending the expandable component through a pre-fenestrated opening of a first member of the aortic arch repair device with the expandable component in the delivery state;

transitioning the expandable component from the delivery state to an expanded state, wherein the expandable component has a larger cross-sectional dimension in the expanded state larger than the low profile in the delivery state; and moving the expandable component in a second direction opposite the first direction to press against an inner surface of the first member of the aortic arch repair device.

39. The method of example 38, further comprising positioning a branch perfusion member relative to the aortic arch repair device such that a first end of the branch perfusion is proximate the pre-fenestrated opening and a second end of the branch perfusion member extends away from the pre-fenestrated opening.
40. The method of example 39, further comprising coupling the first end of the branch perfusion member to the aortic arch repair device.
41. The method of example 39 or example 40 wherein positioning the branch perfusion member includes inserting the first end of the branch perfusion member through the pre-fenestrated opening and into an interior of the base member.
42. The method of any of examples 38-41, further comprising coupling the first member to a second member of the aortic arch repair device, wherein the second member is positioned proximally of the first member and/or in an ascending portion of the aortic arch.
43. The method of any of examples 38-42, further comprising coupling the first member to a second member of the aortic arch repair device, wherein the second member is positioned distally of the first member and/or in a descending portion of the aortic arch.
44. The method of example 42 or example 43 wherein the second member is a base member and the first member is a spanning member coupled to the base member.
45. An aortic repair system for use in an aortic arch of a patient, the aortic repair system comprising:

a base member having a first end portion, a second end portion opposite the first end portion, and a sidewall extending between the first and second end portions, the base member comprising—
  a stent frame; and
  a graft material extending around at least a portion of the stent frame to define a lumen through which blood can flow between the first end portion and the second end portion; and a centering tool comprising—
  a shaft having a proximal end portion; and
  an expandable component positioned at the proximal end portion and transitionable between a first state and a second state,
  wherein—
    in the first state, the expandable component has a low profile and is configured to be inserted through a fenestration in the base member into the lumen, and
    in the second state, the expandable component has an increased cross-sectional dimension than in the first state and is shaped and sized to press against an inner surface of a branch vessel of the patient.

46. The aortic repair system of example 45 wherein base member further comprises an opening extending through the graft material and the stent frame to define the fenestration.
47. The aortic repair system of example 45 or example 46 wherein the fenestration is formed in the base member before the base member is positioned within the aortic arch.
48. The aortic repair system of any of examples 45-47 wherein the fenestration is formed in the base member while at least a portion of the base member is positioned within the aortic arch
49. The aortic repair system of any of examples 45-48, further comprising a cutting tool configured to penetrate through the graft material to form the fenestration in the base member.
50. The aortic repair system of example 49 wherein the shaft of the centering tool defines a centering tool lumen, and wherein the cutting tool is slidably positionable within the centering tool lumen.
51. The aortic repair system of any of examples 45-50 wherein the expandable element includes a balloon.
52. The aortic repair system of any of examples 45-51 wherein the expandable element includes a braided balloon.
53. The aortic repair system of any of examples 45-52 wherein the expandable elements include a plurality of expandable struts configured to move radially inward or outward relative to shaft.
54. The aortic repair system of any of examples 45-53 wherein the shaft is a first shaft including a first coupling element, the centering tool further comprising a second shaft including a second coupling element configured to matingly engage the first coupling element of the first shaft.
55. The aortic repair system of example 54 wherein the first coupling element includes a first magnet and wherein the second coupling element includes a second magnet configured to magnetically couple the second shaft to the first shaft.
56. The aortic repair system of example 54 or example 55 wherein the first shaft defines a first shaft lumen, wherein the second shaft defines a second shaft lumen, and wherein the first shaft lumen is at least partially aligned with the second shaft lumen when the first coupling element matingly engages the second coupling element.
57. The aortic repair system of any of examples 54-56 wherein the first coupling element is configured to matingly engage the second coupling element across the graft material of the base member.

58. An aortic repair system for use in an aortic arch of a patient, the aortic repair system comprising:

a base member having a first end portion, a second end portion opposite the first end portion, and a sidewall extending between the first and second end portions, the base member comprising— a stent frame; and a graft material extending around at least a portion of the stent frame to define a lumen through which blood can flow between the first end portion and the second end portion; and a cutting zone tool comprising— a body having a distal end portion positionable within at least one branch vessel of the aortic arch; and a catcher component coupled to the distal end portion, wherein the catcher component is (i) positionable to deform at least a portion of the aortic arch repair device away from the opening and (ii) configured to at least partially prevent material from the aortic arch repair device from entering the opening of the aortic arch branch vessel.

59. The aortic arch repair system of example 58 wherein the catcher component includes a plurality of struts extending radially outward from the longitudinal axis of the body and distally from the distal end portion.

60. The aortic arch repair system of example 59 wherein the catcher component further includes a funnel positioned at least partially between individual ones of the plurality of struts.

61. The aortic arch repair system of any of examples 58-60 wherein the catcher component includes a braided funnel extending radially outward from the longitudinal axis of the body and distally from the distal end portion.

62. The aortic arch repair system of any of examples 58-61 wherein the catcher component includes an expandable balloon, wherein the expandable balloon includes a first region having a first stiffness and a second region opposite the first region and having a second stiffness less than the first region, wherein the first region is positionable to deform at least the portion of the aortic arch repair device.

63. The aortic arch repair system of any of examples 58-62 wherein the catcher component includes a plurality of deformable struts defining an interior of the catcher component and a filter positioned within the interior.

64. The aortic arch repair system of example 63 wherein the filter has a hemispherical shape.

65. The aortic arch repair system of example 63 or example 64 wherein the filter has a concave surface positioned to face distally toward the distal end portion of the body.

66. A method of treating a patient's aortic arch, the method comprising:

positioning a cutting zone tool proximate an aortic arch repair device;

deploying a catcher component of the cutting zone tool, wherein deploying the catcher component includes— expanding the catcher component from a first, low-profile delivery state to a second, state having a greater cross-sectional dimension, and positioning the catcher component relative to the aortic arch repair device to form a cutting zone at least partially between the aortic arch repair device and an inner surface of the catcher component; and forming a fenestration in the aortic arch repair device within the cutting zone.

67. The method of example 66 wherein forming the fenestration includes advancing a cutting tool away from the cutting zone through the aortic arch repair device.

68. The method of example 66 or example 67 wherein forming the fenestration includes retracting the cutting tool toward the cutting zone through the aortic arch repair device.

69. The method of any of examples 66-68 wherein positioning the catcher component includes positioning the catcher component through an ostium of a branching vessel of the aortic arch, and wherein deploying the catcher component includes deploying the catcher component with the catcher component extending through the ostium.

70. The method of any of examples 66-69 wherein the catcher component includes a funnel, and wherein expanding the catcher component includes expanding the funnel to form the cutting zone.

71. The method of any of examples 66-70 wherein the catcher component includes a balloon, and wherein expanding the catcher component includes inflating the balloon to form the cutting zone.

72. The method of example 71 wherein the balloon includes a proximal region having a first stiffness and a distal region having a second stiffness greater than the first stiffness, wherein inflating the balloon includes inflating the balloon with the first region positioned at least partially within a branching vessel of the aortic arch, and wherein positioning the catcher component includes positioning the distal region against the base member.

73. The method of any of examples 66-72 wherein the catcher component includes a plurality of struts extending at least generally parallel to a shaft of the cutting zone tool, and wherein expanding the catcher component includes flexing individual ones of the plurality of structs radially outwardly from the shaft to contact a branching vessel of the aortic arch.

74. An aortic repair system for use in an aortic arch of a patient, the aortic repair system comprising:

a base member having a first end portion, a second end portion opposite the first end portion, and a sidewall extending between the first and second end portions, the base member comprising— a stent frame; and a graft material extending around at least a portion of the stent frame to define a lumen through which blood can flow between the first end portion and the second end portion; and a cutting tool configured to penetrate the graft material to form a fenestration in the base member.

75. The aortic repair system of example 74 wherein the cutting tool comprises:

a first cutting feature having a first width; and a second cutting feature positioned proximally from the first cutting feature, wherein the second cutting feature is transitionable between (i) a first state in which the second cutting feature defines a second width less than the first width, and (ii) a second state in which the second cutting feature defines a third width greater than the first width.

76. The aortic repair system of example 75 wherein the second cutting feature includes a cutting cage comprising a plurality of expandable struts, wherein individual ones of the plurality of expandable struts include a distal cutting surface.
77. The aortic repair system of any of examples 74-76, further comprising a cutting zone tool defining a cutting zone tool lumen, wherein the cutting tool is configured to be slidably disposed within the cutting zone tool and to be advanced distally relative to the cutting zone tool toward the base member to form the fenestration.
78. The aortic repair system of any of examples 74-77 wherein the cutting tool includes a circular cutting feature, the aortic repair system further comprising a grasper tool configured to engage the graft material of the base member and position a portion of the graft material within the circular cutting feature, wherein the circular cutting feature is configured to move relative to the grasper tool to cut through the portion of the graft material to form the fenestration.
79. The aortic repair system of example 78 wherein the circular cutting feature is configured to move laterally relative to the grasper tool or the base member to cut through the portion of the graft material and form the fenestration.
80. The aortic repair system of example 78 wherein the circular cutting feature is configured to tighten around the portion of the graft material to cut through the portion and form the fenestration.
81. The aortic repair system of any of examples 78-80 wherein the grasper tool is transitionable between a first, low-profile delivery state and a second, expanded state in which the grasper tool is configured to engage the graft material.
82. An aortic arch repair device, comprising:
a base member configured to be positioned within an aortic arch of a patient; and
a branch perfusion member comprising—
an elongate portion positionable at least partially within a branch vessel of the aortic arch and having a first width; and
a coupling portion having a second width greater than the first width, wherein the coupling portion is configured to couple the branch perfusion member to the base member.
83. The aortic arch repair device of example 82 wherein the coupling portion includes one or more rings sized to receive the base member.
84. The aortic arch repair device of example 82 or example 83 wherein the elongate portion is transitionable between a delivery state and a deployed state, and wherein the coupling portion includes one or more projections that extend radially outward from the elongate portion when the elongate portion is in the deployed state.
85. The aortic arch repair device of any of examples 82-84 wherein the coupling portion has a first region including graft material and a second, graft material free region.
86. The aortic arch repair device of example 85 wherein the second region is positioned radially outwardly from the first region.
87. The aortic arch repair device of any of examples 82-86 wherein the coupling portion includes a plurality of cells extending radially outwardly from the elongate portion, wherein individual ones of the plurality of cells are configured to flex relative one or more others of the plurality of cells.
88. The aortic arch repair device of any of examples 82-87 wherein the coupling portion is a first coupling portion, the aortic arch repair device further comprising a second coupling portion positioned proximally from the first coupling portion, wherein the first coupling portion is configured to engage an inner surface of the base member and the second coupling portion is configured to engage an outer surface of the base member.
89. The aortic arch repair device of any of examples 82-88 wherein the branch perfusion member is a first branch perfusion member comprising a first elongate portion and a first coupling portion configured to couple the first branch perfusion member to an outer surface of the base member, the aortic arch repair device further comprising a second branch perfusion member comprising—
a second elongate portion positionable at least partially within the first elongate portion, and
a second coupling portion configured to couple the second branch perfusion member to an inner surface of the base member.
90. A method of treating a diseased region of an aortic arch of a patient, the method comprising:
positioning a base member of an aortic arch repair device in the aortic arch with the base component in a low-profile, delivery state, wherein the base member comprises a stent frame and a graft material that define a lumen for blood to bypass the diseased region of the aortic arch;
positioning a branch delivery device in a branch vessel extending from the aortic arch such that a distal end portion of the branch delivery device is positioned distal to an anastomosis of the branch vessel and the aortic arch, wherein the branch delivery device comprises a cutting feature;
transitioning the base member from the low-profile delivery state to a deployed state, wherein transitioning the base member causes the cutting feature of the branch delivery device to pierce a sidewall of the base member to form a fenestration in the sidewall;
positioning a coupling portion of a branch perfusion member proximate the fenestration;
expanding the branch perfusion member; and
coupling the coupling portion of the branch perfusion member to the base member.
91. A method of repairing a thoracic aorta, the method comprising:
intravascularly delivering an aortic repair device to a target site in the thoracic aorta;
positioning a main body of the aortic repair device such that an exterior surface of the main body sealingly contacts a wall of the thoracic aorta, a first fluid opening of the main body is positioned to receive blood flow from the thoracic aorta, and a second fluid opening of the main body is positioned to discharge a first portion of the blood flow into the thoracic aorta,
wherein the aortic repair device comprises a septum extending at least partially between the first fluid opening and the second fluid opening of the main body, the septum dividing the main body into a primary lumen and a secondary lumen, and
wherein the first fluid opening of the main body is fluidly coupled to the primary lumen to receive the first portion of the blood flow therethrough;

positioning at least a portion of a leg of the aortic repair device within a first branch vessel branching from the thoracic aorta such that a third fluid opening of the leg is positioned within the first branch vessel to discharge a second portion of the blood flow into the first branch vessel, wherein the third fluid opening is fluidly coupled to the secondary lumen to receive the second portion of the blood flow therethrough; and positioning at least a portion of a spanning member of the aortic repair device within a portion of the primary lumen of the main body, wherein the spanning member includes a fenestration region configured to align with a second branch vessel branching from the aortic arch, and wherein the fenestration region is configured to be pierced to form a fenestration in the spanning member to perfuse the second branch vessel.

92. The method of example 91 wherein the main body has a length extending between the first fluid opening and the second fluid opening, and wherein positioning the main body of the aortic repair device includes positioning the main body to sealingly contact the wall of the thoracic aorta along substantially the entire length of the main body.

93. The method of example 91 or example 92 wherein the wall of the thoracic aorta is a wall of an ascending portion of the thoracic aorta, wherein the leg extends from the main body proximate to the second fluid opening, and wherein the septum extends from the second fluid opening at least partially toward the first fluid opening.

94. The method of example 93 wherein the first branch vessel is a brachiocephalic artery.

95. The method of example 93 wherein the first branch vessel or the second branch vessel is a left subclavian artery.

96. The method of example 93 wherein the first branch vessel or the second branch vessel is a left common carotid artery.

97. The method of examples 91-96 wherein the wall of the thoracic aorta is a wall of a descending portion of the thoracic aorta, wherein the leg extends from the main body proximate to the first fluid opening, and wherein the septum extends from the first fluid opening at least partially toward the first fluid opening.

98. The method of example 97 wherein the first branch vessel is a left subclavian artery.

99. The method of example 97 wherein the first branch vessel or the second branch vessel is a brachiocephalic artery.

100. The method of example 97 wherein the first branch vessel or the second branch vessel is a left common carotid artery.

101. The method of any one of examples 91-100 wherein positioning the spanning member includes expanding a stent structure at least partially within the secondary lumen.

102. The method of example 101 wherein expanding the stent structure includes deploying a tubular stent at least partially within the secondary lumen.

103. The method of example 101 or example 102 wherein expanding the stent structure includes permitting a plurality of stents within the secondary lumen to self-expand.

104. The method of example 91 wherein the wall of the thoracic aorta is a wall of an ascending portion of the thoracic aorta, wherein the leg extends from the main body proximate to the second fluid opening, and wherein positioning the portion of the spanning member within the portion of the primary lumen of the main body includes inserting the portion of the spanning member through the second fluid opening.

105. The method of example 104 wherein inserting the portion of the spanning member through the second fluid opening includes inserting a proximal portion of the spanning member through the second fluid opening and positioning a distal portion of the spanning member to discharge the first portion of the blood flow into the descending portion of the thoracic aorta.

106. The method of example 91 wherein the wall of the thoracic aorta is a wall of a descending portion of the thoracic aorta, wherein the leg extends from the main body proximate to the first fluid opening, and wherein positioning the portion of the spanning member within the portion of the primary lumen of the main body includes inserting the portion of the spanning member through the first fluid opening.

107. The method of example 106 wherein inserting the portion of the spanning member through the first fluid opening includes inserting a distal portion of the spanning member through the first fluid opening and positioning a proximal portion of the spanning member to receive blood flow from the ascending portion of the thoracic aorta.

108. The method of any one of examples 91-107 wherein positioning the main body of the aortic repair device includes positioning the main body adjacent to an aortic aneurysm.

109. The method of any one of examples 91-108 wherein positioning the main body of the aortic repair device includes positioning the main body adjacent to an aortic dissection.

110. The method of any one of examples 91-109, further comprising:

forming a fenestration through the fenestration region; and positioning a branch perfusion member to (i) receive fluid from within the spanning member via the fenestration and (ii) discharge the received fluid into the second branch vessel.

111. The method of example 110 wherein positioning the branch perfusion member includes positioning at least a portion of the branch perfusion member through the fenestration and/or within the spanning member.

112. The method of example 110 wherein forming the fenestration comprises moving a fenestration tool positioned within the second branch vessel in a first direction through the fenestration region and at least partially into the spanning member.

113. The method of example 112 wherein forming the fenestration further comprises:

expanding the fenestration tool; and moving the expanded fenestration tool in a second direction, opposite the first direction, toward and/or into the second branch vessel.

114. The method of example 110 wherein forming the fenestration comprises moving a fenestration tool positioned within the spanning member in a first direction through the fenestration region, toward and/or at least partially into the second branch vessel.

115. The method of example 114 wherein forming the fenestration further comprises:

expanding the fenestration tool; and moving the expanded fenestration tool in a second direction, opposite the first direction, toward and/or into the spanning member.

116. The method of example 91 wherein the main body is a first main body positioned in the ascending portion of the thoracic aorta and the leg is a first leg, the method further comprising:

positioning a second main body of the aortic repair device such that an exterior surface of the second main body sealingly contacts a second wall of the descending portion of the thoracic aorta, a fourth fluid opening of the second main body is positioned to receive blood flow from the ascending portion of the thoracic aorta, and a fifth fluid opening of the main body is positioned to discharge the first portion of the blood flow into the descending portion of the thoracic aorta, wherein the aortic repair device comprises a second septum extending at least partially between the fourth fluid opening and the fifth fluid opening of the second main body, the second septum dividing the second main body into a tertiary lumen and a quaternary lumen, wherein the fourth fluid opening of the second main body is fluidly coupled to the tertiary lumen to receive the first portion of the blood flow therethrough, and wherein the spanning member extends between the first main body and the second main body; and positioning at least a portion of a second leg of the aortic repair device within a third branch vessel branching from the thoracic aorta such that a sixth fluid opening of the second leg is positioned within the third branch vessel to discharge a third portion of the blood flow into the third branch vessel, wherein the sixth fluid opening is fluidly coupled to the secondary lumen to receive the second portion of the blood flow therethrough.

117. The method of example 116 wherein:

the first branch vessel is a brachiocephalic artery, the second branch vessel is a left common carotid artery, and the third branch vessel is a left subclavian artery.

118. An aortic repair system for use in an aortic arch of a patient, the aortic repair system comprising:

a base member having a first end portion, a second end portion opposite the first end portion, and a sidewall extending between the first and second end portions, the base member comprising— a stent frame; and a graft material extending around at least a portion of the stent frame to define a lumen through which blood can flow between the first end portion and the second end portion; and a cutting zone tool comprising— a body having a distal end portion positionable within at least one branch vessel of the aortic arch; and a catcher component coupled to the distal end portion, wherein the catcher component is (i) positionable to deform at least a portion of the aortic arch repair device away from the opening and (ii) configured to at least partially prevent a cutting tool for fenestrating the base member from contacting the aortic arch of the patient and/or the aortic arch branch vessel during fenestration.

119. A method of treating a patient's aortic arch, the method comprising:

positioning a cutting zone tool proximate an aortic arch repair device;

deploying a catcher component of the cutting zone tool, wherein deploying the catcher component includes— expanding the catcher component from a first, low-profile delivery state to a second, state having a greater cross-sectional dimension, and positioning the catcher component relative to the aortic arch repair device to form a cutting zone at least partially between the aortic arch repair device and an inner surface of the catcher component; and forming a fenestration in the aortic arch repair device within the cutting zone, wherein forming the fenestration includes piercing the aortic arch repair device with a cutting tool while keeping the catcher component positioned between the cutting tool and the patient's aortic arch.

VIII. CONCLUSION

The above detailed description of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments can perform steps in a different order. The various embodiments described herein can also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms can also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications can be made without deviating from the technology. Further, while advantages associated with some embodiments of the technology have been described in the context of those embodiments, other embodiments can also exhibit such advantages, and not all embodiments need necessarily exhibit such advantages to fall within the scope of the technology. Accordingly, the disclosure and associated technology can encompass other embodiments not expressly shown or described herein.

We claim:

1. An aortic repair system for treating an aortic arch of a patient, the aortic repair system comprising:

a base member, comprising— a main body having a first end portion and a second end portion, wherein the main body defines a fluid conduit, and wherein the first end portion defines a first fluid opening;

a septum extending through the main body from the second end portion of the main body toward the first end portion of the main body, wherein the septum divides the fluid conduit into a primary lumen having a first cross-sectional area and a secondary lumen having a second cross-sectional area less than the first cross-sectional area, and wherein the second end portion of the main body defines a second fluid opening for the primary lumen; and a leg extending from the second end portion of the main body, wherein the leg defines a leg lumen fluidly coupled to the secondary lumen, and wherein the leg has an end portion defining a third fluid opening for the secondary lumen;

a spanning member configured to be coupled to the second end portion of the main body, the spanning member defining a spanning member lumen configured to be fluidly coupled to the primary lumen via the second fluid opening, wherein the spanning member includes a fenestration region sized and shaped to align with at least one branching vessel from the aortic arch, and wherein the fenestration region is configured to be pierced to form a fenestration in the spanning member to perfuse the at least one branching vessel, wherein the spanning member comprises:

a first spanning member comprising a stent structure including a plurality of struts, the plurality of struts comprising a first plurality of struts extending fully around a perimeter of the spanning member, and a second plurality of struts extending around only a portion of the perimeter of the first spanning member to define a stent-free section along the perimeter of the spanning member, and wherein the stent-free section at least partially defines the fenestration region; or a second spanning member comprising a stent structure and material coupled to the stent structure to define the spanning member lumen, wherein the material includes a first material having a first fenestration resistance and a second material having a second fenestration resistance less than the first fenestration resistance, and wherein the second material at least partially defines the fenestration region; or a third spanning member comprising a stent structure and graft material coupled to the stent structure to define the spanning member lumen, the graft material comprising a first portion and a second portion radially aligned with the first portion, wherein at least one of the first portion and the second portion are configured to deflect radially inwardly into the spanning member lumen.

2. The aortic repair system of claim 1 wherein:

the base member is configured to be implanted within an ascending portion of the aortic arch with the leg positioned in a first branching vessel from the aortic arch, and the spanning member is configured to extend from the base member toward and/or into a descending portion of the aortic arch to align the fenestration region with a second branching vessel from the aortic arch different than the first branching vessel.

3. The aortic repair system of claim 1 wherein:

the base member is implanted within an ascending portion of the aortic arch with the leg positioned in a first branching vessel from the aortic arch, and the spanning member is coupled to the second end portion of the base member and extends from the base member toward and/or into a descending portion of the aortic arch to align the fenestration region with a second branching vessel from the aortic arch different than the first branching vessel.

4. The aortic repair system of claim 2 wherein:

the first branching vessel is a brachiocephalic artery of the patient, and the second branching vessel is a left common carotid artery or a left subclavian artery of the patient.

5. The aortic repair system of claim 1 wherein the base member is a first base member having a first main body defining a first fluid conduit, a first septum, and a first leg, the aortic repair system further comprising:

a second base member, comprising— a second main body having a third end portion and a fourth end portion, wherein the second main body defines a second fluid conduit, and wherein the third end portion defines a fourth fluid opening;

a second septum extending through the second main body from the fourth end portion of the second main body toward the third end portion of the second main body, wherein the second septum divides the second fluid conduit into a tertiary lumen having a third cross-sectional area and a quaternary lumen having a fourth cross-sectional area less than the third cross-sectional area, and wherein the fourth end portion of the second main body defines a fifth fluid opening for the tertiary lumen; and a second leg extending from the fourth end portion of the second main body, wherein the second leg defines a second leg lumen fluidly coupled to the quaternary lumen, and wherein the second leg has an end portion defining a sixth fluid opening for the quaternary lumen;

wherein the spanning member is configured to couple to the fourth end portion of the second main body to fluidly couple the spanning member lumen with the tertiary lumen, with the fenestration region positioned between the first base member and the second base member.

6. The aortic repair system of claim 5 wherein:

the first base member is configured to be implanted within an ascending portion of the aortic arch with the first leg positioned in a first branching vessel from the aortic arch, the second base member is configured to be implanted within a descending portion of the aortic arch with the second leg positioned in a second branching vessel from the aortic arch different than the first branching vessel, and the spanning member is configured to extend between the first base member and the second base member to align the fenestration region with a third branching vessel from the aortic arch different than the first and second branching vessels.

7. The aortic repair system of claim 5 wherein:

the first base member is implanted within an ascending portion of the aortic arch with the first leg positioned in a first branching vessel from the aortic arch, the second base member is implanted within a descending portion of the aortic arch with the second leg positioned in a second branching vessel from the aortic arch different than the first branching vessel, and the spanning member is coupled between the first base member and the second base member to align the fenestration region with a third branching vessel from the aortic arch different than the first and second branching vessels.

8. The aortic repair system of claim 6 wherein:

the first branching vessel is a brachiocephalic artery of the patient, the second branching vessel is a left subclavian artery of the patient, and the third branching vessel is a left common carotid artery of the patient.

9. The aortic repair system of claim 1 wherein the spanning member is the first spanning member.

10. The aortic repair system of claim 1 wherein the spanning member is the second spanning member.

11. The aortic repair system of claim 1 wherein the spanning member is the third spanning member.

12. The aortic repair system of claim 1, further comprising a branch perfusion member including a proximal region and a distal region, wherein the proximal region is configured to coupled to the spanning member at the fenestration region, and wherein the distal region is configured to extend radially outward from the spanning member toward the at least one branching vessel.

13. The aortic repair system of claim 12 wherein at least a portion of the distal region is positioned within the at least one branching vessel.

14. The aortic repair system of claim 12 wherein the proximal region sealingly engages the spanning member at the fenestration region to at least partially prevent fluid within the spanning member lumen from leaking between the spanning member and the branch perfusion member.

15. A method of repairing a thoracic aorta, the method comprising:

intravascularly delivering an aortic repair device to a target site in the thoracic aorta;

positioning a main body of the aortic repair device such that an exterior surface of the main body sealingly contacts a wall of the thoracic aorta, a first fluid opening of the main body is positioned to receive blood flow from the thoracic aorta, and a second fluid opening of the main body is positioned to discharge a first portion of the blood flow into the thoracic aorta, wherein the aortic repair device comprises a septum extending at least partially between the first fluid opening and the second fluid opening of the main body, the septum dividing the main body into a primary lumen and a secondary lumen, and wherein the first fluid opening of the main body is fluidly coupled to the primary lumen to receive the first portion of the blood flow therethrough;

positioning at least a portion of a leg of the aortic repair device within a first branch vessel branching from the thoracic aorta such that a third fluid opening of the leg is positioned within the first branch vessel to discharge a second portion of the blood flow into the first branch vessel, wherein the third fluid opening is fluidly coupled to the secondary lumen to receive the second portion of the blood flow therethrough;

positioning at least a portion of a spanning member of the aortic repair device within a portion of the primary lumen of the main body, wherein the spanning member includes a fenestration region configured to align with a second branch vessel branching from the thoracic aorta, and wherein the fenestration region is configured to be pierced to form a fenestration in the spanning member to perfuse the second branch vessel;

forming a fenestration through the fenestration region, wherein forming the fenestration comprises:

moving a fenestration tool positioned within the second branch vessel in a first direction through the fenestration region and at least partially into the spanning member; or moving a fenestration tool positioned within the spanning member in a second direction through the fenestration region, toward and/or at least partially into the second branch vessel; and positioning a branch perfusion member to receive fluid from within the spanning member via the fenestration and to discharge the received fluid into the second branch vessel.

16. The method of claim 15 wherein positioning the branch perfusion member includes positioning at least a portion of the branch perfusion member through the fenestration and/or within the spanning member.

17. The method of claim 15 wherein forming the fenestration comprises moving the fenestration tool positioned within the second branch vessel in the first direction through the fenestration region and at least partially into the spanning member.

18. The method of claim 17 wherein forming the fenestration further comprises:

expanding the fenestration tool; and moving the expanded fenestration tool in the second direction, opposite the first direction, toward and/or into the second branch vessel.

19. The method of claim 15 wherein forming the fenestration comprises moving the fenestration tool positioned within the spanning member in the second direction through the fenestration region, toward and/or at least partially into the second branch vessel.

20. The method of claim 19 wherein forming the fenestration further comprises:

expanding the fenestration tool; and moving the expanded fenestration tool in the first direction, opposite the second direction, toward and/or into the spanning member.

21. The method of claim 15 wherein the main body is a first main body positioned in an ascending portion of the thoracic aorta and the leg is a first leg, the method further comprising:

positioning a second main body of the aortic repair device such that an exterior surface of the second main body sealingly contacts a second wall of a descending portion of the thoracic aorta, a fourth fluid opening of the second main body is positioned to receive blood flow from the ascending portion of the thoracic aorta, and a fifth fluid opening of the main body is positioned to discharge the first portion of the blood flow into the descending portion of the thoracic aorta, wherein the aortic repair device comprises a second septum extending at least partially between the fourth fluid opening and the fifth fluid opening of the second main body, the second septum dividing the second main body into a tertiary lumen and a quaternary lumen, wherein the fourth fluid opening of the second main body is fluidly coupled to the tertiary lumen to receive the first portion of the blood flow therethrough, and wherein the spanning member extends between the first main body and the second main body; and positioning at least a portion of a second leg of the aortic repair device within a third branch vessel branching from the thoracic aorta such that a sixth fluid opening of the second leg is positioned within the third branch vessel to discharge a third portion of the blood flow into the third branch vessel, wherein the sixth fluid opening is fluidly coupled to the quaternary lumen to receive the second portion of the blood flow therethrough.

22. The method of claim 21 wherein:

the first branch vessel is a brachiocephalic artery, the second branch vessel is a left common carotid artery, and the third branch vessel is a left subclavian artery.

23. The method of claim 15 wherein the main body has a length extending between the first fluid opening and the second fluid opening, and wherein positioning the main body of the aortic repair device includes positioning the main body to sealingly contact the wall of the thoracic aorta along substantially the entire length of the main body.

24. The method of claim 15 wherein the wall of the thoracic aorta is a wall of an ascending portion of the thoracic aorta, wherein the leg extends from the main body proximate to the second fluid opening, and wherein the septum extends from the second fluid opening at least partially toward the first fluid opening.

25. The method of claim 24 wherein the first branch vessel is a brachiocephalic artery.

26. The method of claim 24 wherein the first branch vessel or the second branch vessel is a left subclavian artery.

27. The method of claim 24 wherein the first branch vessel or the second branch vessel is a left common carotid artery.

28. The method of claim 15 wherein the wall of the thoracic aorta is a wall of a descending portion of the thoracic aorta, wherein the leg extends from the main body proximate to the first fluid opening, and wherein the septum extends from the first fluid opening at least partially toward the first second fluid opening.

29. The method of claim 28 wherein the first branch vessel is a left subclavian artery.

30. The method of claim 28 wherein the first branch vessel or the second branch vessel is a brachiocephalic artery.

31. The method of claim 28 wherein the first branch vessel or the second branch vessel is a left common carotid artery.

32. The method of claim 15 wherein positioning the spanning member includes expanding a stent structure at least partially within the primary lumen.

33. The method of claim 32 wherein expanding the stent structure includes deploying a tubular stent at least partially within the primary lumen.

34. The method of claim 32 wherein expanding the stent structure includes permitting a plurality of stents within the primary lumen to self-expand.

35. The method of claim 15 wherein the wall of the thoracic aorta is a wall of an ascending portion of the thoracic aorta, wherein the leg extends from the main body proximate to the second fluid opening, and wherein positioning the portion of the spanning member within the portion of the primary lumen of the main body includes inserting the portion of the spanning member through the second fluid opening.

36. The method of claim 35 wherein inserting the portion of the spanning member through the second fluid opening includes inserting a proximal portion of the spanning member through the second fluid opening and positioning a distal portion of the spanning member to discharge the first portion of the blood flow into a descending portion of the thoracic aorta.

37. The method of claim 15 wherein the wall of the thoracic aorta is a wall of a descending portion of the thoracic aorta, wherein the leg extends from the main body proximate to the first fluid opening, and wherein positioning the portion of the spanning member within the portion of the primary lumen of the main body includes inserting the portion of the spanning member through the first fluid opening.

38. The method of claim 37 wherein inserting the portion of the spanning member through the first fluid opening includes inserting a distal portion of the spanning member through the first fluid opening and positioning a proximal portion of the spanning member to receive blood flow from an ascending portion of the thoracic aorta.

39. The method of claim 15 wherein positioning the main body of the aortic repair device includes positioning the main body adjacent to an aortic aneurysm.

40. The method of claim 15 wherein positioning the main body of the aortic repair device includes positioning the main body adjacent to an aortic dissection.

* * * * *